US010911829B2

(12) United States Patent
el Kaliouby et al.

(10) Patent No.: US 10,911,829 B2
(45) Date of Patent: *Feb. 2, 2021

(54) VEHICLE VIDEO RECOMMENDATION VIA AFFECT

(71) Applicant: Affectiva, Inc., Boston, MA (US)

(72) Inventors: Rana el Kaliouby, Milton, MA (US); Abdelrahman N. Mahmoud, Somerville, MA (US); Panu James Turcot, Pacifica, CA (US)

(73) Assignee: Affectiva, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/408,552

(22) Filed: May 10, 2019

(65) Prior Publication Data
US 2019/0268660 A1    Aug. 29, 2019

Related U.S. Application Data

(63) Continuation-in-part of application No. 15/357,585, filed on Nov. 21, 2016, now Pat. No. 10,289,898, (Continued)

(51) Int. Cl.
*H04N 21/466* (2011.01)
*H04N 21/4223* (2011.01)
(Continued)

(52) U.S. Cl.
CPC ....... *H04N 21/4668* (2013.01); *A61B 5/0077* (2013.01); *A61B 5/165* (2013.01);
(Continued)

(58) Field of Classification Search
CPC ......... H04N 21/44218; H04N 21/4223; H04N 21/42201; H04N 21/4667; H04N 21/4668;
(Continued)

(56) References Cited

U.S. PATENT DOCUMENTS

| 3,034,500 A | 5/1962 | Backster, Jr. |
| 3,548,806 A | 12/1970 | Fisher |

(Continued)

FOREIGN PATENT DOCUMENTS

| JP | 08115367 | 7/1996 |
| KR | 10-2005-0021759 A | 3/2005 |

(Continued)

OTHER PUBLICATIONS

Rana Ayman El Kaliouby, Mind-reading machines: automated inference of complex mental states, Jul. 2005, University of Cambridge, Cambridge, United Kingdom.

(Continued)

*Primary Examiner* — Cynthia M Fogg
(74) *Attorney, Agent, or Firm* — Adams Intellex, PLC

(57) ABSTRACT

Techniques are disclosed for vehicle video recommendation via affect. A first media presentation is played to a vehicle occupant. The playing is accomplished using a video client. Cognitive state data for the vehicle occupant is captured, where the cognitive state data includes video facial data from the vehicle occupant during the first media presentation playing. The first media presentation is ranked, on an analysis server, relative to another media presentation based on the cognitive state data which was captured for the vehicle occupant. The ranking is determined for the vehicle occupant. The cognitive state data which was captured for the vehicle occupant is correlated, on the analysis server, to cognitive state data collected from other people who experienced the first media presentation. One or more further media presentation selections are recommended to the vehicle occupant, based on the ranking and the correlating.

27 Claims, 20 Drawing Sheets

Related U.S. Application Data which is a continuation-in-part of application No. 15/262,197, filed on Sep. 12, 2016, now abandoned, which is a continuation-in-part of application No. 14/821,896, filed on Aug. 10, 2015, now Pat. No. 9,503,786, application No. 15/262,197, which is a continuation-in-part of application No. 14/796,419, filed on Jul. 10, 2015, now abandoned, application No. 14/821,896, which is a continuation-in-part of application No. 14/796,419, filed on Jul. 10, 2015, now abandoned, which is a continuation of application No. 13/406,068, filed on Feb. 27, 2012, now Pat. No. 9,106,958, application No. 14/796,419, which is a continuation-in-part of application No. 14/460,915, filed on Aug. 15, 2014, now abandoned, which is a continuation-in-part of application No. 13/153,745, filed on Jun. 6, 2011, now abandoned.

(60) Provisional application No. 62/827,088, filed on Mar. 21, 2019, provisional application No. 62/679,825, filed on Jun. 3, 2018, provisional application No. 62/370,421, filed on Aug. 3, 2016, provisional application No. 62/301,558, filed on Feb. 29, 2016, provisional application No. 62/273,896, filed on Dec. 31, 2015, provisional application No. 62/265,937, filed on Dec. 10, 2015, provisional application No. 62/222,518, filed on Sep. 23, 2015, provisional application No. 62/217,872, filed on Sep. 12, 2015, provisional application No. 62/128,974, filed on Mar. 5, 2015, provisional application No. 62/082,579, filed on Nov. 20, 2014, provisional application No. 62/047,508, filed on Sep. 8, 2014, provisional application No. 62/023,800, filed on Jul. 11, 2014, provisional application No. 61/972,314, filed on Mar. 30, 2014, provisional application No. 61/953,878, filed on Mar. 16, 2014, provisional application No. 61/927,481, filed on Jan. 15, 2014, provisional application No. 61/924,252, filed on Jan. 7, 2014, provisional application No. 61/916,190, filed on Dec. 14, 2013, provisional application No. 61/867,007, filed on Aug. 16, 2013, provisional application No. 61/581,913, filed on Dec. 30, 2011, provisional application No. 61/580,880, filed on Dec. 28, 2011, provisional application No. 61/568,130, filed on Dec. 7, 2011, provisional application No. 61/549,560, filed on Oct. 20, 2011, provisional application No. 61/467,209, filed on Mar. 24, 2011, provisional application No. 61/447,464, filed on Feb. 28, 2011, provisional application No. 61/447,089, filed on Feb. 27, 2011, provisional application No. 61/439,913, filed on Feb. 6, 2011, provisional application No. 61/414,451, filed on Nov. 17, 2010, provisional application No. 61/388,002, filed on Sep. 30, 2010, provisional application No. 61/352,166, filed on Jun. 7, 2010.

(51) Int. Cl.

| | | |
|---|---|---|
| *H04N 21/25* | (2011.01) | |
| *H04N 21/442* | (2011.01) | |
| *G06K 9/62* | (2006.01) | |
| *G06K 9/00* | (2006.01) | |
| *A61B 5/16* | (2006.01) | |
| *G06Q 30/06* | (2012.01) | |
| *A61B 5/00* | (2006.01) | |

(52) U.S. Cl.
CPC ........ *A61B 5/7267* (2013.01); *G06K 9/00302* (2013.01); *G06K 9/00845* (2013.01); *G06K 9/627* (2013.01); *G06Q 30/0631* (2013.01); *H04N 21/251* (2013.01); *H04N 21/4223* (2013.01); *H04N 21/44218* (2013.01); *H04N 21/4667* (2013.01); *A61B 2503/12* (2013.01); *A61B 2576/02* (2013.01); *G06K 2009/00328* (2013.01)

(58) Field of Classification Search
CPC ........... H04N 21/251; H04N 21/44213; H04N 21/252; H04N 21/4826; H04N 21/42203; H04N 21/2146; H04N 21/41422; A61B 5/165; G06K 9/00302; G06K 9/00711; G06Q 30/0201; G06F 16/24578; G06F 16/436
USPC ...................................................... 725/9–12
See application file for complete search history.

(56) References Cited

U.S. PATENT DOCUMENTS

| | | |
|---|---|---|
| 3,870,034 A | 3/1975 | James |
| 4,353,375 A | 10/1982 | Colburn et al. |
| 4,448,203 A | 5/1984 | Williamson et al. |
| 4,794,533 A | 12/1988 | Cohen |
| 4,807,642 A | 2/1989 | Brown |
| 4,817,628 A | 4/1989 | Zealear et al. |
| 4,950,069 A | 8/1990 | Hutchinson |
| 4,964,411 A | 10/1990 | Johnson et al. |
| 5,016,282 A | 5/1991 | Tomono et al. |
| 5,031,228 A | 7/1991 | Lu |
| 5,219,322 A | 6/1993 | Weathers |
| 5,247,938 A | 9/1993 | Silverstein et al. |
| 5,259,390 A | 11/1993 | Maclean |
| 5,507,291 A | 4/1996 | Stirbl et al. |
| 5,572,596 A | 11/1996 | Wildes et al. |
| 5,619,571 A | 4/1997 | Sandstorm et al. |
| 5,647,834 A | 7/1997 | Ron |
| 5,649,061 A | 7/1997 | Smyth |
| 5,663,900 A | 9/1997 | Bhandari et al. |
| 5,666,215 A | 9/1997 | Fredlund et al. |
| 5,725,472 A | 3/1998 | Weathers |
| 5,741,217 A | 4/1998 | Gero |
| 5,760,917 A | 6/1998 | Sheridan |
| 5,762,611 A | 6/1998 | Lewis et al. |
| 5,772,508 A | 6/1998 | Sugita et al. |
| 5,772,591 A | 6/1998 | Cram |
| 5,774,591 A | 6/1998 | Black et al. |
| 5,802,220 A | 9/1998 | Black et al. |
| 5,825,355 A | 10/1998 | Palmer et al. |
| 5,886,683 A | 3/1999 | Tognazzini et al. |
| 5,898,423 A | 4/1999 | Tognazzini et al. |
| 5,920,477 A | 7/1999 | Hoffberg et al. |
| 5,945,988 A | 8/1999 | Williams et al. |
| 5,959,621 A | 9/1999 | Nawaz et al. |
| 5,969,755 A | 10/1999 | Courtney |
| 5,983,129 A | 11/1999 | Cowan et al. |
| 5,987,415 A | 11/1999 | Breese et al. |
| 6,004,061 A | 12/1999 | Manico et al. |
| 6,004,312 A | 12/1999 | Finneran et al. |
| 6,008,817 A | 12/1999 | Gilmore, Jr. |
| 6,026,321 A | 2/2000 | Miyata et al. |
| 6,026,322 A | 2/2000 | Korenman et al. |
| 6,056,781 A | 5/2000 | Wassick et al. |
| 6,067,565 A | 5/2000 | Horvitz |
| 6,088,040 A | 7/2000 | Oda et al. |
| 6,091,334 A | 7/2000 | Galiana et al. |
| 6,099,319 A | 8/2000 | Zaltman et al. |
| 6,134,644 A | 10/2000 | Mayuzumi et al. |
| 6,182,098 B1 | 1/2001 | Selker |
| 6,185,534 B1 | 2/2001 | Breese et al. |
| 6,195,651 B1 | 2/2001 | Handel et al. |
| 6,212,502 B1 | 4/2001 | Ball et al. |

(56) References Cited

U.S. PATENT DOCUMENTS

| | | |
|---|---|---|
| 6,222,607 B1 | 4/2001 | Szajewski et al. |
| 6,309,342 B1 | 10/2001 | Blazey et al. |
| 6,327,580 B1 | 12/2001 | Pierce et al. |
| 6,349,290 B1 | 2/2002 | Horowitz et al. |
| 6,351,273 B1 | 2/2002 | Lemelson et al. |
| 6,437,758 B1 | 8/2002 | Nielsen et al. |
| 6,443,840 B2 | 9/2002 | Von Kohorn |
| 6,530,082 B1 | 3/2003 | Del Sesto et al. |
| 6,577,329 B1 | 6/2003 | Flickner et al. |
| 6,606,102 B1 | 8/2003 | Odom |
| 6,629,104 B1 | 9/2003 | Parulski et al. |
| 6,724,920 B1 | 4/2004 | Berenz et al. |
| 6,792,458 B1 | 9/2004 | Muret et al. |
| 6,847,376 B2 | 1/2005 | Engeldrum et al. |
| 7,003,135 B2 | 2/2006 | Hsieh et al. |
| 7,013,478 B1 | 3/2006 | Hendricks et al. |
| 7,027,621 B1 | 4/2006 | Prokoski |
| 7,110,570 B1 | 9/2006 | Berenz et al. |
| 7,113,916 B1 | 9/2006 | Hill |
| 7,120,880 B1 | 10/2006 | Dryer et al. |
| 7,197,459 B1 | 3/2007 | Harinarayan et al. |
| 7,233,684 B2 | 6/2007 | Fedorovskaya et al. |
| 7,246,081 B2 | 7/2007 | Hill |
| 7,263,474 B2 | 8/2007 | Fables et al. |
| 7,266,582 B2 | 9/2007 | Stelting |
| 7,307,636 B2 | 12/2007 | Matraszek et al. |
| 7,319,779 B1 | 1/2008 | Mummareddy et al. |
| 7,327,505 B2 | 2/2008 | Fedorovskaya et al. |
| 7,350,138 B1 | 3/2008 | Swaminathan et al. |
| 7,353,399 B2 | 4/2008 | Ooi et al. |
| 7,355,627 B2 | 4/2008 | Yamazaki et al. |
| 7,428,318 B1 | 9/2008 | Madsen et al. |
| 7,474,801 B2 | 1/2009 | Teo et al. |
| 7,496,622 B2 | 2/2009 | Brown et al. |
| 7,549,161 B2 | 6/2009 | Poo et al. |
| 7,551,755 B1 | 6/2009 | Steinberg et al. |
| 7,555,148 B1 | 6/2009 | Steinberg et al. |
| 7,558,408 B1 | 7/2009 | Steinberg et al. |
| 7,564,994 B1 | 7/2009 | Steinberg et al. |
| 7,573,439 B2 | 8/2009 | Lau et al. |
| 7,580,512 B2 | 8/2009 | Batni et al. |
| 7,584,435 B2 | 9/2009 | Bailey et al. |
| 7,587,068 B1 | 9/2009 | Steinberg et al. |
| 7,610,289 B2 | 10/2009 | Muret et al. |
| 7,620,934 B2 | 11/2009 | Falter et al. |
| 7,644,375 B1 | 1/2010 | Anderson et al. |
| 7,676,574 B2 | 3/2010 | Glommen et al. |
| 7,757,171 B1 | 7/2010 | Wong et al. |
| 7,826,657 B2 | 11/2010 | Zhang et al. |
| 7,830,570 B2 | 11/2010 | Morita et al. |
| 7,881,493 B1 | 2/2011 | Edwards et al. |
| 7,921,036 B1 | 4/2011 | Sharma |
| 8,010,458 B2 | 8/2011 | Galbreath et al. |
| 8,022,831 B1 | 9/2011 | Wood-Eyre |
| 8,046,798 B1 | 10/2011 | Schlack et al. |
| 8,219,438 B1 | 7/2012 | Moon et al. |
| 8,300,891 B2 | 10/2012 | Chen et al. |
| 8,369,608 B2 | 2/2013 | Gunaratne |
| 8,401,248 B1 | 3/2013 | Moon et al. |
| 8,442,638 B2 | 5/2013 | Libbus et al. |
| 8,522,779 B2 | 9/2013 | Lee et al. |
| 8,600,120 B2 | 12/2013 | Gonion et al. |
| 8,640,021 B2 | 1/2014 | Perez et al. |
| 8,738,523 B1 | 5/2014 | Sanchez et al. |
| 8,947,217 B2 | 2/2015 | Moussa et al. |
| 9,578,157 B1* | 2/2017 | Cansino ............... H04B 1/3822 |
| 2001/0033286 A1 | 10/2001 | Stokes et al. |
| 2001/0041021 A1 | 11/2001 | Boyle et al. |
| 2002/0007249 A1 | 1/2002 | Cranley |
| 2002/0030665 A1 | 3/2002 | Ano |
| 2002/0042557 A1 | 4/2002 | Bensen et al. |
| 2002/0054174 A1 | 5/2002 | Abbott et al. |
| 2002/0084902 A1 | 7/2002 | Zadrozny et al. |
| 2002/0171551 A1 | 11/2002 | Eshelman |
| 2002/0182574 A1 | 12/2002 | Freer |
| 2003/0035567 A1 | 2/2003 | Chang et al. |
| 2003/0037041 A1 | 2/2003 | Hertz |
| 2003/0060728 A1 | 3/2003 | Mandigo |
| 2003/0093784 A1* | 5/2003 | Dimitrova ............... H04N 7/18 725/10 |
| 2003/0182123 A1 | 9/2003 | Mitsuyoshi |
| 2003/0191682 A1 | 10/2003 | Shepard et al. |
| 2003/0191816 A1 | 10/2003 | Landress et al. |
| 2004/0098744 A1 | 5/2004 | Gutta |
| 2004/0181457 A1 | 9/2004 | Biebesheimer |
| 2005/0187437 A1 | 8/2005 | Matsugu |
| 2005/0283055 A1 | 12/2005 | Shirai et al. |
| 2005/0289582 A1* | 12/2005 | Tavares ............... H04H 60/33 725/10 |
| 2006/0011399 A1 | 1/2006 | Brockway et al. |
| 2006/0019224 A1 | 1/2006 | Behar et al. |
| 2006/0143647 A1 | 6/2006 | Bill |
| 2006/0149428 A1 | 7/2006 | Kim et al. |
| 2006/0170945 A1 | 8/2006 | Bill |
| 2006/0235753 A1 | 10/2006 | Kameyama |
| 2007/0167689 A1 | 7/2007 | Ramadas et al. |
| 2007/0173733 A1 | 7/2007 | Le et al. |
| 2007/0239787 A1 | 10/2007 | Cunningham et al. |
| 2007/0255831 A1 | 11/2007 | Hayashi et al. |
| 2007/0265507 A1 | 11/2007 | de Lemos |
| 2007/0299964 A1 | 12/2007 | Wong et al. |
| 2008/0059570 A1 | 3/2008 | Bill |
| 2008/0091512 A1 | 4/2008 | Marci et al. |
| 2008/0091515 A1 | 4/2008 | Thieberger et al. |
| 2008/0101660 A1 | 5/2008 | Seo |
| 2008/0103784 A1 | 5/2008 | Wong et al. |
| 2008/0184170 A1 | 7/2008 | Periyalwar |
| 2008/0208015 A1 | 8/2008 | Morris et al. |
| 2008/0221472 A1 | 9/2008 | Lee et al. |
| 2008/0287821 A1 | 11/2008 | Jung et al. |
| 2008/0292151 A1 | 11/2008 | Kurtz et al. |
| 2009/0002178 A1 | 1/2009 | Guday et al. |
| 2009/0006206 A1 | 1/2009 | Groe |
| 2009/0083421 A1 | 3/2009 | Glommen et al. |
| 2009/0094286 A1 | 4/2009 | Lee et al. |
| 2009/0112694 A1 | 4/2009 | Jung et al. |
| 2009/0112810 A1 | 4/2009 | Jung et al. |
| 2009/0133048 A1 | 5/2009 | Gibbs et al. |
| 2009/0144071 A1* | 6/2009 | Saito ............... G06Q 30/0281 705/346 |
| 2009/0150919 A1 | 6/2009 | Lee et al. |
| 2009/0156907 A1 | 6/2009 | Jung et al. |
| 2009/0164132 A1 | 6/2009 | Jung et al. |
| 2009/0193344 A1 | 7/2009 | Smyers |
| 2009/0209829 A1 | 8/2009 | Yanagidaira et al. |
| 2009/0210290 A1 | 8/2009 | Elliott et al. |
| 2009/0217315 A1 | 8/2009 | Malik et al. |
| 2009/0259518 A1 | 10/2009 | Harvey |
| 2009/0270170 A1 | 10/2009 | Patton |
| 2009/0271417 A1 | 10/2009 | Toebes et al. |
| 2009/0285456 A1 | 11/2009 | Moon et al. |
| 2009/0299840 A1 | 12/2009 | Smith |
| 2010/0070523 A1 | 3/2010 | Delgo et al. |
| 2010/0099955 A1 | 4/2010 | Thomas et al. |
| 2010/0134302 A1 | 6/2010 | Ahn et al. |
| 2010/0266213 A1 | 10/2010 | Hill |
| 2010/0274847 A1 | 10/2010 | Anderson et al. |
| 2010/0324437 A1 | 12/2010 | Freeman |
| 2011/0126226 A1 | 5/2011 | Makhlouf |
| 2011/0134026 A1 | 6/2011 | Kang et al. |
| 2011/0143728 A1 | 6/2011 | Holopainen et al. |
| 2011/0144971 A1 | 6/2011 | Danielson |
| 2011/0196855 A1 | 8/2011 | Wable et al. |
| 2011/0231240 A1 | 9/2011 | Schoen et al. |
| 2011/0251493 A1 | 10/2011 | Poh et al. |
| 2011/0263946 A1 | 10/2011 | el Kaliouby et al. |
| 2012/0109452 A1 | 5/2012 | Autran et al. |
| 2012/0124456 A1 | 5/2012 | Perez et al. |
| 2012/0324491 A1* | 12/2012 | Bathiche ............ H04N 21/42202 725/10 |
| 2013/0023337 A1 | 1/2013 | Bowers et al. |
| 2013/0030645 A1* | 1/2013 | Divine ............... B60K 35/00 701/36 |
| 2013/0116587 A1 | 5/2013 | Sommo et al. |

(56) References Cited

U.S. PATENT DOCUMENTS

| | | | |
|---|---|---|---|
| 2013/0197409 A1 | 8/2013 | Baxter et al. | |
| 2013/0204455 A1 | 8/2013 | Chia et al. | |
| 2013/0242064 A1* | 9/2013 | Herdy | H04N 21/42203 348/51 |
| 2014/0171752 A1 | 6/2014 | Park et al. | |
| 2014/0172910 A1 | 6/2014 | Jung et al. | |
| 2014/0218187 A1 | 8/2014 | Chun et al. | |
| 2014/0298364 A1* | 10/2014 | Stepanov | H04N 21/4758 725/10 |
| 2015/0135225 A1 | 5/2015 | Bayer et al. | |
| 2015/0258995 A1 | 9/2015 | Essers et al. | |
| 2016/0104486 A1 | 4/2016 | Penilla et al. | |
| 2017/0003784 A1 | 1/2017 | Garg et al. | |

FOREIGN PATENT DOCUMENTS

| | | |
|---|---|---|
| KR | 10-2008-0016303 A | 2/2008 |
| KR | 1020100048688 A | 5/2010 |
| WO | WO 2011/045422 A1 | 4/2011 |

OTHER PUBLICATIONS

International Search Report dated Nov. 14, 2011 for PCT/US2011/39282.

International Search Report dated Apr. 16, 2012 for PCT/US2011/054125.

International Search Report dated May 24, 2012 for PCT/US2011/060900.

Xiaoyu Wang, An HOG-LBP human detector with partial occlusion handling, Sep. 29, 2009, IEEE 12th International Conference on Computer Vision, Kyoto, Japan.

Zhihong Zeng, A Survey of Affect Recognition Methods: Audio, Visual, and Spontaneous Expressions, Jan. 2009, IEEE Transactions on Pattern Analysis and Machine Intelligence, vol. 31, No. 1.

Nicholas R. Howe and Amanda Ricketson, Improving the Boosted Correlogram, 2004, Lecture Notes in Computer Science, ISSN 0302-9743, Springer-Verlag, Germany.

Xuming He, et al, Learning and Incorporating Top-Down Cues in Image Segmentation, 2006, Lecture Notes in Computer Science, ISBN 978-3-540-33832-1, Springer-Verlag, Germany.

Ross Eaton, et al, Rapid Training of Image Classifiers through Adaptive, Multi-frame Sampling Methods, Oct. 2008, IEEE 37th Applied Imagery Pattern Recognition Workshop, Washington DC.

Verkruysse, Wim, Lars O. Svaasand, and J. Stuart Nelson. "Remote plethysmographic imaging using ambient light." Optics express 16.26 (2008): 21434-21445.

Albiol, Alberto, et al. "Face recognition using HOG-EBGM." Pattern Recognition Letters 29.10 (2008): 1537-1543.

Fasel, B. (Aug. 2002). Robust face analysis using convolutional neural networks. In Object recognition supported by user interaction for service robots (vol. 2, pp. 40-43). IEEE.

Matsugu, M., Mori, K., Mitari, Y., & Kaneda, Y. (2003). Subject independent facial expression recognition with robust face detection using a convolutional neural network. Neural Networks, 16(5-6), 555-559.

* cited by examiner

VEHICLE VIDEO RECOMMENDATION VIA AFFECT

RELATED APPLICATIONS

This application claims the benefit of U.S. provisional patent applications "Vehicle Manipulation Using Cognitive State Engineering" Ser. No. 62/679,825, filed Jun. 3, 2018, and "Image Analysis for Human Perception Artificial Intelligence" Ser. No. 62/827,088, filed Mar. 31, 2019.

This application is a continuation-in-part of U.S. patent application "Video Recommendation Via Affect" Ser. No. 15/357,585, filed Nov. 21, 2016, which is a continuation-in-part of U.S. patent application "Video Recommendation Using Affect" Ser. No. 14/821,896, filed Aug. 10, 2015, which is a continuation-in-part of U.S. patent application "Video Recommendation Based on Affect" Ser. No. 13/406,068, filed Feb. 27, 2012, which claims the benefit of U.S. provisional patent applications "Recommendation and Visualization of Affect Responses to Videos" Ser. No. 61/447,089, filed Feb. 27, 2011, "Video Ranking Based on Affect" Ser. No. 61/447,464, filed Feb. 28, 2011, "Baseline Face Analysis" Ser. No. 61/467,209, filed Mar. 24, 2011, "Mental State Analysis of Voters" Ser. No. 61/549,560, filed Oct. 20, 2011, "Mental State Evaluation Learning for Advertising" Ser. No. 61/568,130, filed Dec. 7, 2011, "Affect Based Concept Testing" Ser. No. 61/580,880, filed Dec. 28, 2011, and "Affect Based Evaluation of Advertisement Effectiveness" Ser. No. 61/581,913, filed Dec. 30, 2011.

The application "Video Recommendation Via Affect" Ser. No 15/357,585, filed Nov. 21, 2016 is also a continuation-in-part of U.S. patent application "Mental State Event Signature Usage" Ser. No. 15/262,197, filed Sep. 12, 2016, which claims the benefit of U.S. provisional patent applications "Mental State Event Signature Usage" Ser. No. 62/217,872, filed Sep. 12, 2015, "Image Analysis In Support of Robotic Manipulation" Ser. No. 62/222,518, filed Sep. 23, 2015, "Analysis of Image Content with Associated Manipulation of Expression Presentation" Ser. No. 62/265,937, filed Dec. 10, 2015, "Image Analysis Using Sub-Sectional Component Evaluation To Augment Classifier Usage" Ser. No. 62/273,896, filed Dec. 31, 2015, "Analytics for Live Streaming Based on Image Analysis within a Shared Digital Environment" Ser. No. 62/301,558, filed Feb. 29, 2016, and "Deep Convolutional Neural Network Analysis of Images for Mental States" Ser. No. 62/370,421, filed Aug. 3, 2016. The patent application "Mental State Event Signature Usage" Ser. No. 15/262,197, filed Sep. 12, 2016, is also a continuation-in-part of U.S. patent application "Mental State Event Definition Generation" Ser. No. 14/796,419, filed Jul. 10, 2015, which claims the benefit of U.S. provisional patent applications "Mental State Event Definition Generation" Ser. No. 62/023,800, filed Jul. 11, 2014, "Facial Tracking with Classifiers" Ser. No. 62/047,508, filed Sep. 8, 2014, "Semiconductor Based Mental State Analysis" Ser. No. 62/082,579, filed Nov. 20, 2014, and "Viewership Analysis Based On Facial Evaluation" Ser. No. 62/128,974, filed Mar. 5, 2015. The patent application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The patent application "Mental State Event Definition Generation" Ser. No. 14/796,419, filed Jul. 10, 2015 is also a continuation-in-part of U.S. patent application "Mental State Analysis Using an Application Programming Interface" Ser. No. 14/460,915, Aug. 15, 2014, which claims the benefit of U.S. provisional patent applications "Application Programming Interface for Mental State Analysis" Ser. No. 61/867,007, filed Aug. 16, 2013, "Mental State Analysis Using an Application Programming Interface" Ser. No. 61/924,252, filed Jan. 7, 2014, "Heart Rate Variability Evaluation for Mental State Analysis" Ser. No. 61/916,190, filed Dec. 14, 2013, "Mental State Analysis for Norm Generation" Ser. No. 61/927,481, filed Jan. 15, 2014, "Expression Analysis in Response to Mental State Express Request" Ser. No. 61/953,878, filed Mar. 16, 2014, "Background Analysis of Mental State Expressions" Ser. No. 61/972,314, filed Mar. 30, 2014, and "Mental State Event Definition Generation" Ser. No. 62/023,800, filed Jul. 11, 2014. The patent application "Mental State Analysis Using an Application Programming Interface" Ser. No. 14/460,915, Aug. 15, 2014 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011. Each of the foregoing applications is hereby incorporated by reference in its entirety.

FIELD OF INVENTION

This application relates generally to facial data-based video recommendations and more particularly to generating vehicle video recommendations via affect.

BACKGROUND

People spend seemingly endless amounts of time getting to, waiting for, and traveling in vehicles. The purposes of travel include daily commuting to and from the office, taking the kids to softball practice and piano lessons, taking the pets to the veterinary, shopping, traveling, sightseeing, and the many other common activities that require transportation. People use a variety of vehicles to meet their transportation needs, depending on where they live. Individuals use public transportation networks, such as buses, trains, and airplanes; ride-sharing services such as Uber™ and Lyft™; personal vehicles such as cars and motorcycles; and even unmotorized vehicles such as bicycles and scooters; to travel among various destinations. Traveling is time consuming at best, and at worst, boring, frustrating, irritating, and stressful.

Rush hour traffic; accidents; inexperienced, incompetent, or dangerous vehicle operators; and poorly maintained roads, among other inevitabilities, also complicate vehicular transportation. The difficulties of transportation are further exacerbated by operating an unfamiliar vehicle, driving in an unfamiliar city, navigating an unfamiliar public transportation network, and even having to remember to drive on the opposite side of the road. These transportation challenges can have catastrophic consequences. Irritated vehicle operators have experienced road rage and other antisocial behaviors, while bored, sleepy, tired, impaired, distracted, or inattentive drivers have caused vehicular accidents and injury to themselves, pedestrians, bicyclists, animals, and property.

Transportation generally, and urban transportation particularly, present many design, fiscal, and management problems which directly impact travelers. Heavily congested surface roads and highways, and woefully insufficient parking, directly influence the cognitive or mental states, moods, and emotions of travelers. The congested roadways cause longer, more dangerous commutes, and inadequate parking increases the amount of time wasted looking for a place to leave a vehicle. Public transportation, if even an option, presents challenges of its own, such as overfilled buses, trains, and subways during commuting hours, and underused routes due to lack of interest, poor planning, and other factors. The increased use of bicycles presents its own additional challenges when vehicles and bicycles share overfilled roadways that were not properly designed for multi-use scenarios. Although vehicle operators and passengers may not be directly involved in the management and financing of transportation systems, they directly experience and suffer from the frustration and annoyance of using the transportation systems, all while carrying the tax burden of paying to build, operate, maintain, and upgrade them.

SUMMARY

In disclosed techniques, vehicle media presentation selection recommendation uses facial data, audio data, and other cognitive state data collected of a vehicle occupant. The vehicle media presentation that can be recommended can include video selections or audio selections, where the video or audio selections may be recommended from a library, a stream, a curated collection, and so on. A first media presentation is played on a video client to a vehicle occupant. The vehicle can be a first vehicle, a second vehicle, a third vehicle, a public transportation vehicle, etc. The video client can be an app on a personal electronic device such as a smartphone, PDA, or tablet. The video client can include an extension within a web-enabled interface. The first media presentation includes one of a YouTube™ video, a Vimeo™ video, and a Netflix™ video. Cognitive state data for the vehicle occupant is captured. The cognitive state data includes video facial data from the vehicle occupant during the first media presentation playing. The video facial data can include data collected on various wavelengths of light such as near-infrared wavelengths less than 950 nm. An analysis server is used to rank the first media presentation relative to another media presentation. The ranking of the first media presentation is based on the cognitive state data which was captured for the vehicle occupant. The ranking is for the vehicle occupant. The ranking can include "similar" or "dissimilar", a numerical value, a scale, a threshold, etc. The analysis server is used to correlate the cognitive state data which was captured for the vehicle occupant to cognitive state data collected from other people who experienced the first media presentation. The correlating can determine whether the vehicle occupant experienced one or more cognitive states similar to or different from other people. One or more further media presentation selections are recommended to the vehicle occupant, based on the ranking and the correlating. The further media presentation selections can be similar to or dissimilar to recommendations made to the other people. The further media presentation selection can include a first socially shared live-stream video, a second socially shared live-stream video, and so on. A recommendation can be made to the vehicle occupant for changing from the first socially shared live-stream video to the second socially shared live-stream video.

In embodiments, a computer-implemented method for affect-based recommendations comprises: playing, on a video client, a first media presentation to a vehicle occupant; capturing cognitive state data for the vehicle occupant, wherein the cognitive state data includes video facial data from the vehicle occupant during the first media presentation playing; ranking, on an analysis server, the first media presentation relative to another media presentation based on the cognitive state data which was captured for the vehicle occupant, wherein the ranking is for the vehicle occupant; correlating, on the analysis server, the cognitive state data which was captured for the vehicle occupant to cognitive state data collected from other people who experienced the first media presentation; and recommending to the vehicle occupant one or more further media presentation selections, based on the ranking and the correlating.

In some embodiments, the method further includes obtaining audio information from the occupant of the vehicle and augmenting the correlating based on the audio information. The audio information can include speech, non-speech vocalizations, and so on. The non-speech vocalizations can include grunts, yelps, squeals, snoring, sighs, laughter, filled pauses, unfilled pauses, or yawns. Further embodiments include obtaining physiological information from the occupant of the vehicle and augmenting the correlating based on the physiological information. The physiological information can include heart rate, heart rate variability, respiration rate, skin conductivity, and so on. The occupant of the vehicle can be a driver or operator of the vehicle or a passenger within the vehicle. The vehicle in which the individual is traveling can be an autonomous vehicle or a semi-autonomous vehicle.

The cognitive state data can be captured from multiple people and can further comprise aggregating the cognitive state data from the multiple people. The method can further comprise ranking the first media presentation relative to another media presentation based on the cognitive state data which was aggregated from the multiple people. The cognitive state data can include one of a group consisting of physiological data, facial data, and actigraphy data. The facial data can include information on one or more of a group consisting of facial expressions, action units, head gestures, smiles, brow furrows, squints, lowered eyebrows, raised eyebrows, smirks, and attention. The physiological data can include one or more of electrodermal activity, heart rate, heart rate variability, skin temperature, and respiration. The method can further comprise inferring of cognitive states based on the cognitive state data which was collected. The cognitive states can include one of a group consisting of frustration, confusion, disappointment, hesitation, cognitive overload, focusing, being engaged, attending, boredom, exploration, confidence, trust, delight, valence, skepticism, and satisfaction. The method can further comprise matching a first event signature, from the plurality of cognitive state event temporal signatures, against the cognitive state data that was captured. The first media presentation can be played on a mobile device and can further comprise the recording of facial images with the mobile device as part of the capturing of the cognitive state data.

Various features, aspects, and advantages of numerous embodiments will become more apparent from the following description.

BRIEF DESCRIPTION OF THE DRAWINGS

The following detailed description of certain embodiments may be understood by reference to the following figures wherein.

DETAILED DESCRIPTION

Figure 1:
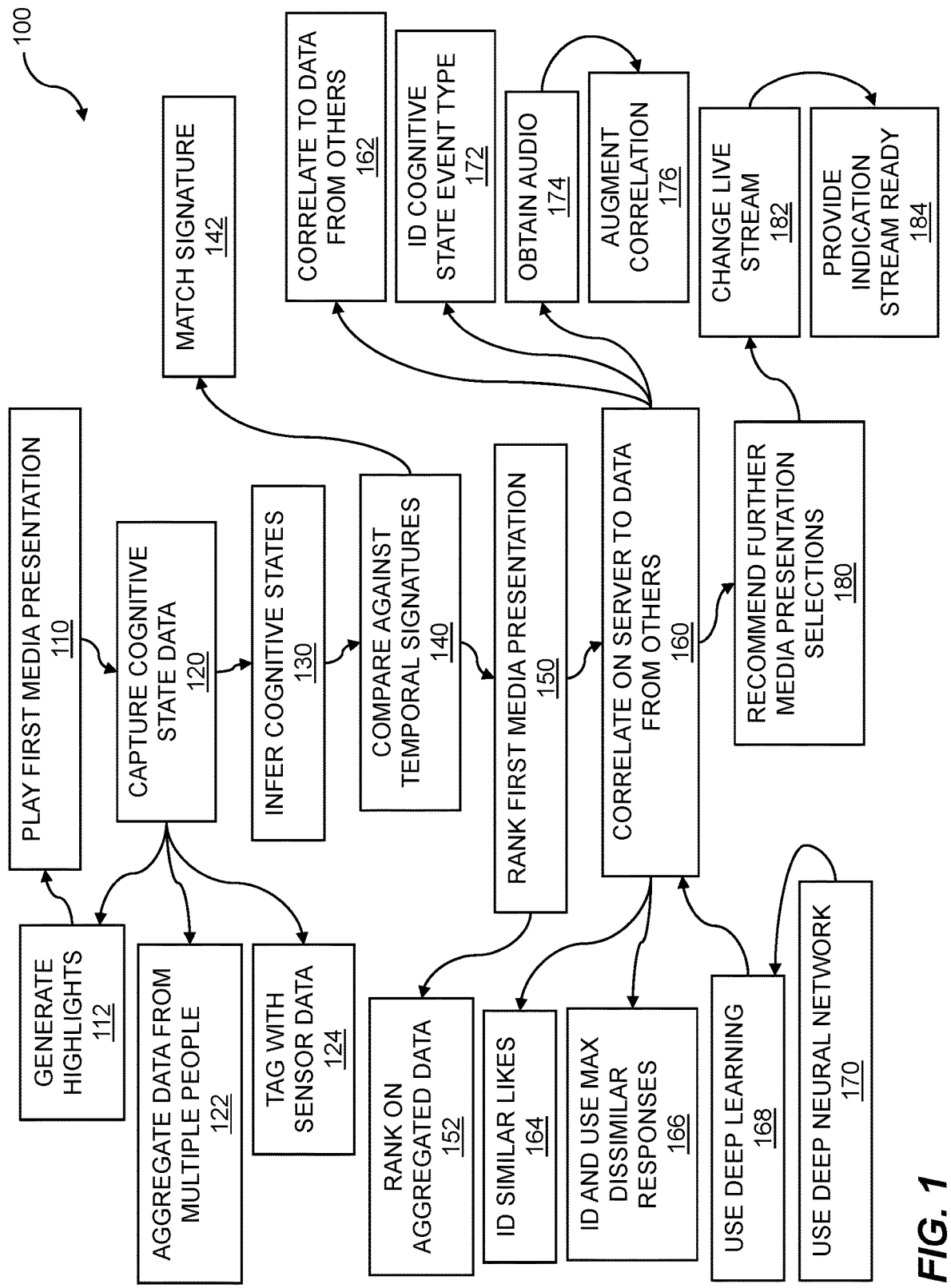
FIG. 1 is a flow diagram for vehicle video recommendation via affect.

Individuals can choose the type or types of environments in which they want to live. These individuals can reside in areas as diverse as densely populated cities or sparsely populated plains or mountains. Whether those individuals live in urban, suburban, or rural areas, they spend hundreds or more hours per year traveling in vehicles. The hours that individuals spend in vehicles are consumed by commuting to and from work, running errands, meeting appointments, traveling, etc. The vehicles that are most frequently used for travel include public, private, or commercial vehicles, such as buses, trains, airplanes, automobiles, ride share vehicles, and so on. As an individual is traveling within or atop a vehicle, that individual can experience a wide range of cognitive states, including happy or sad, angry or calm, anxious or bored, etc. The type and range of cognitive states can be determined by capturing and analyzing cognitive state data from the individual as the individual observes a media presentation that is playing within a vehicle. The cognitive state data can include image data, facial data, audio data, voice data, speech data, non-speech vocalizations, physiological data, actigraphic data, and the like. The cognitive state data can be used to rank the media presentation relative to other media presentations. The cognitive state data further can be correlated to cognitive state data collected from other people who experienced the same media presentation. The ranking and the correlating can be used to recommend one or more further media presentation selections to the vehicle occupant.

In disclosed techniques, affect-based recommendations are used for vehicle video recommendation. Vehicle video recommendations can include recommending a media presentation, one or more further media presentation selections, a socially shared live-stream video, an audio selection, and so on. The vehicle video recommendations can be performed for a variety of purposes including setting or adjusting the cognitive state or states of one or more vehicle occupants. The cognitive state or states can be based on those states of a single vehicle occupant, aggregated cognitive state or states of multiple occupants of the vehicle, and so on. A first media presentation is played on a video client to a vehicle occupant. The video client can include an app on a personal electronic device, an extension installed within a web browser, and so on. Cognitive state data for the vehicle occupant is captured, where the cognitive state data includes video facial data from the vehicle occupant during the first media presentation playing. The cognitive state data can further include audio data, physiological data, actigraphic data, etc. The video data can be collected using one or more imaging devices such as cameras, where the cameras can include a video camera, a still camera, a camera array, a plenoptic camera, a web-enabled camera, a visible light camera, a near-infrared (NIR) camera, a heat camera, and so on. The audio data can be collected using a microphone, the physiological data can be collected using sensors, the movement data can be collected using an inertial measurement unit (IMU), and so on. The cognitive states can include drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. An analysis server is used to rank the first media presentation relative to another media presentation based on the cognitive state data which was captured for the vehicle occupant, where the ranking is for the vehicle occupant. The analysis server can include a personal electronic device within the vehicle, a processor within the vehicle, a processor located beyond the vehicle, etc. The analysis server is used to correlate the cognitive state data which was captured for the vehicle occupant to cognitive state data collected from other people who experienced the first media presentation. The correlating can include determining similar cognitive states or dissimilar cognitive states to those cognitive states experienced by the other people. One or more further media presentation selections are recommended to the vehicle occupant, based on the ranking and the correlating.

FIG. 1 is a flow diagram for vehicle video recommendation via affect. Vehicle video recommendations such as media presentation selections are ranked and correlated based on cognitive state data captured from a vehicle occupant to whom a first media presentation is played. The media presentation can include a video, a video clip, a news or sports presentation, a political message, and so on. The captured cognitive state data includes video facial data. An analysis server is used to rank the first media presentation for the vehicle occupant, and to correlate cognitive state data for the vehicle occupant to cognitive state data collected from other people who experienced the first media presentation. One or more further media presentations are recommended to the vehicle occupant based on the ranking and the correlating.

The flow 100 includes playing, on a video client, a first media presentation 110 to a vehicle occupant. The first media presentation can be selected by the vehicle occupant, by a system which is automating the collection of affect data on numerous videos, and so on. The media presentation can include one of a YouTube™ video, a Vimeo™ video, a Netflix™ video, and the like. The video client on which the first media presentation is played can include an app on a personal electronic device such as a smartphone, a PDA, a tablet, a laptop computer, etc. The video client can include a display within the vehicle, a display visible from within the vehicle, and the like. In embodiments, the first media presentation can be played on a web-enabled interface. The web-enabled interface can include a video player extension to a web browser. The first media presentation can include video from further sources including social media sources. In embodiments, the first media presentation can include a first socially shared live-stream video. The socially shared live-stream video can include video from social media platforms such as Facebook Live™. In embodiments, the first media presentation includes one of a group consisting of a movie, a television show, a web series, a webisode, a video, a video clip, an electronic game, an e-book, and an e-magazine. The flow 100 further includes generating highlights for the first socially shared live-stream video 112. The highlights that are generated can be based on events within the video stream, the vehicle occupant, other individuals who may view the video stream, etc. Discussed shortly, the highlights for the first socially shared live-stream video can be based on cognitive state data that can be captured. Other information such as meta-information can be included with the highlights.

The flow 100 includes capturing cognitive state data 120 for the vehicle occupant. Various types of cognitive state data can be collected. The cognitive state data can include video facial data from the vehicle occupant during the first media presentation playing. The cognitive state data can be collected using one or more cameras, sensors such as inertial measurement units (IMUs), etc. The video facial data can be based on various light spectra. In embodiments, the video facial data can include near-infrared content (NIR). The near-infrared content can be based on a wavelength of light or a range of wavelengths of light. In embodiments, the wavelength of the near-infrared content is less than 950 nm. Other electromagnetic wavelengths may also be used. The capturing cognitive state data can include capturing cognitive state data from the vehicle occupant as the vehicle occupant is viewing a first socially shared live-stream video. In embodiments, the cognitive state data that was captured for the first socially shared live-stream video can be analyzed substantially in real time.

In embodiments, the cognitive state data further includes physiological data or actigraphy data. Various types of physiological data, for example, can be collected. In embodiments, the physiological data can include one or more of electrodermal activity, heart rate, heart rate variability, skin temperature, respiration, and the like. The cognitive state data can include video facial data from the vehicle occupant during the first media presentation playing. The video facial data can include facial regions, facial landmarks, and so on. The video may include other regions of the body of the vehicle occupant such as an upper torso. In embodiments, the video facial data can include information on one or more of a group consisting of facial expressions, action units, head gestures, smiles, squints, lowered eyebrows, raised eyebrows, smirks, and attention. The captured cognitive state data can be used to generate the highlights from the socially shared live-stream video, discussed previously. In embodiments, the first socially shared live-stream video can include an overlay with information on the cognitive state data that was captured. More than one person may occupy the vehicle, may be present in a second vehicle or an adjacent vehicle, and so on. In embodiments, the cognitive state data can be captured from multiple people. The flow 100 further includes aggregating the cognitive state data from the multiple people 122. The aggregating the cognitive state data can include aggregating video data, physiological data, actigraphic data, etc. The flow 100 further includes tagging the cognitive state with sensor data 124. The sensor data can be related to data collected from sensors within the vehicle, adjacent to the vehicle, etc. In embodiments, the sensor data can include one or more of vehicle interior temperature, vehicle exterior temperature, time of day, day of week, season, level of daylight, weather conditions, road conditions, traffic conditions, headlight activation, windshield wiper activation, vehicle settings, entertainment center selection, or entertainment center volume.

The flow 100 further includes inferring cognitive states 130, based on both the cognitive state data which was captured and the analysis of the video facial data. One or more cognitive states can be inferred from the cognitive state data. In embodiments, the cognitive state data can include one or more of drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. The cognitive states that can be inferred can be based on one or more codings or action units from the facial coding action system (FACS). In embodiments, the analysis of the video facial data is for at least brow furrows. Other analysis can include analysis for inner brow raisers, outer brow raisers, nose wrinklers, and so on. The inferring can be performed on an analysis server.

The flow 100 further can include comparing, on the analysis server, the cognitive state data that was captured for the vehicle occupant against a plurality of cognitive state event temporal signatures 140. A temporal signature can include an onset, a duration, a decay, and so on. In embodiments, the cognitive state event temporal signatures can include a shape of an intensity transition. A shape with a steep slope can indicate a rapid onset or decay, while an intensity can indicate a strength of the signature. The intensity can be indicated with a letter A through E, where A indicates a trace, and E indicates maximum. The flow 100 further includes matching a first cognitive state event signature 142, from the plurality of cognitive state event temporal signatures, against the cognitive state data that was captured. The matching the first cognitive state event signature can be used to determine whether the viewer of the first media presentation experienced cognitive states similar to those cognitive states experienced by other individuals who viewed the first media presentation.

The flow 100 includes ranking, on an analysis server, the first media presentation 150 relative to another media presentation. The ranking of the first media presentation to another media presentation is based on the cognitive state data which was captured for the vehicle occupant. The ranking of the first media presentation is for the vehicle occupant. The ranking can be based on a numerical scale, can include a relative comparison such as similar or dissimilar, and so on. The ranking can be based on first media presentation relative to other media presentations viewed by the vehicle occupant. The other media presentations can include media presentations played to the vehicle occupant at previous times, media presentations played to the vehicle occupant when she or he was present in another vehicle, and so on. In embodiments, the ranking can be based on anticipated preferences for the vehicle occupant. The anticipated preferences for the vehicle occupant can be based on an occupant ID or profile, on previous occurrences of the occupant within the vehicle, on a time of day or day of week, on demographic data relating to the vehicle occupant, and so on. The flow 100 further includes ranking the first media presentation relative to another media presentation based on the cognitive state data which was aggregated 152 from the multiple people. The ranking can be based on a "most liked" media presentation, a "least liked" media presentation, a numerical score, etc.

The flow 100 includes correlating, on the analysis server, the cognitive state data which was captured for the vehicle occupant to cognitive state data collected from other people 160 who experienced the first media presentation. The correlating can be based on a percentage, a threshold, a range, a qualifier such as similar or dissimilar, and so on. The correlating can be based on using one or more classifiers. Further embodiments include correlating the cognitive state data which was captured for the vehicle occupant to cognitive state data collected from other people 162 who experienced the first media presentation. The correlating can be performed on a personal electronic device associated with the vehicle occupant, such as a smartphone, PDA, or tablet. The correlating can be performed on a processor located within the vehicle, adjacent to the vehicle, remote from the vehicle, etc. The correlating can be performed for a variety of purposes. In embodiments, the correlating can be based on identifying similar likes 164. The similar likes can be based on a temporal signature associated with a video media presentation. The similar likes can be based on the likes of other people within a demographic group similar to a demographic group of the vehicle occupant. The similar likes can be based on content such as cute puppies, kittens on keyboards, amusing pratfalls, etc. The similar likes can be based on other content such as political messages, sporting contests, and the like. In further embodiments, the correlating can be based on identifying and using maximally dissimilar responses 166 during part of the correlating. Maximally dissimilar responses might include the vehicle occupant frowning or scowling at a point in the video where other people were smiling or laughing. The correlating can include analyzing the cognitive state data, clustering the cognitive state data, etc. Further embodiments include analyzing the cognitive state data to produce cognitive state information.

In the flow 100, the correlating is performed using deep learning 168. Described throughout, deep learning can be used to train the correlating to converge faster, to better identify similar likes or maximally dissimilar responses, and so on. Various techniques can be used to perform the deep learning. In embodiments, the deep learning is performed using a deep neural network 170. A deep neural network can comprise a plurality of layers such as input layers, hidden layers, bottleneck layers, activation layers, output layers, etc. In embodiments, the learning is performed using a convolutional neural network. Other neural network techniques can also be used. In further embodiments, the learning is performed using a recurrent neural network. The flow 100 includes identifying a cognitive state event type 172 based on the correlating. A cognitive state event type can include an occurrence of a cognitive state such as drowsiness, sadness, stress, happiness, doubt, satisfaction, and the like. The flow 100 further includes obtaining audio information 174 from the occupant of the vehicle. The audio information can be obtained using a microphone, an audio transducer, or any other audio detection component. The microphone, for example, can be coupled to a personal electronic device or other electronic device within the vehicle. The audio information can include speech. The speech can be generated by the occupant of the vehicle, another occupant of the vehicle, an audio system within the vehicle, and so on. The audio information can include road noise or other sounds from beyond the vehicle.

In other embodiments, the audio information includes non-speech vocalizations. The non-speech vocalizations can include non-speech vocalizations emanating from the vehicle occupant, from another occupant within the vehicle, etc. In embodiments, the non-speech vocalizations include grunts, yelps, squeals, snoring, sighs, laughter, filled pauses, unfilled pauses, or yawns. The flow 100 includes augmenting the correlating 176 based on the audio information. The augmenting the correlating can include synchronizing speech, non-speech vocalizations, etc., with other cognitive state data such as video facial data. In a usage example, the augmenting the correlating can include determining that a laugh can be detected contemporaneously to the detection of a smile. The correlating can be further adjusted or modified based on the wavelength or wavelengths of light used when capturing the cognitive state data. In further embodiments, the correlating is modified, based on the near-infrared content of the video facial data. The near-infrared content can be based on one or more wavelengths. In embodiments, the wavelength of the near-infrared is less than 950 nm.

The flow 100 includes recommending to the vehicle occupant one or more further media presentation selections 180, based on the ranking and the correlating. The recommending can occur before an individual enters a vehicle, while the individual is within the vehicle, while the individual is planning to travel within the vehicle, and so on. In embodiments, the recommending occurs while the vehicle occupant occupies the vehicle. The recommending can include one or more video media presentations, settings within the vehicle, and the like. In other embodiments, the recommending can occur after the vehicle occupant leaves the vehicle. The one or more further media presentation selections can include a variety of video or other content. In embodiments, the one or more further media presentation selections can include one of a group consisting of a movie, a television show, a web series, a webisode, a video, a video clip, an electronic game, an e-book, and an e-magazine. The recommending can include recommending a video media presentation similar to a video media presentation that caused the vehicle occupant to smile, to be engaged, to laugh, and so on. The recommending can include recommending a video media presentation dissimilar to a video media presentation that caused the vehicle occupant to frown, to be bored, to yawn, and the like. The recommending can be based on a cognitive state event signature.

In embodiments, the recommending the one or more further media presentation selections can be further based on the matching of the first cognitive state event signature. The recommending can also be based on a cognitive state event type. In embodiments, the recommending of the one or more further media presentation selections can be further based on the cognitive state event type. Recall that the first media presentation can include a first socially shared live-stream video. A socially shared live-stream video can be shared with the vehicle occupant, other occupants of the vehicle, and so on. In embodiments, the first socially shared live-stream video is broadcast to a plurality of people. Other socially shared live-stream video may also be available. Further embodiments include a recommendation for changing 182 from the first socially shared live-stream video to the second socially shared live-stream video. Changing from the first socially shared live-stream video to the second socially shared live-stream video may cause a time delay. The time delay may be due to network delay, buffering of the video, and so on. Further embodiments include providing an indication to the vehicle occupant that the second socially shared live-stream video is ready 184 to be joined. The indication to the vehicle occupant that the second socially shared live-stream video is ready to be joined can include a message, an icon, an emoji, and the like. The indication to the vehicle occupant can include auto-starting the second socially shared live-stream video.

Various steps in the flow 100 may be changed in order, repeated, omitted, or the like without departing from the disclosed inventive concepts. Various embodiments of the flow 100 may be included in a computer program product embodied in a non-transitory computer readable medium that includes code executable by one or more processors. The flow 100 can include tagging the plurality of media presentations with cognitive state information based on the cognitive state data which was captured.

Figure 2:
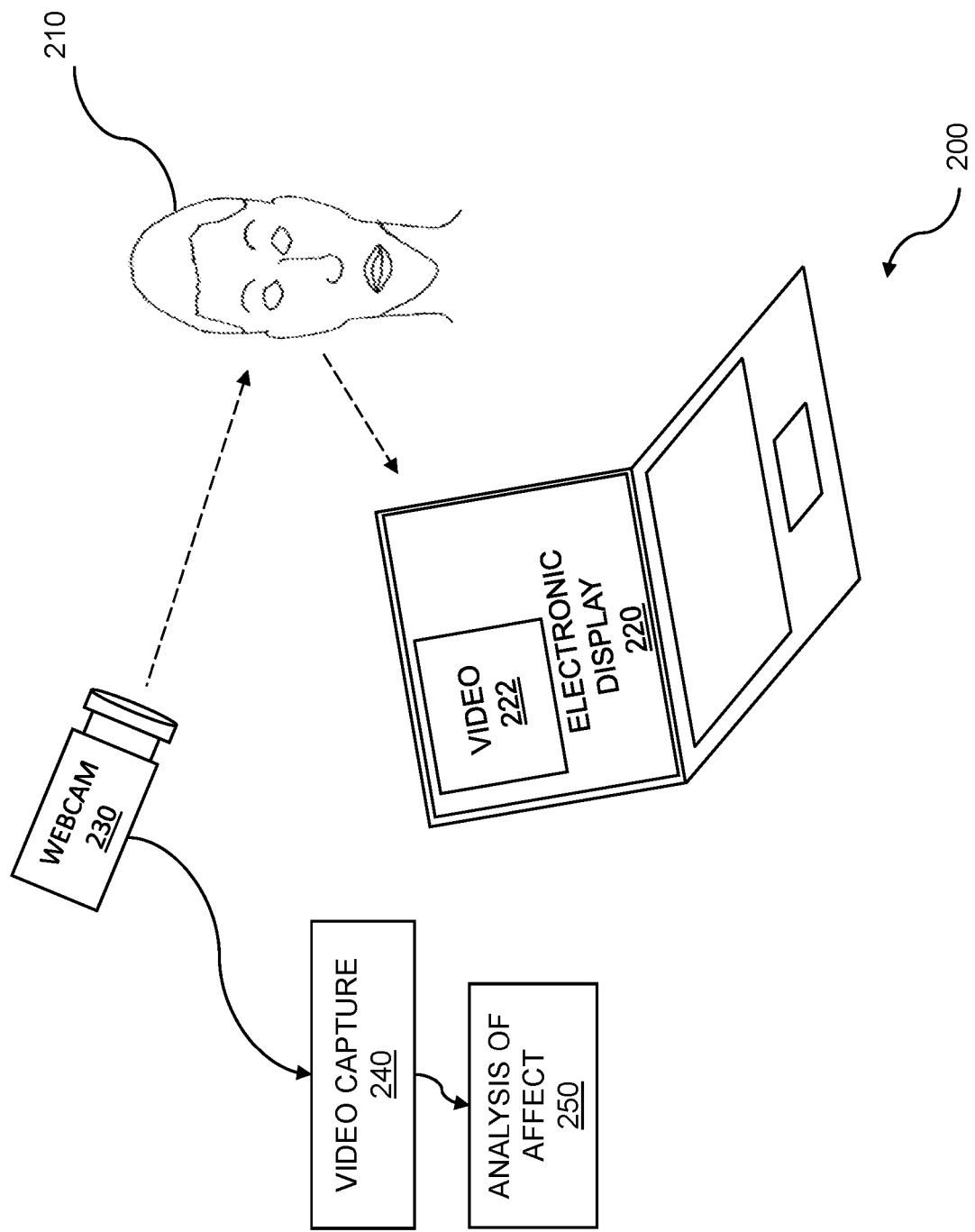
FIG. 2 is a system for capturing facial response to a video.

FIG. 2 is a system for capturing facial response to a video. A facial response to a video can include facial expressions such as smiles, frowns, grimaces, laughs, smirks, and so on. A facial response can be captured from an individual and can be used to infer one or more cognitive states of the individual. The individual can include an occupant of a vehicle. The facial response can be analyzed to determine affect. The facial response to a video can enable vehicle video recommendation via affect. A first media presentation is played on a video client to a vehicle occupant. Cognitive state data including video facial data for the vehicle occupant is captured during the first media presentation playing. An analysis server ranks the first media presentation relative to another media presentation based on the captured cognitive state data. The analysis server correlates the cognitive state data for the vehicle occupant to cognitive state data collected from other people who experienced the first media presentation. One or more further media presentation selections are recommended to the vehicle occupant, based on the ranking and the correlating.

A system 200 includes an electronic display 220 and a webcam 230. The system 200 captures facial response to a video 222 shown on the electronic display 220. The facial data can include both video and the collection of information relating to cognitive states. The facial data can include information on one or more of a group consisting of facial expressions, action units, head gestures, smiles, brow furrows, squints, lowered eyebrows, raised eyebrows, smirks, and attention. In some embodiments, a webcam 230 captures video of the person 210. Images of the person 210 can also be captured by a camera on a computer (such as a laptop, a netbook, a tablet, or the like), a video camera, a still camera, a cell phone camera, a mobile device camera (including, but not limited to, a forward facing camera), a thermal imager, a CCD device, a three-dimensional camera, a depth camera, and multiple webcams used to capture different views of viewers or any other type of image capture apparatus that can allow captured image data to be used by an electronic system. The capture of the facial response of the person 210 to the video 222 shown on the display 220 can include the collection of cognitive state data. The capture of the facial response of the person 210 to the video 222 shown on the display 220 can include the capture of physiological data. The physiological data can include one or more of heart rate, heart rate variability, skin temperature, respiration, and the like.

The electronic display 220 can show a video. The video 222 can be shown on any electronic display, including but not limited to, a computer display, a laptop screen, a netbook screen, a tablet computer screen, a cell phone display, a mobile device display, a remote with a display, a television, a projector, or the like. The electronic display 220 can include connections to a keyboard, mouse, joystick, touchpad, wand, motion sensor, etc. The video 222 can be displayed within a webpage, a website, a web-enabled application, or the like. The images of the person 210 can be captured by a video capture unit 240. In some embodiments, video of the person 210 is captured, while in others, a series of still images is captured.

Analysis of action units, gestures, cognitive states, and physiological data can be accomplished using the captured images of the person 210. The action units can be used to identify smiles, frowns, and other facial indicators of cognitive states. The gestures, including head gestures, can indicate interest or curiosity. For example, a head gesture of moving toward the video 222 can indicate increased interest or a desire for clarification. Based on the captured images, analysis of physiology, or affect, can be performed. Analysis of affect 250 can be performed based on the information and images which are captured. The analysis can include facial analysis and analysis of head gestures. The analysis can include evaluating physiology and evaluating one of a group consisting of heart rate, heart rate variability, respiration, perspiration, temperature, and other bodily evaluations.

Figure 3:
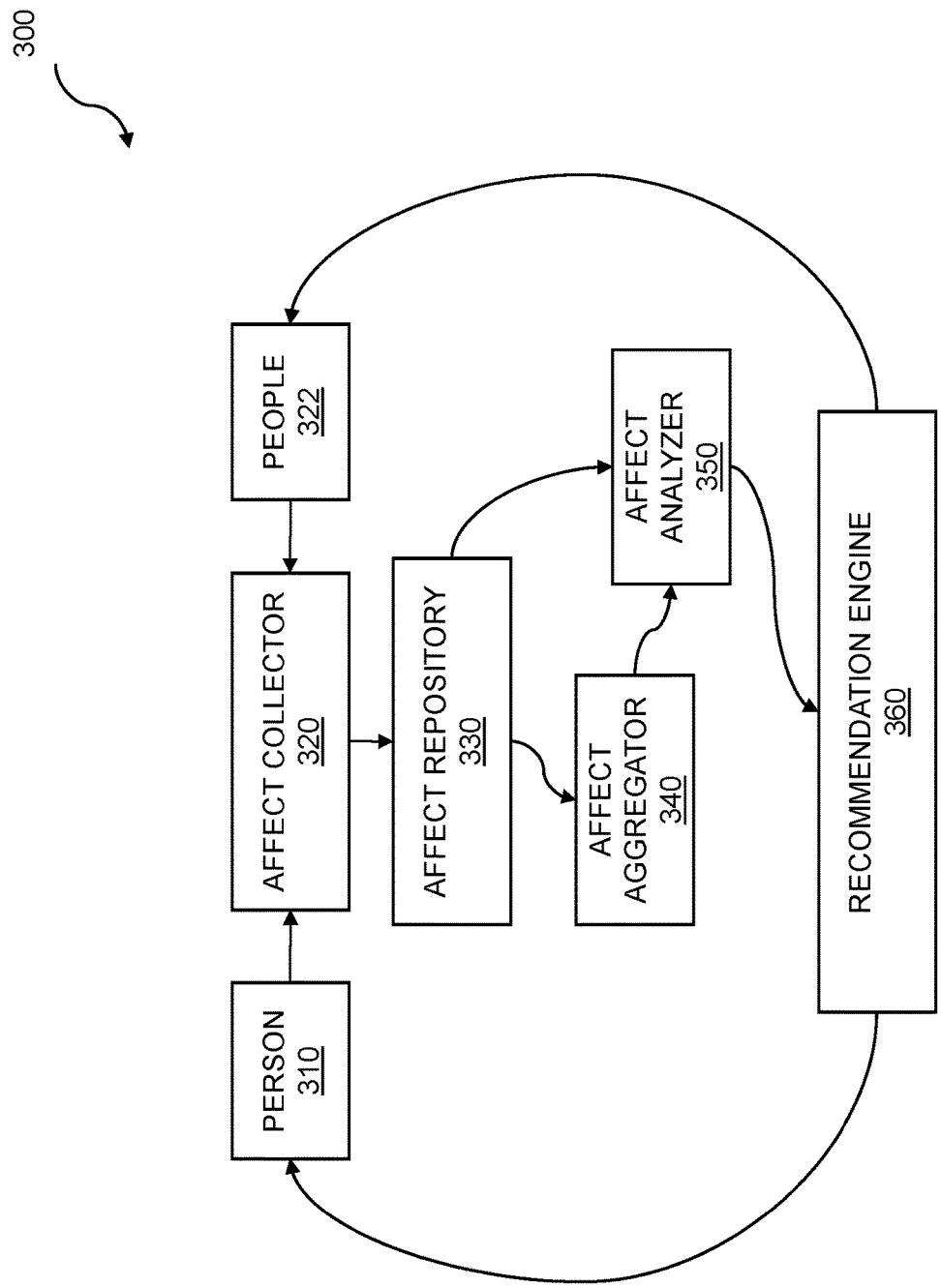
FIG. 3 is a diagram of a recommendation system.

FIG. 3 is a diagram of a recommendation system. A recommendation system can be used to make recommendations to a person for a travel route, settings such as climate settings within a vehicle, and so on. The recommendations determined by the recommendation system can be based on an individual's cognitive state, mood, emotional state, and the like. The recommendation system can enable vehicle video recommendation via affect. In the flow 300, a person 310 can view a video. While the person 310 is viewing a video, an affect collector 320 can gather affect data on the person 310. The affect collector 320 can be a webcam or another camera device. The affect collector 320 can be a biosensor attached to the person 310 in one or more locations. The affect data collected from the person 310 by the affect collector 320 can be stored in an affect repository 330. The affect repository 330 can be on a local computer or on a remote server, or it can be distributed as part of a cloud computing system.

An affect analyzer 350 can analyze the affect data collected from the person 310. The affect analyzer 350 can recognize cognitive states including information on concentration, liking, disliking, etc. The affect analyzer 350 can recognize smiles or frowns. Based on the analysis done by the affect analyzer 350, a recommendation engine 360 can recommend a video or another media presentation to the person 310. The recommending of a media presentation to an individual can be based on the cognitive state data which was aggregated. The aggregated data can be for multiple videos by an individual, or it can be for a plurality of people. The recommendation can be based on common factors with one or more videos which the person 310 watched. For example, if the person 310 smiled for each of the videos that he or she watched that featured a specific actress as the main character, then the recommendation engine 360 can recommend another video with the same actress to the person 310. In another example, if a series of sports videos is liked by the person 310, then another sports video can be recommended.

Other people 322 can view the same video as the person 310. In some embodiments, multiple videos are viewed by the person 310 and the other people 322. In embodiments, different subsets of the multiple videos are viewed by each person. The affect collector 320 can capture affect data for each of the people 322. The affect collector 320 can be a single unit such as a kiosk in a mall or a device which collects affect data for multiple people viewing a video in such a location as a conference room or a movie theater. Alternatively, the affect collector 320 can be separate devices, if, for instance, each person has their own computer, laptop, cell phone, mobile device, or the like. The affect repository 330 can retain affect data from the people on whom affect data is collected.

An affect aggregator 340 can take affect data from the affect repository 330 and correlate affect data from the person 310 with the other people 322. The affect aggregator 340 can recognize trends for the person 310 who has watched multiple videos such as movies. The affect aggregator 340 can determine correlation vectors for the person 310 and the people 322 or a subset thereof. A correlation can be made using weighted Euclidean or Mahalanobis distance evaluation between two vectors, where a vector includes an individual's affect data. There are many ways to compute distances or similarity/dissimilarity measures. Collaborative filtering or the like can be used to aid in matching affect data between or among people. In some embodiments, a comparison is made based on the same content viewed by the person 310 and by individuals from the other people 322. When one vector is at a sufficiently close distance to another person's vector, then the affect aggregator 340 will look for other content that has been smiled at or liked. This other content can be recommended by the recommendation engine 360 to the person 310 because there are assumed similarities based on the affect data which was collected.

In some embodiments, the affect aggregator 340 and the affect analyzer 350 are used to review affect data stored in the affect repository 330 and to compare affect data collected on a new video with an historical database of affect data for videos. The new video can be evaluated to determine how the video ranks against other videos. For example, the new video could be compared with a "top 100" list of videos to determine the relative number of smiles that the new video has in comparison to the "top 100" list of videos for which people smiled. In embodiments, a group of people view a new video and their affect data is collected. The affect data collected for the people can be aggregated. The aggregated affect data for the new video can then be compared to the aggregated affect data for other videos. This type of comparison could be used by developers of videos to rank and evaluate a new video which has been produced. Likewise, a buyer of advertising spots, for example, could evaluate a new video based on aggregated affect data collected from a group of people. An emotion profile for the video could be generated and then compared with a "best of breed" set of videos by network studios, advertisers, or others with similar commercial interest.

In some cases, there may be good correlation for one type of video but not for another. For instance, a good correlation can be made for drama videos but a poor one for comedy videos. Based on that information, a recommendation can be made for another drama video. Collaborative filtering can be performed to identify good possibilities for correlation, and therefore areas where videos can be recommended.

The recommendation engine 360 can make recommendations to the person 310 for whom affect data was collected. The recommendation engine 360 can make the recommendations based on the correlation between the person 310 and the other people 322. Likewise, the recommendation engine 360 can make recommendations to one or more of the people 322 based on a video that was viewed by the person 310.

Figure 4:
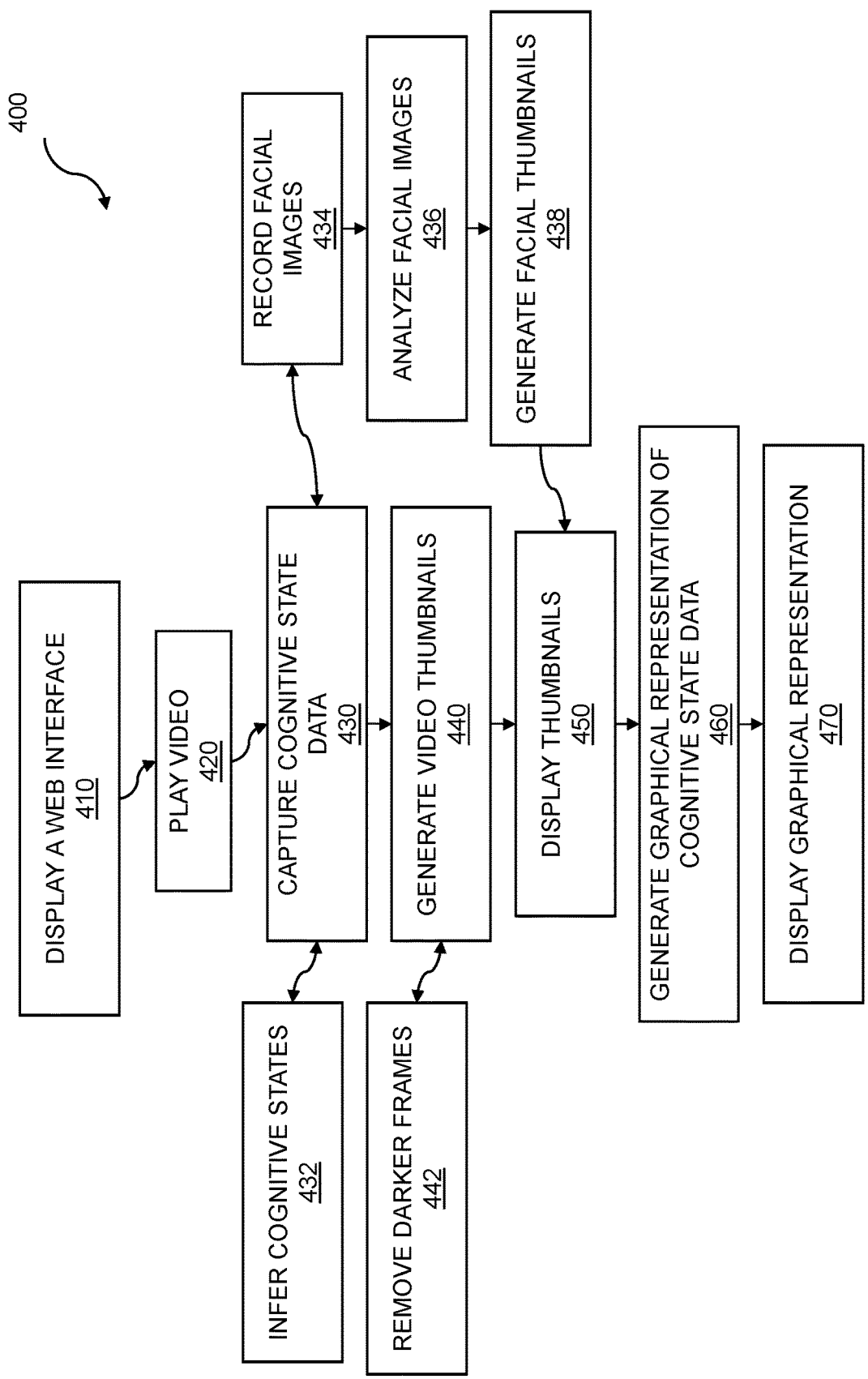
FIG. 4 is a flow diagram for displaying affect.

FIG. 4 is a flow diagram for displaying affect. Affect can be used to enable vehicle video recommendation. A first media presentation is played on a video client to a vehicle occupant. Cognitive state data for the vehicle occupant is captured, where the cognitive state data includes video facial data from the vehicle occupant during the first media presentation playing. An analysis server ranks the first media presentation relative to another media presentation based on the cognitive state data which was captured for the vehicle occupant, wherein the ranking is for the vehicle occupant. The analysis server correlates the cognitive state data which was captured for the vehicle occupant to cognitive state data collected from other people who experienced the first media presentation. One or more further media presentation selections are recommended to the vehicle occupant, based on the ranking and the correlating.

The flow 400 includes displaying a first web-enabled interface 410. The first web-enabled interface can include a web page. The flow 400 continues with playing a video 420 on the first web-enabled interface. The video can include a YouTube™ or a Vimeo™ video. The video can be one of a group consisting of a movie, a television show, a web series, a webisode, a video, a video clip, or the video can be media such as an electronic game, an advertisement, an e-book, an e-magazine, or a movie trailer. The flow 400 continues with capturing cognitive state data 430 while the video is played. The flow can further comprise inferring of cognitive states 432 based on the cognitive state data which was collected. The cognitive states can include one of a group consisting of frustration, confusion, disappointment, hesitation, cognitive overload, focusing, being engaged, attending, boredom, exploration, confidence, trust, delight, valence, skepticism, and satisfaction.

The capturing cognitive state data can further comprise recording facial images 434. The flow 400 further comprises analyzing the facial images for a facial expression 436. The facial data can include information on one or more of a group consisting of facial expressions, action units, head gestures, smiles, brow furrows, squints, lowered eyebrows, raised eyebrows, smirks, attention, and the like. The facial expressions can be used to generate facial thumbnails 438. In some embodiments, representative low-resolution images are included in the thumbnails rather than images obtained directly from a webcam or another imaging apparatus.

The flow 400 includes generating a set of thumbnails 440 for the video, which was played, where the thumbnails comprise scenes from the video and the set of thumbnails are generated automatically. The flow 400 further comprises analyzing the set of thumbnails and removing a frame 442 from the set of thumbnails based on a darkness threshold. Another frame can be used in place of the frame that was removed. The flow 400 continues with displaying the set of thumbnails 450 on a second web-enabled interface. The second web-enabled interface can include a web page. In embodiments, the thumbnails are for the video which was played.

In embodiments, an individual thumbnail is one "scene" from the video and is a static image of a specified size. Various items can be useful in the generation of thumbnails and are briefly discussed here. A composite of thumbnails or zoetrope is a horizontal array of images. A darkness threshold is used to analyze a mean value of the color of an image to determine whether it is "dark." A starting offset is a number of seconds into the video in which to begin the thumbnail generation process. A number of seconds between frames can be automatically generated or manually specified and refers to the number of seconds between the individual thumbnail images. A zoetrope width is the width of the final image and can be slightly different from the width of an individual thumbnail multiplied by the number of thumbnails. A size string can be of the form "width times height", and examples of potential size strings include dimensions of 24×24, 32×32, 40×32, etc. The size string determines the dimensions of the individual thumbnail. The individual thumbnails can be examined to determine if the image is "too dark." Some movie trailers frequently fade to black, and black or very dark frames often make for poor thumbnails. A recursive look forward and backward to find a better frame is possible. If a frame is too dark, then the recursive algorithm looks behind and forward by small amounts to see if it can find a better frame that can be found within certain recursion limits. Once a good image is found or a recursion limit is reached, the video is advanced by the appropriate number of seconds between frames to identify the next thumbnail image.

In some embodiments, the flow 400 further comprises generating a set of thumbnails for the facial images 438 which were recorded and displaying the set of thumbnails 450 for the facial images on the second web-enabled interface. One thumbnail from the set of thumbnails can be selected based on a facial expression. The one thumbnail can show an animated facial expression, an unusual facial expression, or a typical facial expression.

The flow 400 includes generating a graphical representation of the cognitive state data 460 which was captured. The graphical representation can be a line graph showing an extent of a specific cognitive state or an amount of a specific facial expression. Likewise, the graphical representation can be a more complex dashboard-type presentation. The flow 400 can continue with displaying the graphical representation 470 on the second web-enabled interface. The graphical representation can include a score representing the cognitive state data. The score can be for a specific cognitive state, such as attention, frustration, disappointment, or any other cognitive state. The score can provide a numerical representation of the cognitive state.

In some embodiments, the playing of the video is done on a mobile device and the recording of the facial images is done with the mobile device. In embodiments, the cognitive state data is captured from multiple people and is then aggregated. Various steps in the flow 400 may be changed in order, repeated, omitted, or the like without departing from the disclosed inventive concepts. Various embodiments of the flow 400 may be included in a computer program product embodied in a non-transitory computer readable medium that includes code executable by one or more processors.

Figure 5:
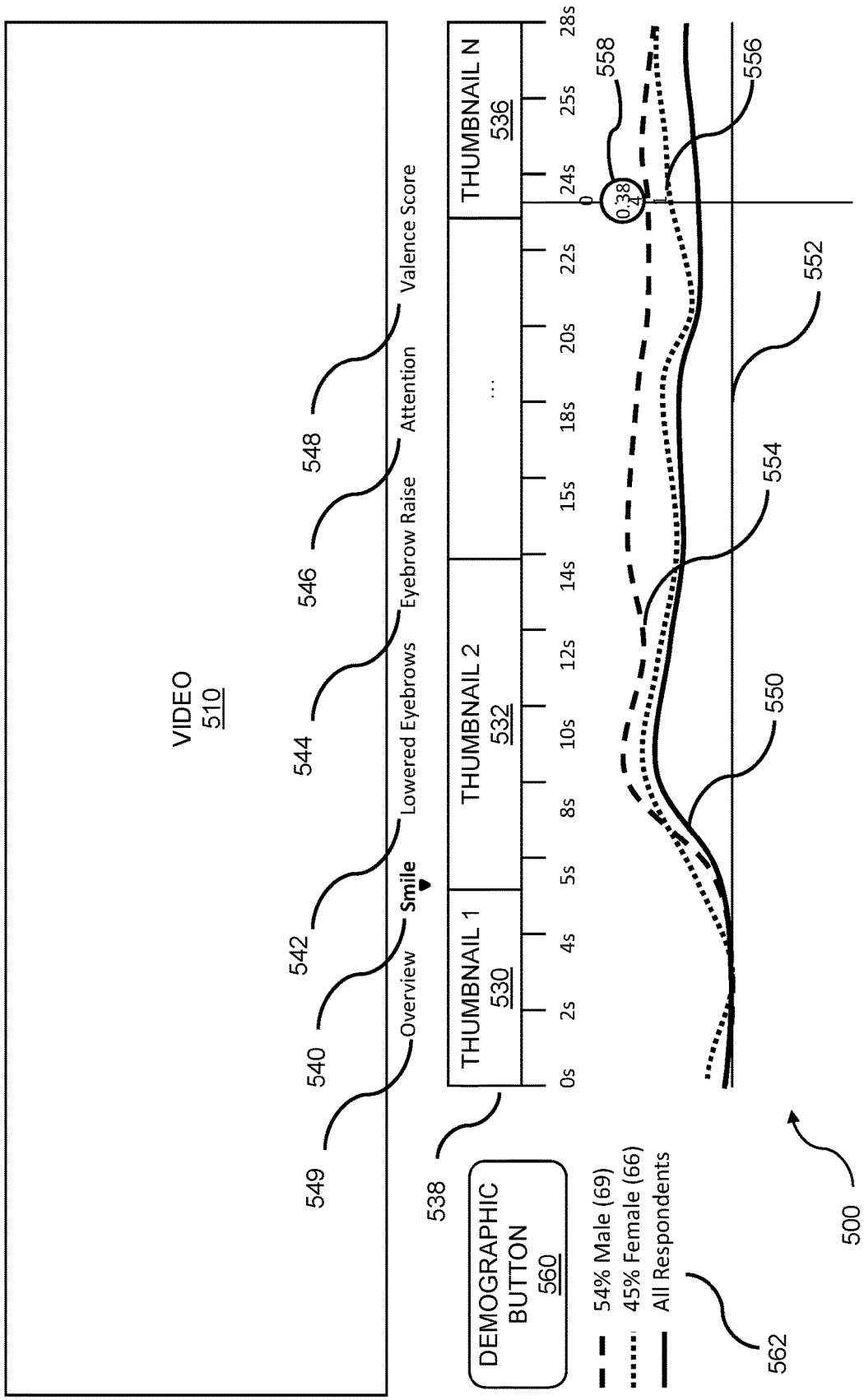
FIG. 5 is a graphical representation of displaying affect.

FIG. 5 is an example graphical representation of displaying affect. The display 500, or dashboard, is a graphical representation of cognitive state analysis that can be shown for a variety of analysis purposes including vehicle video recommendation via affect. The video viewer analysis can be presented on an electronic display. The display can be a television monitor, projector, computer monitor (including a laptop screen, a tablet screen, a netbook screen, and the like), a cell phone display, a mobile device, or another electronic display. In embodiments, the display is a webpage. An example display 500 is shown which includes a rendering of a video 510 along with associated cognitive state information. The visualization can further comprise the rendering related to the video 510. A user can select from among a plurality of video renderings using various buttons and/or tabs. The user interface allows a plurality of parameters to be displayed as a function of time, synchronized to the video rendering 510. Various embodiments have any number of selections available for the user, and some include other types of renderings instead of video. A set of thumbnail images for the selected renderings are shown in the example, including Thumbnail 1 530 and Thumbnail 2 532 through Thumbnail N 536 which can be displayed below the rendering along with a timeline 538. The thumbnails can show a graphic "storyboard" of the video rendering. This storyboard can assist a user in identifying a particular scene or location within the video rendering. Some embodiments do not include thumbnails or have a single thumbnail associated with the rendering, while various other embodiments have thumbnails of equal length and others have thumbnails of differing lengths. In some embodiments, the start and/or end of the thumbnails is determined based on changes in the captured viewer cognitive states associated with the rendering, or are based on particular points of interest in the video rendering. Thumbnails of one or more viewers can be shown along the timeline 538. The thumbnails of viewers can include peak expressions, expressions at key points in the video rendering 510, etc.

Some embodiments include the ability for a user to select a particular type of cognitive state information for display using various buttons or other selection methods. The cognitive state information can be based on one or more descriptors. The one or more descriptors can include, but are not limited to, one of action unit 4 (AU4), action unit 12 (AU12), and valence. By way of example, the smile cognitive state information is shown in the display 500 as the user might have previously selected the Smile button 540. Other types of cognitive state information that can be available for user selection in various embodiments include the Lowered the Eyebrows button 542, the Eyebrow Raise button 544, the Attention button 546, the Valence Score button 548, or other types of cognitive state information, depending on the embodiment. An Overview button 549 can be available which would allow a user to show graphs of the multiple types of cognitive state information simultaneously. The cognitive state information can include probability information for one or more descriptors, and the probabilities for the one of the one or more descriptors can vary for portions of the video rendering.

Because the Smile button 540 has been selected in the example shown, a smile graph 550 can be shown against a baseline 552, showing the aggregated smile cognitive state information of the plurality of individuals from whom cognitive state data was collected for the video. The male smile graph 554 and the female smile graph 556 can be shown so that the visual representation displays the aggregated cognitive state information. These graphs are provided by way of example only, as the cognitive state information can be gathered on a demographic basis as those viewers who comprise that demographic react to the video. The cognitive state data can be analyzed on a demographic basis. The various demographic-based graphs can be indicated using various line types as shown, or they can be indicated using color or another method of differentiation. A slider 558 can allow a user to select a particular time of the timeline and show the value of the chosen cognitive state for that particular time. The video 510 can be coordinated with the slider 558. The slider 558 is selected and moved with a mouse or another pointing device, in some embodiments. The video 510 can jump to the point in time to which the slider 558 has been moved. The cognitive states can be used to evaluate the value of the video.

In some embodiments, various types of demographic-based cognitive state information are selected using the demographic button 560. Such demographics can include gender, age, race, income level, education, or any other type of demographic, including dividing the respondents into those respondents that had higher reactions from those with lower reactions. A graph legend 562 indicating the various demographic groups, the line type or color for each group, the percentage of total respondents and/or the absolute number of respondents for each group, and/or other information about the demographic groups can be displayed. The cognitive state information can be aggregated according to the demographic type selected. Thus, aggregation of the cognitive state information is performed on a demographic basis so that cognitive state information is grouped based on the demographics, for some embodiments. The video thus can be evaluated for responses by various demographic groups.

Figure 6:
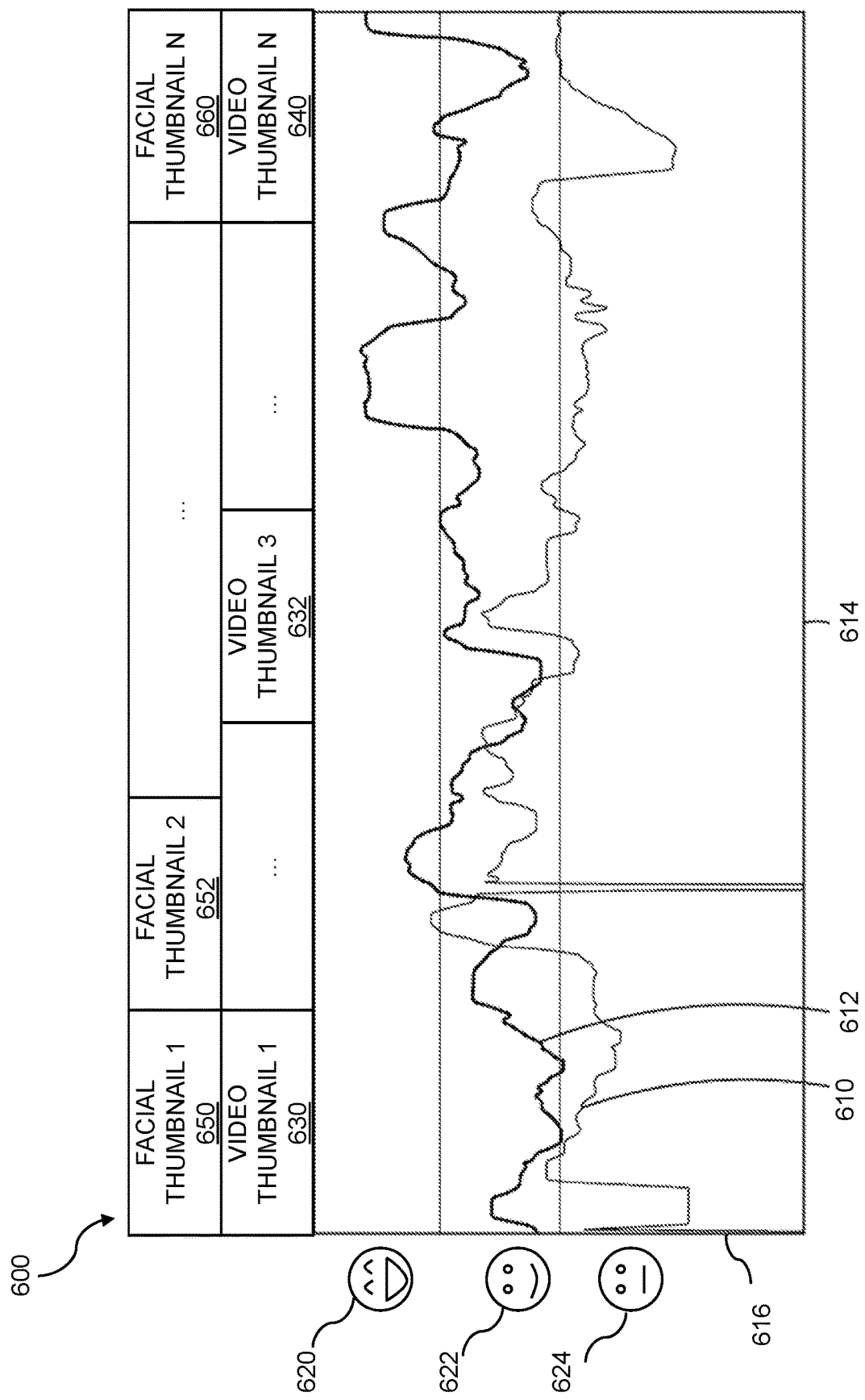
FIG. 6 is a graphical representation for displaying aggregated affect.

FIG. 6 is an example graphical representation for displaying affect based on cognitive state analysis. The graphical representation for displaying affect can support vehicle video recommendation via affect. The affect can be displayed along with an aggregated result from a group of people. The graphical representation 600 can be displayed on a web page, a web-enabled application, a dashboard, or another type of electronic display representation. A graph 610 for an individual on whom affect data is collected can be shown. Another graph 612 for affect collected on another individual or aggregated affect from multiple people can be shown. The cognitive state analysis can be based on facial image or physiological data collection. In some embodiments, the graph 610 indicates the amount or probability of a smile being observed for the individual. A higher value or point on the graph can indicate a stronger or larger smile. In certain spots, the graph can drop out or degrade when image collection was lost or was not able to identify the face of the person. The probability or intensity of an affect can be given along the y-axis 616, and a timeline can be given along the x-axis 614. The aggregated information can be based on taking the average, median, or another statistical or calculated value based on the information collected from a group of people. In some embodiments, the combination of the aggregated cognitive state information is accomplished using computational aggregation.

In some embodiments, graphical smiley face icons 620, 622, and 624 are shown, providing an indication of the amount of a smile or another facial expression. A first, very broad smiley face icon 620 can indicate a very large smile being observed, a second normal smiley face icon 622 can indicate a smile being observed, and a third face icon 624 can indicate no smile. The icons can correspond to a region on the y-axis 616 that indicates the probability or intensity of a smile.

A set of facial thumbnail images related to the selected graph or graphs, such as Facial Thumbnail 1 650 and Facial Thumbnail 2 652, through Facial Thumbnail N 660, can be shown above or below the graph and can be displayed with a timeline or another parameter along the x-axis 614. The thumbnails can show a graphic "storyboard" of the facial rendering. The storyboard can assist a user in identifying a particular scene or location within the facial rendering. Some embodiments do not include thumbnails or have a single thumbnail associated with the facial rendering, while various other embodiments have thumbnails of equal length and others have thumbnails of differing lengths. In some embodiments, the start and/or end of the thumbnails is determined based on changes in the captured viewer cognitive states associated with the rendering, or it is based on particular points of interest in the video rendering. Thumbnails of one or more viewers can be shown along a timeline 614 or another parameter. The thumbnails of viewers can include peak expressions, expressions at key points in the video rendering, key points in the graphs, etc.

A set of video thumbnail images comprising scenes from the video for the selected graph or graphs, such as Video Thumbnail 1 630 and Video Thumbnail 3 632, through Video Thumbnail N 640, can be shown above or below the graph and can be displayed with a timeline or another parameter along the x-axis 614. The thumbnails can show a graphic "storyboard" of the video rendering. This storyboard can assist a user in identifying a particular scene or location within the video rendering. Some embodiments do not include thumbnails or have a single thumbnail associated with the rendering, while various other embodiments have thumbnails of equal length, and others have thumbnails of differing lengths. In some embodiments, the start and/or end of the thumbnails is determined based on changes in the captured viewer cognitive states associated with the rendering, or it is based on particular points of interest in the video rendering.

Figure 7:
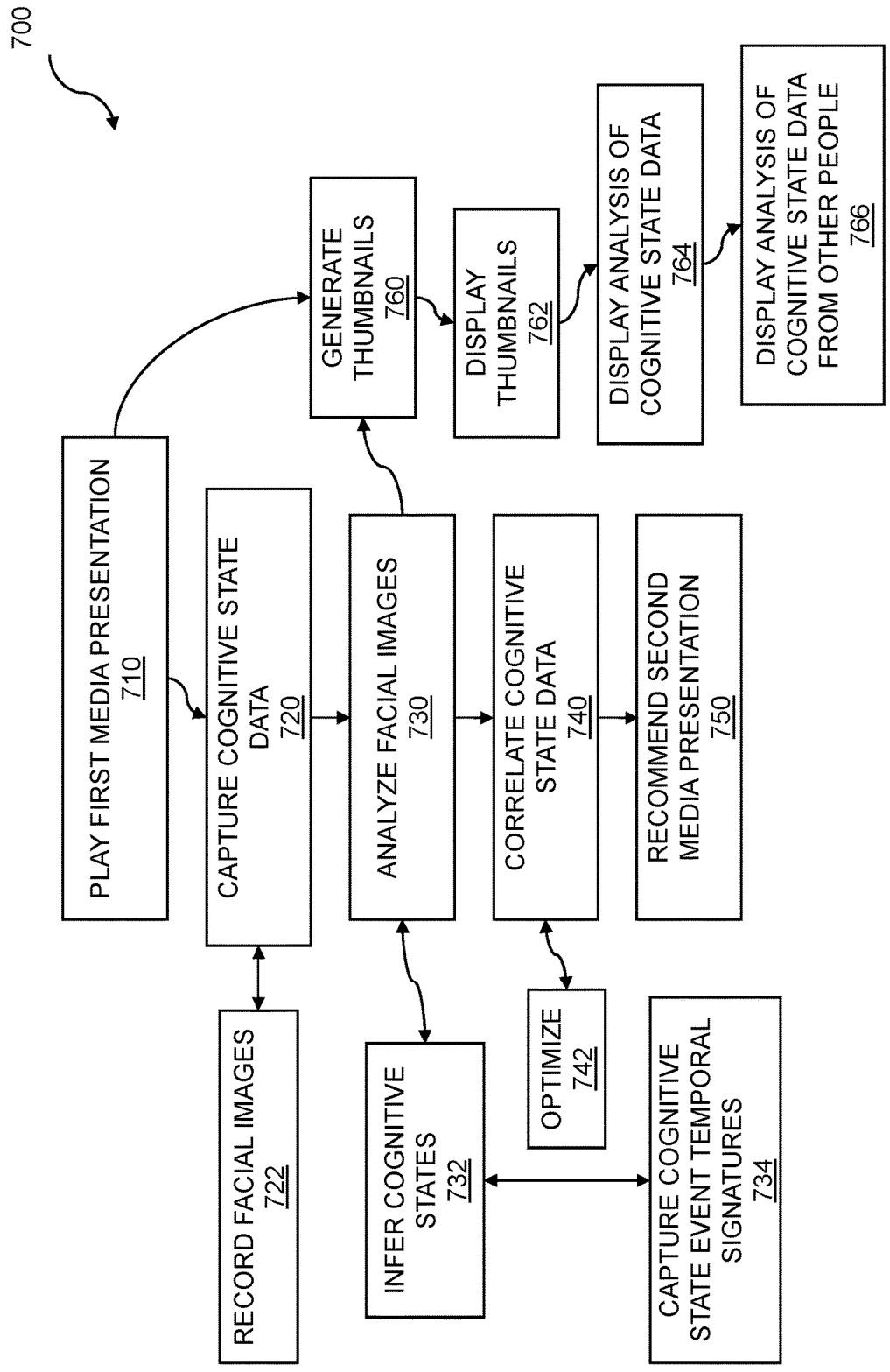
FIG. 7 is a flow diagram for affect-based recommendations.

FIG. 7 is a flow diagram for affect-based recommendations. Affect-based recommendations can enable vehicle video recommendation. A first media presentation is played on a video client to a vehicle occupant. Cognitive state data for the vehicle occupant is captured, where the cognitive state data includes video facial data from the vehicle occupant during the first media presentation playing. An analysis server ranks the first media presentation relative to another media presentation based on the cognitive state data which was captured for the vehicle occupant, wherein the ranking is for the vehicle occupant. The analysis server correlates the cognitive state data which was captured for the vehicle occupant to cognitive state data collected from other people who experienced the first media presentation. One or more further media presentation selections are recommended to the vehicle occupant, based on the ranking and the correlating.

The flow 700 begins with playing a first media presentation 710 to an individual. The first media presentation can be one of a group consisting of a movie, a television show, a web series, a webisode, a video, a video clip, an electronic game, an e-book, and an e-magazine, or another media object. The first media presentation can include a YouTube™ video, a Vimeo™ video, or a Netflix™ video. The first media presentation can be played on a web-enabled interface or another electronic display interface. The web-enabled interface can include a web page. The first media presentation can be played on a mobile device. The flow 700 continues with capturing cognitive state data 720 for the individual while the first media presentation is played. The cognitive state data collected can include physiological data, facial data, actigraphy data, and the like. The capturing of cognitive state data can further comprise recording facial images 722. Facial images can be captured by a webcam or another camera. The first media presentation can be played on a mobile device and the facial images can also be recorded with the mobile device. The recording of facial images 722 with the mobile device can be part of the capturing of cognitive state data 720. The flow 700 further comprises analyzing the facial images 730 for a facial expression. The facial expression can include a smile or a brow furrow. The analyzing facial images can further comprise using the facial images to infer cognitive states 732. The cognitive states can include frustration, confusion, disappointment, hesitation, cognitive overload, focusing, being engaged, attending, boredom, exploration, confidence, trust, delight, satisfaction, valence, skepticism, happiness, and the like. The inferring cognitive states 732 can include capturing a plurality of cognitive state event temporal signatures 734. The inferring of cognitive states can be based on both the cognitive state data which was collected and the analysis of the video facial data. In embodiments, this analysis of the video facial data is for at least brow furrows.

Clustering be used to include grouping of similar expressions, and the cognitive state event temporal signature can include a time duration and a peak intensity for expressions. In some embodiments, the cognitive state event temporal signature also includes a shape showing the transition of the intensity. Clustered expressions resulting from the analyzed data can include smiling, smirking, brow furrowing, and so on. The signature for the event can be based on various statistical, mathematical, or other measures. In particular, the event can be characterized by a change in facial expression over time. Of particular interest are rise and hold times, which pertain to how quickly the facial expression formed, and how long it remained. For example, if someone quickly smiles (e.g. within 500 milliseconds), the rise time can be considered short. Alternatively, if someone gradually smiles with increasing intensity over several seconds, the rise time is longer. Another measure is how long the person continued with the smile, or another expression of interest, based on the stimulus. The signature can include an emotion, in that the identified signature can show collective or individual emotional response to external stimuli. Any emotion can be included in the signature for the event, including one or more of humor, sadness, poignancy, and mirth. Other emotions such as affection, confidence, depression, euphoria, distrust, hope, hysteria, passion, regret, surprise, and zest can also be included. As previously noted, the signature can include time duration information on facial expressions such as a rise time, a fall time, a peak time, and so on, for various expressions. The signature can also include a peak intensity for expressions. The peak intensity can range from a weakest trace to a maximum intensity as defined by a predetermined scale, such as the AU intensity scale. The rating of the intensity can be based on an individual person, on a group of people, and so on. The signature can include a shape for an intensity transition from low intensity to a peak intensity, thus quantifying facial expression transitions as part of the signature. For example, the shape for a low-to-peak intensity transition can indicate a rate at which the transition occurred, whether the peak intensity was sharp or diffuse, and so on.

Conversely, the signature can include a shape for an intensity transition from a peak intensity to low intensity as another valuable quantifier of facial expressions. As above, the shape of the peak-to-low intensity transition can indicate a rate at which the transition occurred along with various other useful characteristics relating to the transition. The determining can also include generating other signatures for other events based on the analyzing, or as a result of the analyzing. The other signatures can relate to secondary expressions and can be generated to clarify nuances in a given signature. Returning to the previously mentioned example of a comedic performance, a signature for a certain type of comedic performance can be determined, but in some situations, it might prove helpful to generate further signatures for certain audiences watching a certain instance of the comedic performance. That is, while a plurality of people is watching a comedic performance with a previously defined signature, a second signature can be generated on the group to define a new subgenre of comedic performance, for example.

The cognitive state event temporal signatures can indicate a collective cognitive state of a group of people over a period of time as the group experiences an event. For example, the group of people might be asked to view a video. During the course of the video, the cognitive state of the group of people can be assessed, and a signature can be obtained. For example, the signature can indicate a smile intensity that can correlate to a particular point in the video that the subjects are viewing. In this way, an event can be abstracted to one or more signatures comprising cognitive states which occur over time. The cognitive state event temporal signature(s) can be used for analysis. The cognitive state event temporal signature(s) can be used for correlating cognitive state data. The flow 700 can include matching a first event signature against the captured cognitive state data 720. Thus, embodiments include matching a first event signature, from the plurality of cognitive state event signatures, against the cognitive state data that was captured. Components of cognitive state event temporal signatures can include a peak intensity value, a difference between a trough and a peak value, a rate of expression change rising towards the peak or descending from the peak, a duration of intensity, and so on. In embodiments, the following signature attributes are tracked: Event Height (maximum value), Event Length (duration between onset and offset), Event Rise (increase from onset to peak), Event Decay (decrease from peak to next offset), Rise Speed (gradient of event rise), and Decay Speed (gradient of event decay). Signature attributes can be used to determine if a significant event occurred and to help determine the intensity and duration of the event. In embodiments, cognitive state event temporal signatures are identified by determining the length of time between adjacent local minima of a facial expression probability curve.

The flow 700 continues with correlating the cognitive state data 740 which was captured for the individual to cognitive state data collected from other people who experienced the first media presentation. The correlating can include identifying similar likes and dislikes as well as various other similar cognitive states. In some embodiments, distributions of responses to various videos are correlated, while in other embodiments, differences are correlated, such as, for example, identifying maximally dissimilar responses. Maximally dissimilar can refer to complete opposites, such as a smile vs. a frown or happiness vs. sadness. Maximally dissimilar responses can also refer to observing differing affect that is unexpected, while not necessarily opposite. For example, a sad video scene could, as expected, elicit a response of sadness. It could also elicit a response of nervous laughing by someone who is unable to cope with the depth of emotion being displayed. However, it could also elicit a non-response, as in the case of a person who tends to be stoic and unexpressive. In this case, the expected response of sadness can be considered maximally dissimilar to a non-response. Furthermore, the unexpected non-response can be considered maximally dissimilar to a nervous laugh response. Many other such examples of non-intuitive maximally dissimilar responses exist. In some embodiments, certain cognitive states are identified as being similar, while others are identified as being dissimilar during part of the correlation. The flow 700 can include optimizing 742 the media presentation based on the cognitive state data. The optimizing 742 can include modifying content or recommending changes in content, such as eliminating scenes, reducing certain material, or emphasizing certain actors. In embodiments, the media presentation includes a mixture of advertising and content. The optimizing 742 can select one or more advertisements to be interspersed with the content and can also include ordering one or more advertisements to be interspersed with the content. Additionally, the optimizing 742 can include selecting times within the content for playing the one or more advertisements. The optimizing 742 can include identifying portions of an advertisement that are removed to form a shortened advertisement.

The flow 700 includes recommending a second media presentation 750 to the individual based on the cognitive state data which was captured for the individual. The recommending the second media presentation to the individual can be based on the correlating between the individual and the other people. The second media presentation can be one of a group consisting of a movie, a television show, a web series, a webisode, a video, a video clip, an electronic game, an e-book, an e-magazine, and the like. The second media presentation can include a YouTube™ video, a Vimeo™ video, or a Netflix™ video.

The flow 700 can further comprise generating a set of thumbnails 760 for the first media presentation which was played and displaying the set of thumbnails 762 on a second web-enabled interface or digital display along with an analysis of the cognitive state data from the individual 764. The set of thumbnails can comprise scenes from the first media presentation. The selection of the thumbnail from the set of thumbnails can be based on facial expressions. The set of thumbnails can be generated automatically and can include removing a frame from the set of thumbnails based on a darkness threshold. Another frame can be used in place of the frame that was removed. The flow 700 can further comprise displaying an analysis of the cognitive state data from the other people 766. Various steps in the flow 700 may be changed in order, repeated, omitted, or the like without departing from the disclosed inventive concepts. Various embodiments of the flow 700 may be included in a computer program product embodied in a non-transitory computer readable medium that includes code executable by one or more processors.

Figure 8:
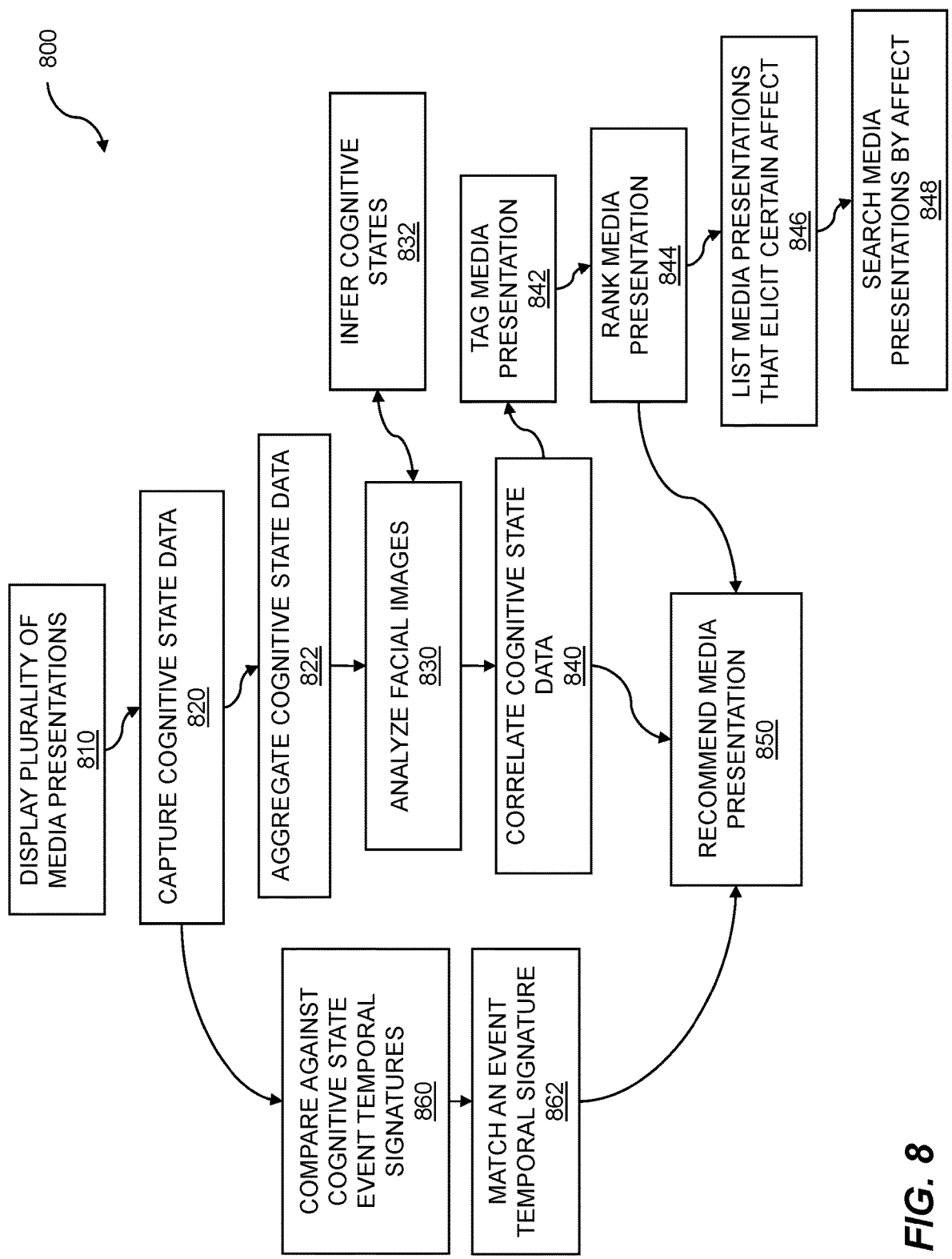
FIG. 8 is a flow diagram for affect-based video ranking.

FIG. 8 is a flow diagram for affect-based video ranking 800. Affect-based video ranking can enable vehicle video recommendation via affect. A first media presentation is played on a video client to a vehicle occupant. Cognitive state data for the vehicle occupant is captured, where the cognitive state data includes video facial data from the vehicle occupant during the first media presentation playing. An analysis server ranks the first media presentation relative to another media presentation based on the cognitive state data which was captured for the vehicle occupant, wherein the ranking is for the vehicle occupant. The analysis server correlates the cognitive state data which was captured for the vehicle occupant to cognitive state data collected from other people who experienced the first media presentation. One or more further media presentation selections are recommended to the vehicle occupant, based on the ranking and the correlating.

The flow 800 begins with displaying a plurality of media presentations 810 to a group of people. The plurality of media presentations can include videos. The plurality of videos can include YouTube™ videos, Vimeo™ videos, or Netflix™ videos. Further, the plurality of media presentations can include one of a group consisting of a movie, a movie trailer, a television show, a web series, a webisode, a video, a video clip, an advertisement, a music video, an electronic game, an e-book, and an e-magazine. The flow 800 continues with capturing cognitive state data 820 from the group of people while the plurality of media presentations is displayed. Thus, cognitive state data can be captured from multiple people. The affect data can include facial images. In some embodiments, the playing of the media presentations is done on a mobile device and the recording of the facial images is done with the mobile device. The flow 800 includes aggregating the cognitive state data 822 from the multiple people. The flow 800 further comprises analyzing the facial images 830 for a facial expression. The facial expression can include a smile or a brow furrow. The flow 800 can further comprise using the facial images to infer cognitive states 832. The cognitive states can include one of a group consisting of frustration, confusion, disappointment, hesitation, cognitive overload, focusing, being engaged, attending, boredom, exploration, confidence, trust, delight, valence, skepticism, satisfaction, and the like.

The flow 800 includes correlating the cognitive state data 840 captured from the group of people who have viewed the plurality of media presentations and had their cognitive state data captured. The plurality of videos viewed by the group of people can have some common videos seen by each of the people in the group of people. In some embodiments, the plurality of videos does not include an identical set of videos. The flow 800 can continue with tagging the plurality of media presentations 842 with cognitive state information based on the cognitive state data which was captured. In some embodiments, the affect information is simply the affect data, while in other embodiments, the affect information is determined from the inferred cognitive states. In still other embodiments, the affect information is derived from the results of the correlation. The flow 800 can continue with ranking the media presentations 844 relative to another media presentation based on the cognitive state data which was collected. The ranking can be for an individual based on the cognitive state data captured from the individual. The ranking can be based on anticipated preferences for the individual. In some embodiments, the ranking of a first media presentation relative to another media presentation is based on the cognitive state data which was aggregated from multiple people. The ranking can also be relative to media presentations previously stored with affect information. The ranking can include ranking a video relative to another video based on the cognitive state data which was captured. The flow 800 can further comprise displaying the videos which elicit a certain affect 846. The certain affect can include one of a group consisting of smiles, engagement, attention, interest, sadness, liking, disliking, and so on. The ranking can further comprise displaying the videos which elicited a larger number of smiles. As a result of the ranking, the media presentations can be sorted based on which videos are the funniest, which are the saddest, which generate the most tears, or which engender some other response. The flow 800 can further comprise searching through the videos based on certain affect data 848. A search can identify videos which are very engaging, funny, sad, poignant, or the like.

The flow 800 includes comparing the cognitive state data that was captured for the individual against a plurality of cognitive state event temporal signatures 860. In embodiments, multiple cognitive state event temporal signatures have been obtained from previous analysis of numerous people. The cognitive state event temporal signatures can include information on rise time to facial expression intensity, fall time from facial expression intensity, duration of a facial expression, and so on. In some embodiments, the cognitive state event temporal signatures are associated with certain demographics, ethnicities, cultures, etc. The cognitive state event temporal signatures can be used to identify one or more of sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. The cognitive state event temporal signatures can be used to identify liking or satisfaction with a media presentation. The cognitive state event temporal signatures can be used to correlate with appreciating a second media presentation. The flow 800 can include matching a first event signature 862, from the plurality of cognitive state event temporal signatures, against the cognitive state data that was captured. The matching can include identifying similar aspects of the cognitive state event temporal signature such as rise time, fall time, duration, and so on. The matching can include matching a series of facial expressions described in cognitive state event temporal signatures. In some embodiments, a second cognitive state event temporal signature is used to identify a sequence of cognitive state data being expressed by an individual.

The flow 800 includes recommending a second media presentation 850 to an individual based on the affect data that was captured and based on the ranking. The recommending the second media presentation to the individual is further based on the comparing of the cognitive state data to the plurality of cognitive state event temporal signatures. The second media presentation can be one of a group consisting of a movie, a movie trailer, a television show, a web series, a webisode, a video, a video clip, an advertisement, a music video, an electronic game, an e-book, and an e-magazine. The recommending the second media presentation can be further based on the matching of the first event signature. The recommending can be based on the similarity of cognitive states that were expressed. The recommending can be based on a numerically quantifiable determination of satisfaction or appreciation of the first media presentation and an anticipated numerically quantifiable satisfaction or appreciation of second first media presentation.

Based on the cognitive states, recommendations to or from an individual can be provided. One or more recommendations can be made to the individual based on cognitive states, affect, or facial expressions. A correlation between one individual and others with similar affect exhibited during multiple videos can be made. The correlation can include a record of other videos, games, or other experiences, along with their affect. Likewise, a recommendation for a movie, video, video clip, webisode or another activity can be made to an individual based on his or her affect. Various steps in the flow 800 may be changed in order, repeated, omitted, or the like without departing from the disclosed inventive concepts. Various embodiments of the flow 800 may be included in a computer program product embodied in a non-transitory computer readable medium that includes code executable by one or more processors.

The human face provides a powerful communications medium through its ability to exhibit a myriad of expressions that can be captured and analyzed for a variety of purposes. In some cases, media producers are acutely interested in evaluating the effectiveness of message delivery by video media. Such video media includes advertisements, political messages, educational materials, television programs, movies, government service announcements, etc. Automated facial analysis can be performed on one or more video frames containing a face in order to detect facial action. Based on the facial action detected, a variety of parameters can be determined including affect valence, spontaneous reactions, facial action units, and so on. The parameters that are determined can be used to infer or predict emotional and cognitive states. For example, determined valence can be used to describe the emotional reaction of a viewer to a video media presentation or another type of presentation. Positive valence provides evidence that a viewer is experiencing a favorable emotional response to the video media presentation, while negative valence provides evidence that a viewer is experiencing an unfavorable emotional response to the video media presentation. Other facial data analysis can include the determination of discrete emotional states of the viewer or viewers.

Facial data can be collected from a plurality of people using any of a variety of cameras. A camera can include a webcam, a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. In some embodiments, the person is permitted to "opt-in" to the facial data collection. For example, the person can agree to the capture of facial data using a personal device such as a mobile device or another electronic device by selecting an opt-in choice. Opting-in can then turn on the person's webcam-enabled device and can begin the capture of the person's facial data via a video feed from the webcam or another camera. The video data that is collected can include one or more persons experiencing an event. The one or more persons can be sharing a personal electronic device, or can each be using one or more devices for video capture. The videos that are collected can be collected using a web-based framework. The web-based framework can be used to display the video media presentation or event as well as to collect videos from any number of viewers who are online. That is, the collection of videos can be crowdsourced from those viewers who elected to opt-in to the video data collection.

In some embodiments, a high frame rate camera is used. A high frame rate camera has a frame rate of 60 frames per second or higher. With such a frame rate, micro expressions can also be captured. Micro expressions are very brief facial expressions, lasting only a fraction of a second. They occur when a person either deliberately or unconsciously conceals a feeling.

In some cases, micro expressions happen when people have hidden their feelings from themselves (repression) or when they deliberately try to conceal their feelings from others. Sometimes the micro expressions might only last about 50 milliseconds. Hence, these expressions can go unnoticed by a human observer. However, a high frame rate camera can be used to capture footage at a sufficient frame rate such that the footage can be analyzed for the presence of micro expressions. Micro expressions can be analyzed via action units, as previously described, with various attributes such as brow raising, brow furls, eyelid raising, and the like. Thus, embodiments analyze micro expressions that are easily missed by human observers due to their transient nature.

The videos captured from the various viewers who chose to opt-in can be substantially different in terms of video quality, frame rate, etc. As a result, the facial video data can be scaled, rotated, and otherwise adjusted to improve consistency. Human factors further play into the capture of the facial video data. The facial data that is captured might or might not be relevant to the video media presentation being displayed. For example, the viewer might not be paying attention, might be fidgeting, might be distracted by an object or event near the viewer, or might be otherwise inattentive to the video media presentation. The behavior exhibited by the viewer can prove challenging to analyze due to viewer actions including eating, speaking to another person or persons, speaking on the phone, etc. The videos collected from the viewers might also include other artifacts that pose challenges during the analysis of the video data. The artifacts can include such items as eyeglasses (because of reflections), eye patches, jewelry, and clothing that occludes or obscures the viewer's face. Similarly, a viewer's hair or hair covering can present artifacts by obscuring the viewer's eyes and/or face.

The captured facial data can be analyzed using the facial action coding system (FACS). The FACS seeks to define groups or taxonomies of facial movements of the human face. The FACS encodes movements of individual muscles of the face, where the muscle movements often include slight, instantaneous changes in facial appearance. The FACS encoding is commonly performed by trained observers, but can also be performed on automated, computer-based systems. Analysis of the FACS encoding can be used to determine emotions of the persons whose facial data is captured in the videos. The FACS is used to encode a wide range of facial expressions that are anatomically possible for the human face. The FACS encodings include action units (AUs) and related temporal segments that are based on the captured facial expression. The AUs are open to higher order interpretation and decision-making. For example, the AUs can be used to recognize emotions experienced by the observed person. Emotion-related facial actions can be identified using the emotional facial action coding system (EM-FACS) and the facial action coding system affect interpretation dictionary (FACSAID), for example. For a given emotion, specific action units can be related to the emotion. For example, the emotion of anger can be related to AUs 4, 5, 7, and 23, while happiness can be related to AUs 6 and 12. Other mappings of emotions to AUs have also been previously associated. The coding of the AUs can include an intensity scoring that ranges from A (trace) to E (maximum). The AUs can be used for analyzing images to identify patterns indicative of a particular mental and/or emotional state. The AUs range in number from 0 (neutral face) to 98 (fast up-down look). The AUs include so-called main codes (inner brow raiser, lid tightener, etc.), head movement codes (head turned left, head up, etc.), eye movement codes (eyes turned left, eyes up, etc.), visibility codes (eyes not visible, entire face not visible, etc.), and gross behavior codes (sniff, swallow, etc.). Emotion scoring can be included where intensity, as well as specific emotions, moods, or cognitive states, are evaluated.

The coding of faces identified in videos captured of people observing an event can be automated. The automated systems can detect facial AUs or discrete emotional states. The emotional states can include amusement, fear, anger, disgust, surprise, and sadness, for example. The automated systems can be based on a probability estimate from one or more classifiers, where the probabilities can correlate with an intensity of an AU or an expression. The classifiers can be used to identify into which of a set of categories a given observation can be placed. For example, the classifiers can be used to determine a probability that a given AU or expression is present in a given frame of a video. The classifiers can be used as part of a supervised machine learning technique where the machine learning technique can be trained using "known good" data. Once trained, the machine learning technique can proceed to classify new data that is captured.

The supervised machine learning models can be based on support vector machines (SVMs). An SVM can have an associated learning model that is used for data analysis and pattern analysis. For example, an SVM can be used to classify data that can be obtained from collected videos of people experiencing a media presentation. An SVM can be trained using "known good" data that is labeled as belonging to one of two categories (e.g. smile and no-smile). The SVM can build a model that assigns new data into one of the two categories. The SVM can construct one or more hyperplanes that can be used for classification. The hyperplane that has the largest distance from the nearest training point can be determined to have the best separation. The largest separation can improve the classification technique by increasing the probability that a given data point can be properly classified.

In another example, a histogram of oriented gradients (HoG) can be computed. The HoG can include feature descriptors and can be computed for one or more facial regions of interest. The regions of interest of the face can be located using facial landmark points, where the facial landmark points can include outer edges of nostrils, outer edges of the mouth, outer edges of eyes, etc. A HoG for a given region of interest can count occurrences of gradient orientation within a given section of a frame from a video, for example. The gradients can be intensity gradients and can be used to describe an appearance and a shape of a local object. The HoG descriptors can be determined by dividing an image into small, connected regions, also called cells. A histogram of gradient directions or edge orientations can be computed for pixels in the cell. Histograms can be contrast-normalized based on intensity across a portion of the image or the entire image, thus reducing any influence from illumination or shadowing changes between and among video frames. The HoG can be computed on the image or on an adjusted version of the image, where the adjustment of the image can include scaling, rotation, etc. For example, the image can be adjusted by flipping the image around a vertical line through the middle of a face in the image. The symmetry plane of the image can be determined from the tracker points and landmarks of the image.

In an embodiment, an automated facial analysis system identifies five facial actions or action combinations in order to detect spontaneous facial expressions for media research purposes. Based on the facial expressions that are detected, a determination can be made with regard to the effectiveness of a given video media presentation, for example. The system can detect the presence of the AUs or the combination of AUs in videos collected from a plurality of people. The facial analysis technique can be trained using a web-based framework to crowdsource videos of people as they watch online video content. The video can be streamed at a fixed frame rate to a server. Human labelers can code for the presence or absence of facial actions including a symmetric smile, a unilateral smile, an asymmetric smile, and so on. The trained system can then be used to automatically code the facial data collected from a plurality of viewers experiencing video presentations (e.g. television programs).

Spontaneous asymmetric smiles can be detected in order to understand viewer experiences. Related literature indicates that as many asymmetric smiles occur on the right hemi face as do on the left hemi face, for spontaneous expressions. Detection can be treated as a binary classification problem, where images that contain a right asymmetric expression are used as positive (target class) samples and all other images as negative (non-target class) samples. Classifiers perform the classification, including classifiers such as support vector machines (SVMs) and random forests. Random forests can include ensemble-learning methods that use multiple learning algorithms to obtain better predictive performance. Frame-by-frame detection can be performed to recognize the presence of an asymmetric expression in each frame of a video. Facial points can be detected, including the top of the mouth and the two outer eye corners. The face can be extracted, cropped, and warped into a pixel image of a specific dimension (e.g. 96×96 pixels). In embodiments, the inter-ocular distance and vertical scale in the pixel image are fixed. Feature extraction can be performed using computer vision software such as OpenCV™. Feature extraction can be based on the use of HoGs. HoGs can include feature descriptors and can be used to count occurrences of gradient orientation in localized portions or regions of the image. Other techniques can be used for counting occurrences of gradient orientation, including edge orientation histograms, scale-invariant feature transformation descriptors, etc. The AU recognition tasks can also be performed using Local Binary Patterns (LBPs) and Local Gabor Binary Patterns (LGBPs). The HoG descriptor represents the face as a distribution of intensity gradients and edge directions, and is robust in its ability to translate and scale. Differing patterns, including groupings of cells of various sizes and arranged in variously sized cell blocks, can be used. For example, 4×4 cell blocks of 8×8 pixel cells with an overlap of half of the block can be used. Histograms of channels can be used, including nine channels or bins evenly spread over 0-180 degrees. In this example, the HoG descriptor on a 96×96 image is 25 blocks×16 cells×9 bins=3600, the latter quantity representing the dimension. AU occurrences can be rendered. The videos can be grouped into demographic datasets based on nationality and/or other demographic parameters for further detailed analysis.

Figure 9:
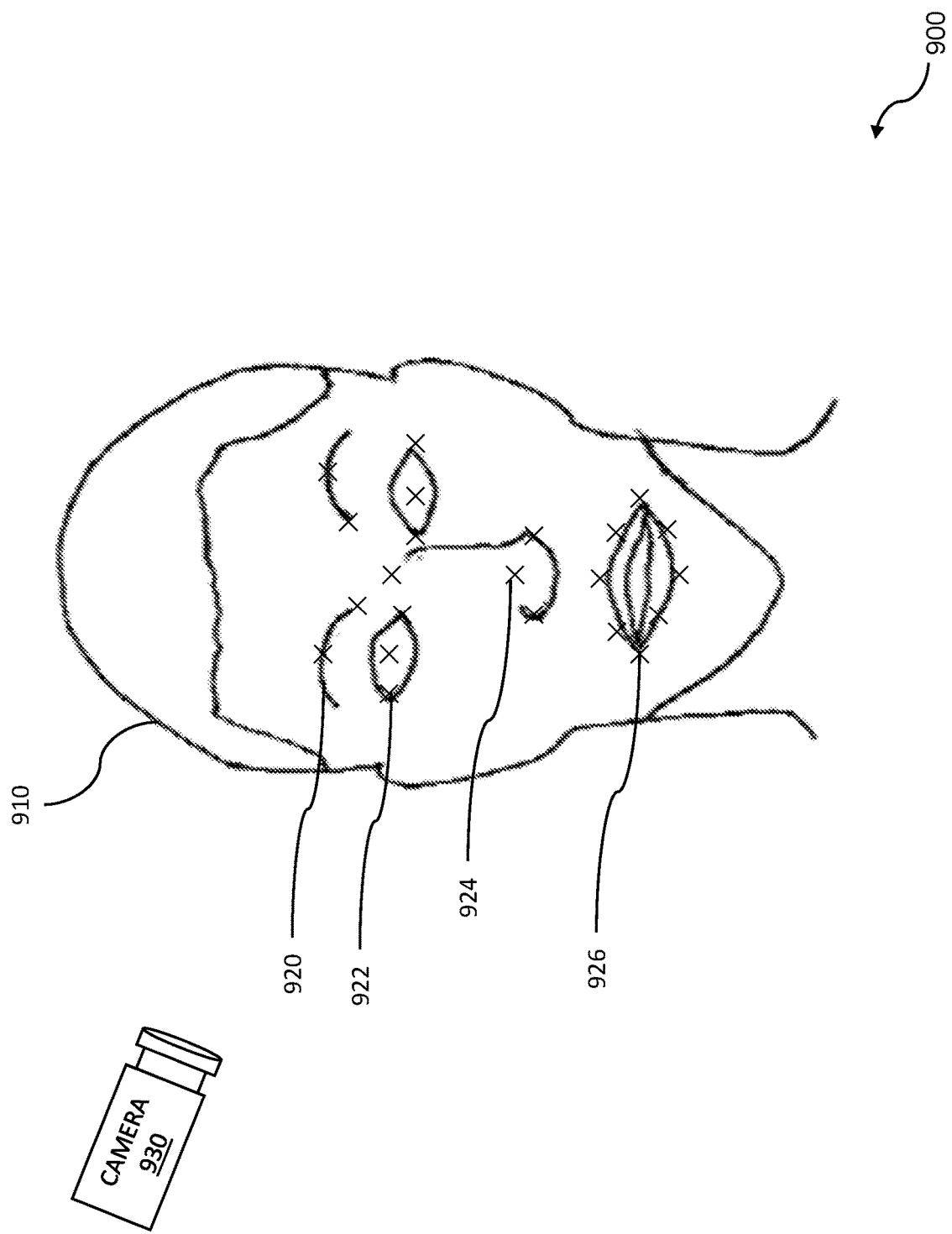
FIG. 9 shows example facial data collection including landmarks.

FIG. 9 shows a diagram 900 illustrating example facial data collection including landmarks. The facial data, video facial data, and other data can be included in the collection of cognitive state data for a person such as a vehicle occupant. The cognitive state data, including the video facial data, can be collected as a vehicle occupant views a media presentation. The media presentation can be ranked relative to other media presentations, and the cognitive state data for the individual can be correlated to cognitive state data collected from other individuals. The ranking and the correlating can be used for recommending further media presentation selections to an individual such as the vehicle occupant.

A face 910 can be observed using a camera 930 in order to collect facial data that includes facial landmarks. The facial data can be collected from a plurality of people using one or more of a variety of cameras. As discussed above, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The quality and usefulness of the facial data that is captured can depend, for example, on the position of the camera 930 relative to the face 910, the number of cameras used, the illumination of the face, etc. For example, if the face 910 is poorly lit or over-exposed (e.g. in an area of bright light), the processing of the facial data to identify facial landmarks might be rendered more difficult. In another example, the camera 930 being positioned to the side of the person might prevent capture of the full face. Other artifacts can degrade the capture of facial data. For example, the person's hair, prosthetic devices (e.g. glasses, an eye patch, and eye coverings), jewelry, and clothing can partially or completely occlude or obscure the person's face. Data relating to various facial landmarks can include a variety of facial features. The facial features can comprise an eyebrow 920, an outer eye edge 922, a nose 924, a corner of a mouth 926, and so on. Any number of facial landmarks from the captured facial data can be identified. The facial landmarks that are identified can be analyzed to identify facial action units. For example, the action units that can be identified include AU02 outer brow raiser, AU14 dimpler, AU17 chin raiser, and so on. Any number of action units can be identified. The action units can be used alone and/or in combination to infer one or more cognitive states and emotions. A similar process can be applied to gesture analysis (e.g. hand gestures).

Figure 10:
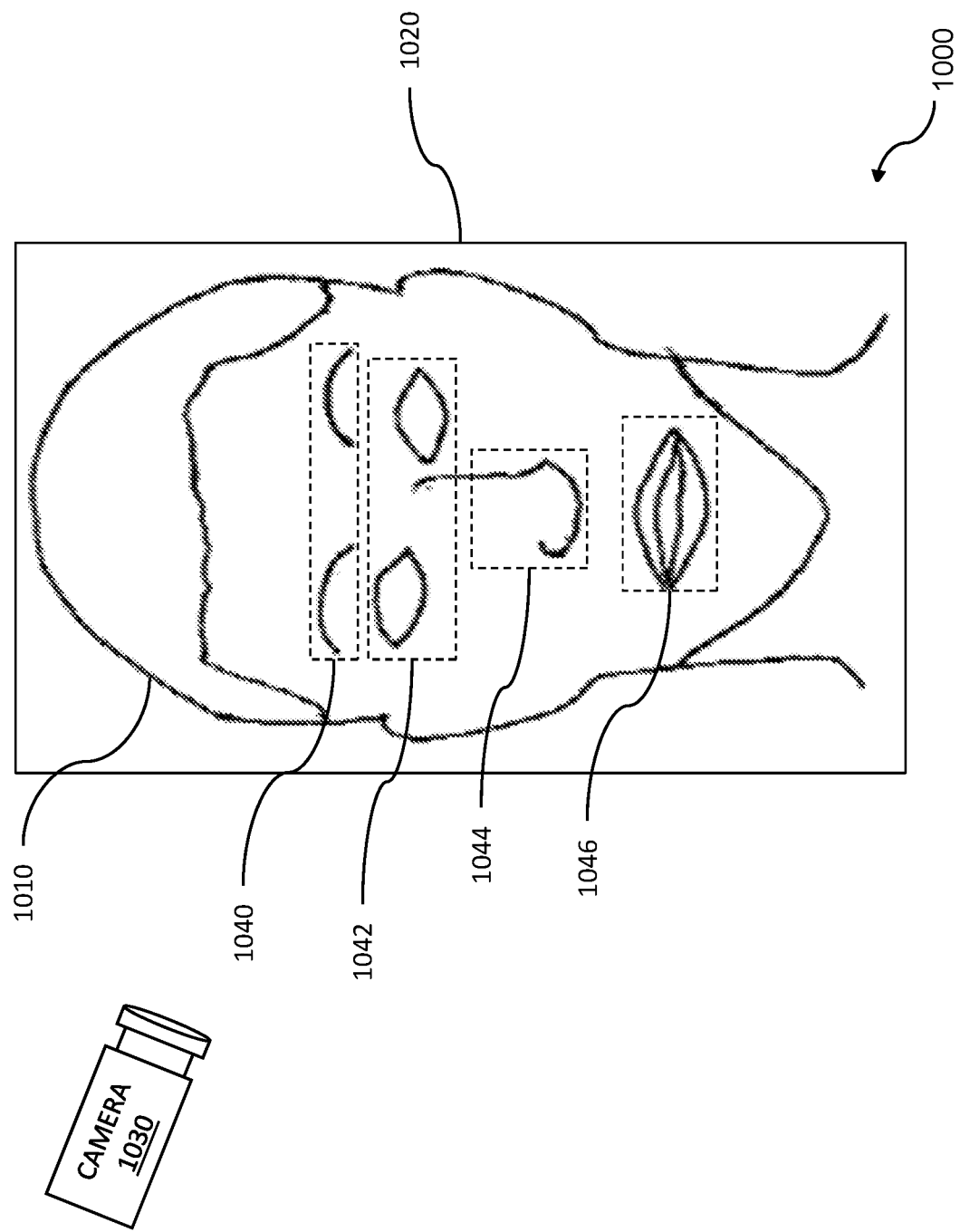
FIG. 10 shows example facial data collection including regions.

FIG. 10 shows example facial data collection including regions. The facial data can include video facial data. The video facial data can be included in the collection of cognitive state data for a vehicle occupant. The cognitive state data, including the video facial data, can be ranked and correlated for recommending further media presentation selections to an individual such as the vehicle occupant. The collecting of facial data including regions can be performed for data collected from a remote computing device. The facial data including regions can be collected from people as they interact with the Internet. Various regions of a face can be identified and used for a variety of purposes including facial recognition, facial analysis, and so on. The collecting of facial data including regions can be based on sub-sectional components of a population. The sub-sectional components can be used with performing the evaluation of content of the face, identifying facial regions, etc. The sub-sectional components can be used to provide a context. Facial analysis can be used to determine, predict, estimate, etc. cognitive states, emotions, and so on of a person from whom facial data can be collected. The one or more emotions that can be determined by the analysis can be represented by an image, a figure, an icon, etc. The representative icon can include an emoji. One or more emoji can be used to represent a cognitive state, a mood, etc. of an individual; to represent food, a geographic location, weather; and so on. The emoji can include a static image. The static image can be a predefined size such as a certain number of pixels. The emoji can include an animated image. The emoji can be based on a GIF or another animation standard. The emoji can include a cartoon representation. The cartoon representation can be any cartoon type, format, etc. that can be appropriate to representing an emoji. In the example 1000, facial data can be collected, where the facial data can include regions of a face. The facial data that is collected can be based on sub-sectional components of a population. When more than one face can be detected in an image, facial data can be collected for one face, some faces, all faces, and so on. The facial data, which can include facial regions, can be collected using any of a variety of electronic hardware and software techniques. The facial data can be collected using sensors including motion sensors, infrared sensors, physiological sensors, imaging sensors, and so on. A face 1010 can be observed using a camera 1030, a sensor, a combination of cameras and/or sensors, and so on. The camera 1030 can be used to collect facial data that can be used to determine that a face is present in an image. When a face is present in an image, a bounding box 1020 can be placed around the face. Placement of the bounding box around the face can be based on detection of facial landmarks. The camera 1030 can be used to collect facial data 1020 from the bounding box, where the facial data can include facial regions. The facial data can be collected from a plurality of people using any of a variety of cameras. As discussed previously, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. As discussed previously, the quality and usefulness of the facial data that is captured can depend on the position of the camera 1030 relative to the face 1010, the number of cameras and/or sensors used, the illumination of the face, any obstructions to viewing the face, and so on.

The facial regions that can be collected by the camera 1030, sensor, or combination of cameras and/or sensors can include any of a variety of facial features. The facial features that can be included in the facial regions that are collected can include eyebrows 1040, eyes 1042, a nose 1044, a mouth 1046, ears, hair, texture, tone, and so on. Multiple facial features can be included in one or more facial regions. The number of facial features that can be included in the facial regions can depend on the desired amount of data to be captured, whether a face is in profile, whether the face is partially occluded or obstructed, etc. The facial regions that can include one or more facial features can be analyzed to determine facial expressions. The analysis of the facial regions can also include determining probabilities of occurrence of one or more facial expressions. The facial features that can be analyzed can also include textures, gradients, colors, shapes, etc. The facial features can be used to determine demographic data, where the demographic data can include age, ethnicity, culture, gender, etc. Multiple textures, gradients, colors, shapes, and so on, can be detected by the camera 1030, a sensor, or a combination of cameras and sensors. Texture, brightness, and color, for example, can be used to detect boundaries in an image for detection of a face, facial features, facial landmarks, and so on.

A texture in a facial region can include facial characteristics, skin types, and so on. In some instances, a texture in a facial region can include smile lines, crow's feet, wrinkles, and so on. Another texture that can be used to evaluate a facial region can include a smooth potion of skin such as a smooth portion of a check. A gradient in a facial region can include values assigned to local skin texture, shading, etc. A gradient can be used to encode, for instance, a texture, by computing magnitudes in a local neighborhood or portion of an image. The computed values can be compared to discrimination levels, threshold values, and so on. The gradient can be used to determine gender, facial expression, etc. A color in a facial region can include eye color, skin color, hair color, and so on. A color can be used to determine demographic data, where the demographic data can include ethnicity, culture, age, gender, etc. A shape in a facial region can include shape of a face, eyes, nose, mouth, ears, and so on. As with color in a facial region, shape in a facial region can be used to determine demographic data including ethnicity, culture, age, gender, and so on.

The facial regions can be detected based on detection of edges, boundaries, and so on, of features that can be included in an image. The detection can be based on various types of analysis of the image. The features that can be included in the image can include one or more faces. A boundary can refer to a contour in an image plane where the contour can represent ownership of a particular picture element (pixel) from one object, feature, etc. in the image, to another object, feature, and so on, in the image. An edge can be a distinct, low-level change of one or more features in an image. That is, an edge can be detected based on a change, including an abrupt change, in color, brightness, etc. within an image. In embodiments, image classifiers are used for the analysis. The image classifiers can include algorithms, heuristics, and so on, and can be implemented using functions, classes, subroutines, code segments, etc. The classifiers can be used to detect facial regions, facial features, and so on. As discussed above, the classifiers can be used to detect textures, gradients, color, shapes, edges, etc. Any classifier can be used for the analysis, including, but not limited to, density estimation, support vector machines (SVMs), logistic regression, classification trees, and so on. By way of example, consider facial features that can include the eyebrows 1040. One or more classifiers can be used to analyze the facial regions that can include the eyebrows to determine a probability for either a presence or an absence of an eyebrow furrow. The probability can include a posterior probability, a conditional probability, and so on. The probabilities can be based on Bayesian Statistics or another statistical analysis technique. The presence of an eyebrow furrow can indicate the person from whom the facial data was collected is annoyed, confused, unhappy, and so on. In another example, consider facial features that can include a mouth 1046. One or more classifiers can be used to analyze the facial region that can include the mouth to determine a probability for either a presence or an absence of mouth edges turned up to form a smile. Multiple classifiers can be used to determine one or more facial expressions.

Figure 11:
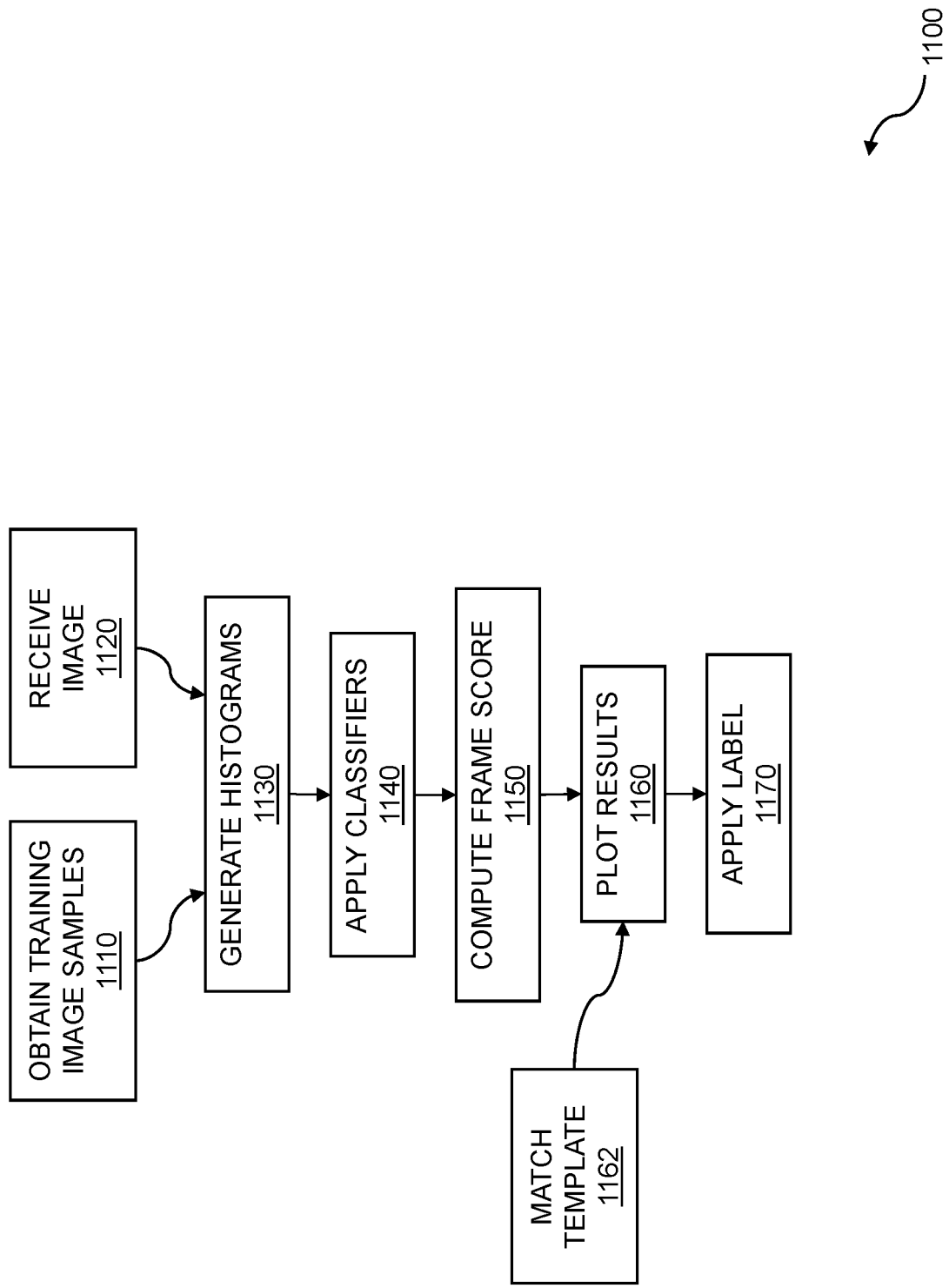
FIG. 11 is a flow diagram for detecting facial expressions.

FIG. 11 is a flow diagram for detecting facial expressions. The detecting facial expressions can enable vehicle video recommendation via affect. The flow 1100 can be used to automatically detect a wide range of facial expressions. A facial expression can produce strong emotional signals that can indicate valence and discrete emotional states. The discrete emotional states can include contempt, doubt, defiance, happiness, fear, anxiety, and so on. The detection of facial expressions can be based on the location of facial landmarks. The detection of facial expressions can be based on determination of action units (AUs) where the action units are determined using FACS coding. The AUs can be used singly or in combination to identify facial expressions. Based on the facial landmarks, one or more AUs can be identified by number and intensity. For example, AU12 can be used to code a lip corner puller and can be used to infer a smirk.

The flow 1100 begins by obtaining training image samples 1110. The image samples can include a plurality of images of one or more people. Human coders who are trained to correctly identify AU codes based on the FACS can code the images. The training or "known good" images can be used as a basis for training a machine learning technique. Once trained, the machine learning technique can be used to identify AUs in other images that can be collected using a camera, such as the camera 230 from FIG. 2, for example. The flow 1100 continues with receiving an image 1120. The image 1120 can be received from a camera, such as the camera 230 from FIG. 2, for example. As discussed above, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The image 1120 that is received can be manipulated in order to improve the processing of the image. For example, the image can be cropped, scaled, stretched, rotated, flipped, etc. in order to obtain a resulting image that can be analyzed more efficiently. Multiple versions of the same image can be analyzed. For example, the manipulated image and a flipped or mirrored version of the manipulated image can be analyzed alone and/or in combination to improve analysis. The flow 1100 continues with generating histograms 1130 for the training images and the one or more versions of the received image. The histograms can be generated for one or more versions of the manipulated received image. The histograms can be based on a HoG or another histogram. As described above, the HoG can include feature descriptors and can be computed for one or more regions of interest in the training images and the one or more received images. The regions of interest in the images can be located using facial landmark points, where the facial landmark points can include outer edges of nostrils, outer edges of the mouth, outer edges of eyes, etc. A HoG for a given region of interest can count occurrences of gradient orientation within a given section of a frame from a video, for example.

The flow 1100 continues with applying classifiers 1140 to the histograms. The classifiers can be used to estimate probabilities where the probabilities can correlate with an intensity of an AU or an expression. The choice of classifiers used is based on the training of a supervised learning technique to identify facial expressions, in some embodiments. The classifiers can be used to identify into which of a set of categories a given observation can be placed. For example, the classifiers can be used to determine a probability that a given AU or expression is present in a given image or frame of a video. In various embodiments, the one or more AUs that are present include AU01 inner brow raiser, AU12 lip corner puller, AU38 nostril dilator, and so on. In practice, the presence or absence of any number of AUs can be determined. The flow 1100 continues with computing a frame score 1150. The score computed for an image, where the image can be a frame from a video, can be used to determine the presence of a facial expression in the image or video frame. The score can be based on one or more versions of the image 1120 or manipulated image. For example, the score can be based on a comparison of the manipulated image to a flipped or mirrored version of the manipulated image. The score can be used to predict a likelihood that one or more facial expressions are present in the image. The likelihood can be based on computing a difference between the outputs of a classifier used on the manipulated image and on the flipped or mirrored image, for example. The classifier that is used can be used to identify symmetrical facial expressions (e.g. smile), asymmetrical facial expressions (e.g. outer brow raiser), and so on.

The flow 1100 continues with plotting results 1160. The results that are plotted can include one or more scores for one or more frames computed over a given time t. For example, the plotted results can include classifier probability results from analysis of HoGs for a sequence of images and video frames. The plotted results can be matched with a template 1162. The template can be temporal and can be represented by a centered box function or another function. A best fit with one or more templates can be found by computing a minimum error. Other best-fit techniques can include polynomial curve fitting, geometric curve fitting, and so on. The flow 1100 continues with applying a label 1170. The label can be used to indicate that a particular facial expression has been detected in the one or more images or video frames which constitute the image 1120. For example, the label can be used to indicate that any of a range of facial expressions has been detected, including a smile, an asymmetric smile, a frown, and so on. Various steps in the flow 1100 may be changed in order, repeated, omitted, or the like without departing from the disclosed concepts. Various embodiments of the flow 1100 may be included in a computer program product embodied in a non-transitory computer readable medium that includes code executable by one or more processors.

Figure 12:
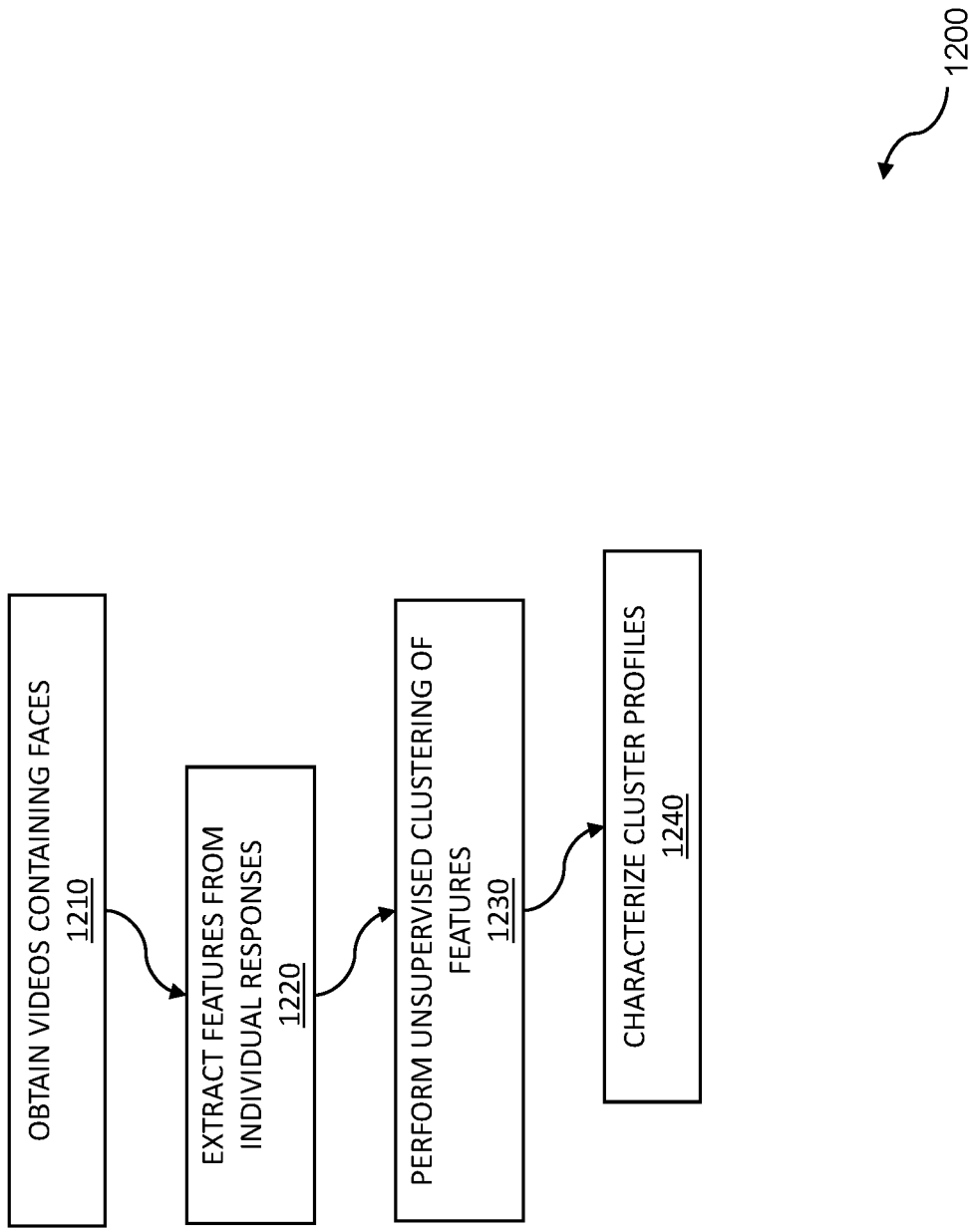
FIG. 12 is a flow diagram for large-scale clustering of facial events.

FIG. 12 is a flow diagram for large-scale clustering of facial events. As discussed throughout, cognitive state data, including video facial data, can be collected from one or more people. The collection of the facial video data from the one or more people can be accomplished using a web-based framework. The web-based framework can be used to collect video facial data from one or more vehicle occupants. The web-based framework can be used to collect facial video data from, for example, large numbers of people located over a wide geographic area. The web-based framework can enable vehicle video recommendation via affect. The web-based framework can include an opt-in feature that allows people to agree to facial data collection. The web-based framework can be used to render and display data to one or more people and can collect data from the one or more people. For example, the facial data collection can be based on showing one or more viewers a video media presentation through a website. The web-based framework can be used to display the video media presentation or event and to collect videos from any number of viewers who are online. That is, the collection of videos can be crowdsourced from those viewers who elected to opt-in to the video data collection. The video event can be a commercial, a political ad, an educational segment, and so on. The flow 1200 begins with obtaining videos containing faces 1210. The videos can be obtained using one or more cameras, where the cameras can include a webcam coupled to one or more devices employed by the one or more people using the web-based framework. The flow 1200 continues with extracting features from the individual responses 1220. The individual responses can include videos containing faces observed by the one or more webcams. The features that are extracted can include facial features such as an eyebrow, a nostril, an eye edge, a mouth edge, and so on. The feature extraction can be based on facial coding classifiers, where the facial coding classifiers output a probability that a specified facial action has been detected in a given video frame. The flow 1200 continues with performing unsupervised clustering of features 1230. The unsupervised clustering can be based on an event. The features can be extracted from compared cognitive state data. The unsupervised clustering can be based on a K-Means, where the K of the K-Means can be computed using a Bayesian Information Criterion (BICk), for example, to determine the smallest value of K that meets system requirements. Any other criterion for K can be used. The K-Means clustering technique can be used to group one or more events into various respective categories.

The flow 1200 continues with characterizing cluster profiles 1240. The profiles can include a variety of facial expressions such as smiles, asymmetric smiles, eyebrow raisers, eyebrow lowerers, etc. The profiles can be related to a given event. For example, a humorous video can be displayed in the web-based framework and the video data of people who have opted-in can be collected. The characterization of the collected and analyzed video can depend in part on the number of smiles that occurred at various points throughout the humorous video. Similarly, the characterization can be performed on collected and analyzed videos of people viewing a news presentation. The characterized cluster profiles can be further analyzed based on demographic data. For example, the number of smiles resulting from people viewing a humorous video can be compared to various demographic groups, where the groups can be formed based on geographic location, age, ethnicity, gender, and so on. Various steps in the flow 1200 may be changed in order, repeated, omitted, or the like without departing from the disclosed concepts. Various embodiments of the flow 1200 may be included in a computer program product embodied in a non-transitory computer readable medium that includes code executable by one or more processors.

Figure 13:
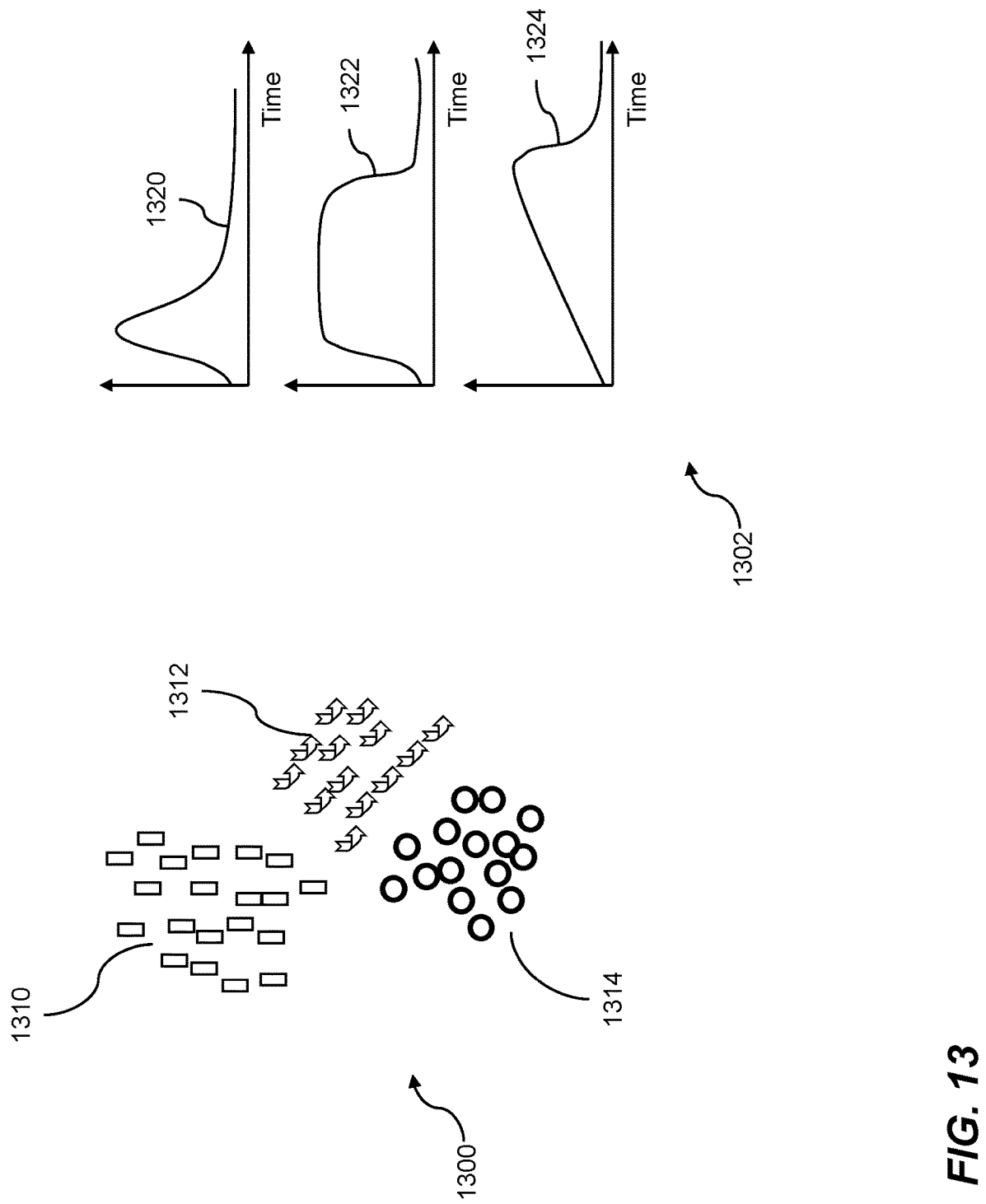
FIG. 13 shows example unsupervised clustering of features and characterizations of cluster profiles.

FIG. 13 shows example unsupervised clustering of features and characterization of cluster profiles. The clustering of features and characterization of cluster profiles can enable vehicle video recommendation via affect. Features including samples of facial data can be clustered using unsupervised clustering. Various clusters can be formed, which include similar groupings of facial data observations. The example 1300 shows three clusters: clusters 1310, 1312, and 1314. The clusters can be based on video collected from people who have opted-in to video collection. When the data collected is captured using a web-based framework, then the data collection can be performed on a grand scale, including hundreds, thousands, or even more participants who can be located locally and/or across a wide geographic area. Unsupervised clustering is a technique that can be used to process the large amounts of captured facial data and to identify groupings of similar observations. The unsupervised clustering can also be used to characterize the groups of similar observations. The characterizations can include identifying behaviors of the participants. The characterizations can be based on identifying facial expressions and facial action units of the participants. Some behaviors and facial expressions can include faster or slower onsets, faster or slower offsets, longer or shorter durations, etc. The onsets, offsets, and durations can all correlate to time. The data clustering that results from the unsupervised clustering can support data labeling. The labeling can include FACS coding. The clusters can be partially or totally based on a facial expression resulting from participants viewing a video presentation, where the video presentation can be an advertisement, a political message, educational material, a public service announcement, and so on. The clusters can be correlated with demographic information, where the demographic information can include educational level, geographic location, age, gender, income level, and so on.

Cluster profiles 1302 can be generated based on the clusters that can be formed from unsupervised clustering, with time shown on the x-axis and intensity or frequency shown on the y-axis. The cluster profiles can be based on captured facial data including facial expressions, for example. The cluster profile 1320 can be based on the cluster 1310, the cluster profile 1322 can be based on the cluster 1312, and the cluster profile 1324 can be based on the cluster 1314. The cluster profiles 1320, 1322, and 1324 can be based on smiles, smirks, frowns, or any other facial expression. Emotional states of the people who have opted in to video collection can be inferred by analyzing the clustered facial expression data. The cluster profiles can be plotted with respect to time and can show a rate of onset, a duration, and an offset (rate of decay). Other time-related factors can be included in the cluster profiles. The cluster profiles can be correlated with demographic information as described above.

Figure 14A:
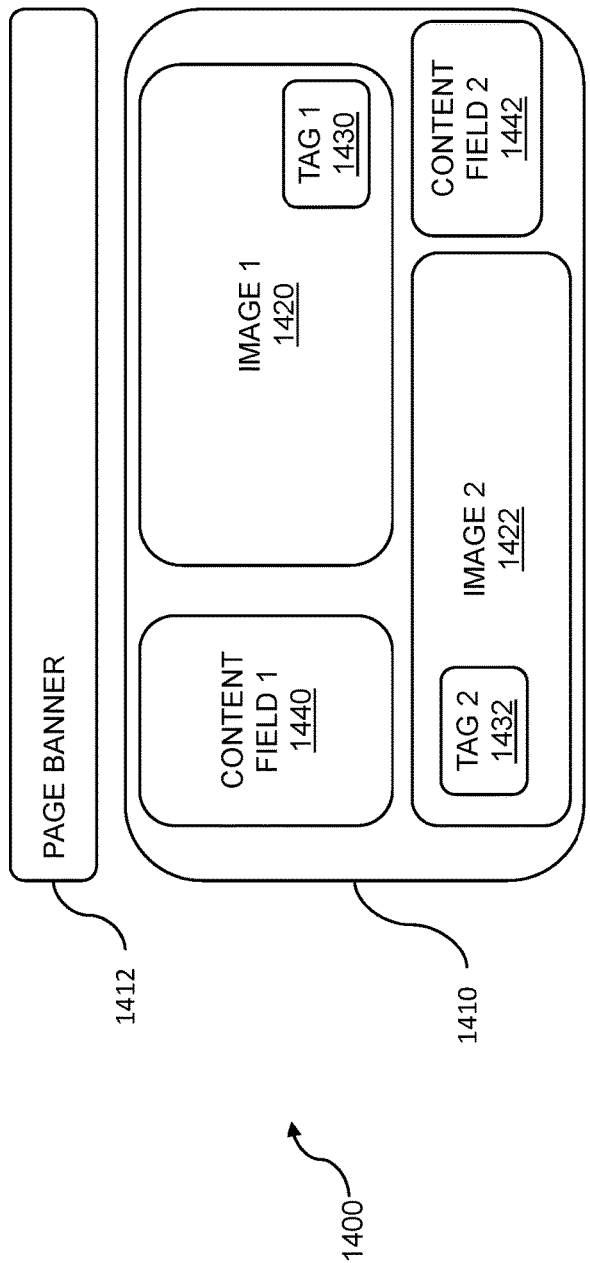
FIG. 14A shows example tags embedded in a webpage.

FIG. 14A shows example tags embedded in a webpage. A webpage can be displayed using a video client. The video client can include an app running on an electronic device such as a smartphone or tablet. Based on reactions by a viewer of the webpage, further recommendations of webpages, videos, etc., can be made to the viewer. Tags embedded in a webpage can support vehicle video recommendation via affect. A webpage 1400 can include a page body 1410, a page banner 1412, and so on. The page body can include one or more objects, where the objects can include text, images, videos, audio, and so on. The example page body 1410 shown includes a first image, image 1 1420; a second image, image 2 1422; a first content field, content field 1 1440; and a second content field, content field 2 1442. In practice, the page body 1410 can contain any number of images and content fields, and can include one or more videos, one or more audio presentations, and so on. The page body can include embedded tags, such as tag 1 1430 and tag 2 1432. In the example shown, tag 1 1430 is embedded in image 1 1420, and tag 2 1432 is embedded in image 2 1422. In embodiments, any number of tags is imbedded. Tags can also be embedded in content fields, in videos, in audio presentations, etc. When a user mouses over a tag or clicks on an object associated with a tag, the tag can be invoked. For example, when the user mouses over tag 1 1430, tag 1 1430 can then be invoked. Invoking tag 1 1430 can include enabling a camera coupled to a user's device and capturing one or more images of the user as the user views a media presentation (or digital experience). In a similar manner, when the user mouses over tag 2 1432, tag 2 1432 can be invoked. Invoking tag 2 1432 can also include enabling the camera and capturing images of the user. In other embodiments, other actions are taken based on invocation of the one or more tags. For example, invoking an embedded tag can initiate an analysis technique, post to social media, award the user a coupon or another prize, initiate cognitive state analysis, perform emotion analysis, and so on.

Figure 14B:
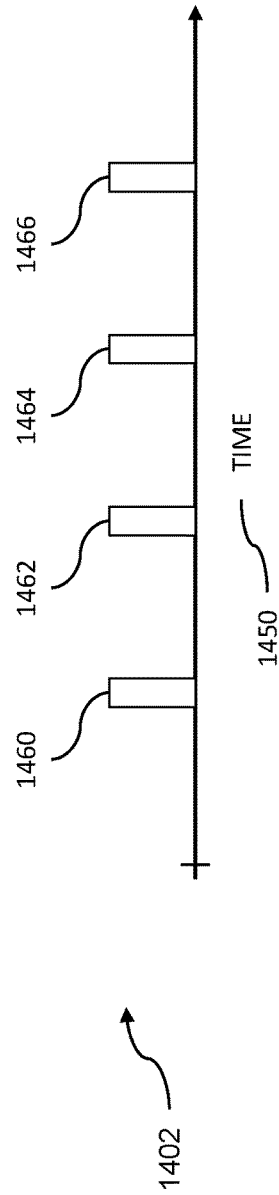
FIG. 14B shows example invoking tags for the collection of images.

FIG. 14B shows example tag invoking for the collection of images. As stated above, a media presentation can be a video, a webpage, and so on. A video 1402 can include one or more embedded tags, such as a tag 1460, another tag 1462, a third tag 1464, a fourth tag 1466, and so on. In practice, any number of tags can be included in the media presentation. The one or more tags can be invoked during the media presentation. The collection of the invoked tags can occur over time as represented by a timeline 1450. When a tag is encountered in the media presentation, the tag can be invoked. For example, when the tag 1460 is encountered, invoking the tag can enable a camera coupled to a user's device and can capture one or more images of the user viewing the media presentation. Invoking a tag can depend on opt-in by the user. For example, if a user has agreed to participate in a study by indicating an opt-in, then the camera coupled to the user's device can be enabled and one or more images of the user can be captured. If the user has not agreed to participate in the study and has not indicated an opt-in, then invoking the tag 1460 does not enable the camera or capture images of the user during the media presentation. The user can indicate an opt-in for certain types of participation, where opting in can be dependent on specific content in the media presentation. For example, the user could opt in to participate in a study of political campaign messages and not opt in for an advertisement study. In this case, tags that are related to political campaign messages and that enable the camera and image capture when invoked would be embedded in the media presentation. However, tags embedded in the media presentation that are related to advertisements would not enable the camera when invoked. Various other situations of tag invocation are possible.

Figure 15:
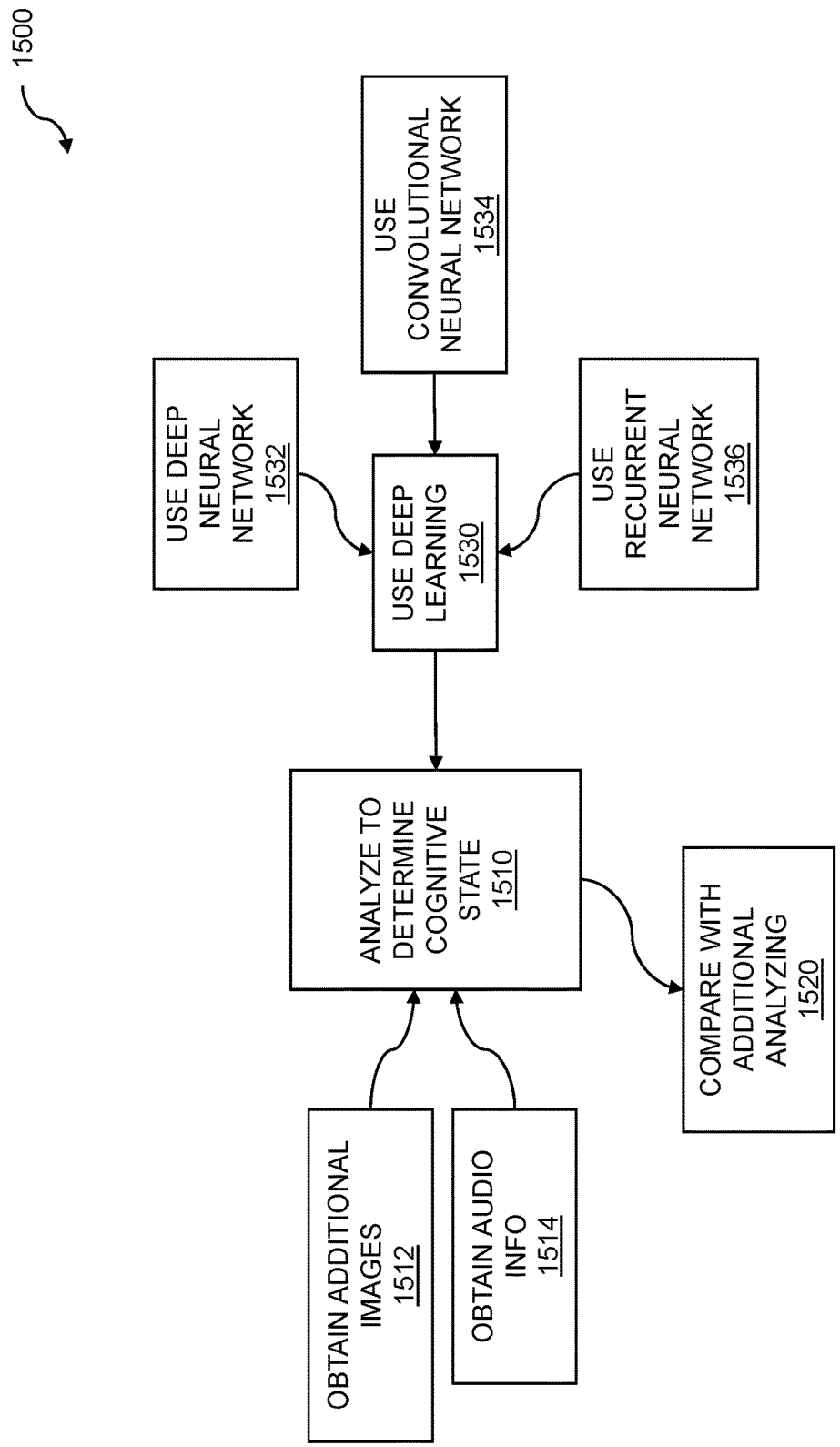
FIG. 15 is a flow diagram for further cognitive state analysis.

FIG. 15 is a flow diagram for further cognitive state analysis. Additional cognitive state data such as images, audio information, physiological information, and so on, can be obtained and analyzed to determine a cognitive state. The further cognitive state analysis supports vehicle video recommendation via affect. The cognitive state data can be captured from a vehicle occupant to whom a media presented is played. The cognitive state data can be ranked relative to another media presentation, and the cognitive state data can be correlated to cognitive state data collected from other people. One or more further media presentation selections can be recommended to the vehicle occupant. The further cognitive state analysis can be performed on a computing device. The computing device can include an on-vehicle computing device, an electronic device such as a smartphone or tablet computer associated with the vehicle occupant, and so on. The computing device can include a computing device located beyond the vehicle, where the computing device can include a computing device in another vehicle, a server, a blade server, a cloud server, a mesh server, and the like.

The flow 1500 includes obtaining additional images 1512 of one or more additional occupants of the vehicle, where the additional images are analyzed 1510 to determine one or more additional cognitive states. Images of the one or more additional occupants of the vehicle can be obtained using imaging devices within a vehicle. The images can include visible light images, near-infrared images, or images comprising other spectra, where the images of any type include facial data. The additional images can be captured or collected using a camera, a camera coupled to a mobile device, a camera coupled to a device on which a media presentation is played, and so on. In embodiments, the playing of the first media presentation is done on a mobile device, where the mobile device can be used for recording of facial images with the mobile device as part of the capturing of the cognitive state data. The additional vehicle occupants can occupy the vehicle contemporaneously with the vehicle occupant. The additional vehicle occupants can include one or more passengers, a custodial driver, and the like. In embodiments, the additional vehicle occupants can occupy one or more different vehicles from the vehicle of the vehicle occupant. The other vehicle occupants can be operators or passengers in vehicles adjacent to the first vehicle occupants. The flow 1500 includes obtaining audio information 1514 from the occupant of the vehicle and augmenting the analyzing based on the audio information. The audio information can be obtained using a microphone, audio transducer, etc., where the microphone, for example, can be an in-vehicle microphone, a microphone coupled to an electronic device associated with a vehicle occupant, etc. The microphone can obtain a variety of audio information such as in-vehicle sounds, exterior sounds such as road noise, wind noise, or traffic noise, etc. In embodiments, the audio information can include speech. The speech information can include speech from the occupant of the vehicle, speech detected in an audio source such as a radio or streaming station, and the like. In other embodiments, the audio information can include non-speech vocalizations. The non-speech vocalizations can include a variety of human generated sounds. In embodiments, the non-speech vocalizations can include grunts, yelps, squeals, snoring, sighs, laughter, filled pauses, unfilled pauses, or yawns.

The flow 1500 includes comparing the analyzing with additional analyzing 1520 performed on additional vehicle occupants. The comparing the analyzing can be used to determine an average cognitive state, an aggregate cognitive state, a range of cognitive states, and so on. The comparing can be used to determine whether the vehicle occupant is experiencing a cognitive state similar to or different from the other vehicle occupants. The additional cognitive states that can be determined by analyzing the additional images of the additional vehicle occupants can be used for adjusting the correlating the cognitive state. In embodiments, the flow can include obtaining physiological information from the occupant of the vehicle and augmenting the analyzing based on the physiological information. The physiological information can be inferred from image data or audio data, collected using cameras or sensors, and so on. The physiological information can include heart rate, heart rate variability, respiration rate, skin conductivity, and the like.

The flow 1500 includes analyzing, where the analyzing is performed using deep learning 1530. Deep learning can be based on learning one or more representations related to data, rather than relying on algorithms that can be specific to a given data analysis task. Data representations, such as those based on feature learning, include techniques for automating the discovery, by a deep learning system, of representations that can be used to classify or detect features in raw data. In embodiments, the learning is performed using a deep neural network 1532. A deep neural network can include an input layer, an output layer, and hidden layers internal to the neural network. A deep learning network can use weights, biases, and layers that can be learned as part of training the deep neural network. A deep neural network can include a feed-forward network, in which data such as training data or raw data can flow from an input layer, through the neural network, to an output layer. In other embodiments, the learning is performed using a convolutional neural network (CNN) 1534. A convolutional neural network can include properties such as space invariance, shift invariance, or translation invariance, which are properties that are particularly useful for image analysis. A CNN can require little preprocessing of input data because the CNN can learn filters. The learning the filters can obviate the need to code the filters. The filters can enhance image classification tasks such as facial data analysis. In further embodiments, the learning is performed using a recurrent neural network 1536. A recurrent neural network (RNN) can include connections between nodes to form a directed graph. The directed graph can be along a sequence. An RNN can exhibit temporal behavior by using storage internal to the RNN to process input data sequences. Various steps in the flow 1500 may be changed in order, repeated, omitted, or the like without departing from the disclosed concepts. Various embodiments of the flow 1500 can be included in a computer program product embodied in a non-transitory computer readable medium that includes code executable by one or more processors.

Figure 16:
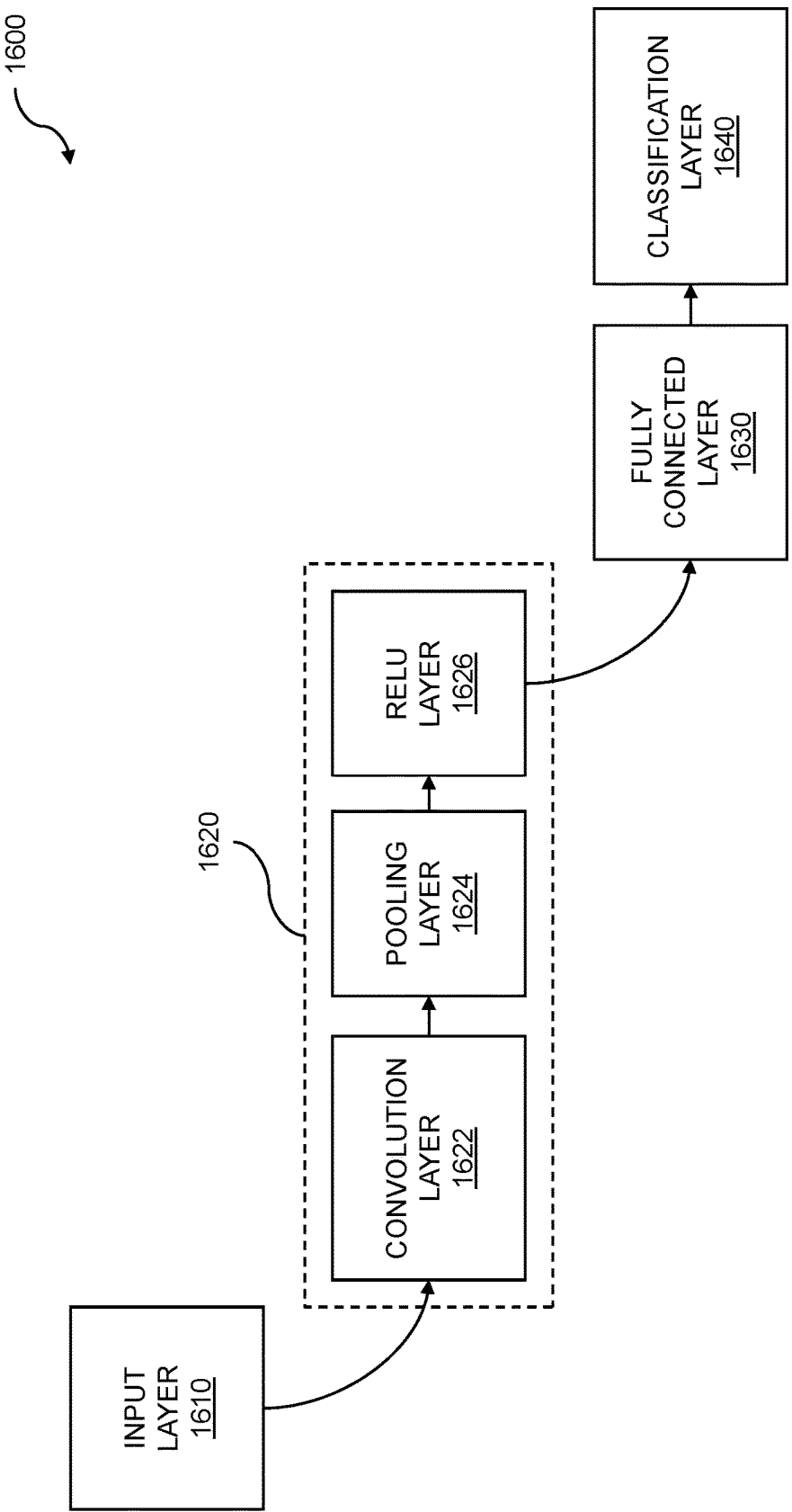
FIG. 16 is an example showing a convolutional neural network (CNN).

FIG. 16 is an example showing a convolutional neural network (CNN). A convolutional neural network such as 1600 can be used for deep learning, where the deep learning can be applied to vehicle video recommendation via affect. A first media presentation is played on a video client to a vehicle occupant. Cognitive state data for the vehicle occupant is captured, where the cognitive state data includes video facial data from the vehicle occupant during the first media presentation playing. An analysis server is used to rank the first media presentation relative to another media presentation based on the cognitive state data which was captured, where the ranking is for the vehicle occupant. The analysis server is used to correlate the cognitive state data to cognitive state data collected from other people who experienced the first media presentation. One or more further media presentation selections are recommended to the vehicle occupant, based on the ranking and the correlating. The convolutional neural network can be applied to analysis tasks such as cognitive state analysis, mood analysis, emotional state analysis, and so on. The CNN can be applied to recommendation tasks such as vehicle video recommendation. Cognitive state data can include mental processes, where the mental processes can include attention, creativity, memory, perception, problem solving, thinking, use of language, or the like.

Cognitive analysis is a very complex task. Understanding and evaluating moods, emotions, mental states, or cognitive states, requires a nuanced evaluation of facial expressions or other cues generated by people. Cognitive state analysis is important in many areas such as research, psychology, business, intelligence, law enforcement, and so on. The understanding of cognitive states can be useful for a variety of business purposes, such as improving marketing analysis, assessing the effectiveness of customer service interactions and retail experiences, and evaluating the consumption of content such as movies and videos. Identifying points of frustration in a customer transaction can allow a company to act to address the causes of the frustration. By streamlining processes, key performance areas such as customer satisfaction and customer transaction throughput can be improved, resulting in increased sales and revenues. In a content scenario, producing compelling content that achieves the desired effect (e.g. fear, shock, laughter, etc.) can result in increased ticket sales and/or increased advertising revenue. If a movie studio is producing a horror movie, it is desirable to know if the scary scenes in the movie are achieving the desired effect. By conducting tests in sample audiences, and analyzing faces in the audience, a computer-implemented method and system can process thousands of faces to assess the cognitive state at the time of the scary scenes. In many ways, such an analysis can be more effective than surveys that ask audience members questions, since audience members may consciously or subconsciously change answers based on peer pressure or other factors. However, spontaneous facial expressions can be more difficult to conceal. Thus, by analyzing facial expressions en masse in real time, important information regarding the general cognitive state of the audience can be obtained.

Analysis of facial expressions is also a complex task. Image data, where the image data can include facial data, can be analyzed to identify a range of facial expressions. The facial expressions can include a smile, frown, smirk, and so on. The image data and facial data can be processed to identify the facial expressions. The processing can include analysis of expression data, action units, gestures, mental states, cognitive states, physiological data, and so on. Facial data as contained in the raw video data can include information on one or more of action units, head gestures, smiles, brow furrows, squints, lowered eyebrows, raised eyebrows, attention, and the like. The action units can be used to identify smiles, frowns, and other facial indicators of expressions. Gestures can also be identified, and can include a head tilt to the side, a forward lean, a smile, a frown, as well as many other gestures. Other types of data including the physiological data can be collected, where the physiological data can be obtained using a camera or other image capture device, without contacting the person or persons. Respiration, heart rate, heart rate variability, perspiration, temperature, and other physiological indicators of cognitive state can be determined by analyzing the images and video data.

Deep learning is a branch of machine learning which seeks to imitate in software the activity which takes place in layers of neurons in the neocortex of the human brain. This imitative activity can enable software to "learn" to recognize and identify patterns in data, where the data can include digital forms of images, sounds, and so on. The deep learning software is used to simulate the large array of neurons of the neocortex. This simulated neocortex, or artificial neural network, can be implemented using mathematical formulas that are evaluated on processors. With the ever-increasing capabilities of the processors, increasing numbers of layers of the artificial neural network can be processed.

Deep learning applications include processing of image data, audio data, and so on. Image data applications include image recognition, facial recognition, etc. Image data applications can include differentiating dogs from cats, identifying different human faces, and the like. The image data applications can include identifying cognitive states, moods, mental states, emotional states, and so on, from the facial expressions of the faces that are identified. Audio data applications can include analyzing audio such as ambient room sounds, physiological sounds such as breathing or coughing, noises made by an individual such as tapping and drumming, voices, and so on. The voice data applications can include analyzing a voice for timbre, prosody, vocal register, vocal resonance, pitch, loudness, speech rate, or language content. The voice data analysis can be used to determine one or more cognitive states, moods, mental states, emotional states, etc.

The artificial neural network, such as a convolutional neural network which forms the basis for deep learning, is based on layers. The layers can include an input layer, a convolution layer, a fully connected layer, a classification layer, and so on. The input layer can receive input data such as image data, where the image data can include a variety of formats including pixel formats. The input layer can then perform processing tasks such as identifying boundaries of the face, identifying landmarks of the face, extracting features of the face, and/or rotating a face within the plurality of images. The convolution layer can represent an artificial neural network such as a convolutional neural network. A convolutional neural network can contain a plurality of hidden layers within it. A convolutional layer can reduce the amount of data feeding into a fully connected layer. The fully connected layer processes each pixel/data point from the convolutional layer. A last layer within the multiple layers can provide output indicative of cognitive state. The last layer of the convolutional neural network can be the final classification layer. The output of the final classification layer can be indicative of the cognitive states of faces within the images that are provided to the input layer.

Deep networks including deep convolutional neural networks can be used for facial expression parsing. A first layer of the deep network includes multiple nodes, where each node represents a neuron within a neural network. The first layer can receive data from an input layer. The output of the first layer can feed to a second layer, where the latter layer also includes multiple nodes. A weight can be used to adjust the output of the first layer which is being input to the second layer. Some layers in the convolutional neural network can be hidden layers. The output of the second layer can feed to a third layer. The third layer can also include multiple nodes. A weight can adjust the output of the second layer which is being input to the third layer. The third layer may be a hidden layer. Outputs of a given layer can be fed to the next layer. Weights adjust the output of one layer as it is fed to the next layer. When the final layer is reached, the output of the final layer can be a facial expression, a cognitive state, a mental state, a characteristic of a voice, and so on. The facial expression can be identified using a hidden layer from the one or more hidden layers. The weights can be provided on inputs to the multiple layers to emphasize certain facial features within the face. The convolutional neural network can be trained to identify facial expressions, voice characteristics, etc. The training can include assigning weights to inputs on one or more layers within the multilayered analysis engine. One or more of the weights can be adjusted or updated during training. The assigning weights can be accomplished during a feed-forward pass through the multilayered neural network. In a feed-forward arrangement, the information moves forward from the input nodes, through the hidden nodes, and on to the output nodes. Additionally, the weights can be updated during a backpropagation process through the multilayered analysis engine.

Returning to the figure, FIG. 16 is an example showing a convolutional neural network 1600. The convolutional neural network can be used for deep learning, where the deep learning can be applied to cognitive state-based vehicle manipulation using near-infrared image processing. The deep learning system can be accomplished using a convolution neural network or other techniques. The deep learning can accomplish facial recognition and analysis tasks. The network includes an input layer 1610. The input layer 1610 receives image data. The image data can be input in a variety of formats, such as JPEG, TIFF, BMP, and GIF. Compressed image formats can be decompressed into arrays of pixels, wherein each pixel can include an RGB tuple. The input layer 1610 can then perform processing such as identifying boundaries of the face, identifying landmarks of the face, extracting features of the face, and/or rotating a face within the plurality of images.

The network includes a collection of intermediate layers 1620. The multilayered analysis engine can include a convolutional neural network. Thus, the intermediate layers can include a convolution layer 1622. The convolution layer 1622 can include multiple sublayers, including hidden layers, within it. The output of the convolution layer 1622 feeds into a pooling layer 1624. The pooling layer 1624 performs a data reduction, which makes the overall computation more efficient. Thus, the pooling layer reduces the spatial size of the image representation to reduce the number of parameters and computations in the network. In some embodiments, the pooling layer is implemented using filters of size 2×2, applied with a stride of two samples for every depth slice along both width and height, resulting in a reduction of 75-percent of the downstream node activations. The multilayered analysis engine can further include a max pooling layer 1624. Thus, in embodiments, the pooling layer is a max pooling layer, in which the output of the filters is based on a maximum of the inputs. For example, with a 2×2 filter, the output is based on a maximum value from the four input values. In other embodiments, the pooling layer is an average pooling layer or L2-norm pooling layer. Various other pooling schemes are possible.

The intermediate layers can include a Rectified Linear Units (RELU) layer 1626. The output of the pooling layer 1624 can be input to the RELU layer 1626. In embodiments, the RELU layer implements an activation function such as $f(x)=\max(0,x)$, thus providing an activation with a threshold at zero. In some embodiments, the RELU layer 1626 is a leaky RELU layer. In this case, instead of the activation function providing zero when x<0, a small negative slope is used, resulting in an activation function such as $f(x)=1(x<0)(\alpha x)+1(x>=0)(x)$. This can reduce the risk of "dying RELU" syndrome, where portions of the network can be "dead" with nodes/neurons that do not activate across the training dataset. The image analysis can comprise training a multilayered analysis engine using the plurality of images, wherein the multilayered analysis engine can include multiple layers that include one or more convolutional layers 1622 and one or more hidden layers, and wherein the multilayered analysis engine can be used for emotional analysis.

The example 1600 includes a fully connected layer 1630. The fully connected layer 1630 processes each pixel/data point from the output of the collection of intermediate layers 1620. The fully connected layer 1630 takes all neurons in the previous layer and connects them to every single neuron it has. The output of the fully connected layer 1630 provides input to a classification layer 1640. The output of the classification layer 1640 provides a facial expression and/or cognitive state as its output. Thus, a multilayered analysis engine such as the one depicted in FIG. 16 processes image data using weights, models the way the human visual cortex performs object recognition and learning, and effectively analyzes image data to infer facial expressions and cognitive states.

Machine learning for generating parameters, analyzing data such as facial data and audio data, and so on, can be based on a variety of computational techniques. Generally, machine learning can be used for constructing algorithms and models. The constructed algorithms, when executed, can be used to make a range of predictions relating to data. The predictions can include whether an object in an image is a face, a box, or a puppy, whether a voice is female, male, or robotic, whether a message is legitimate email or a "spam" message, and so on. The data can include unstructured data and can be of large quantity. The algorithms that can be generated by machine learning techniques are particularly useful to data analysis because the instructions that comprise the data analysis technique do not need to be static. Instead, the machine learning algorithm or model, generated by the machine learning technique, can adapt. Adaptation of the learning algorithm can be based on a range of criteria such as success rate, failure rate, and so on. A successful algorithm is one that can adapt—or learn—as more data is presented to the algorithm. Initially, an algorithm can be "trained" by presenting it with a set of known data (supervised learning). Another approach, called unsupervised learning, can be used to identify trends and patterns within data. Unsupervised learning is not trained using known data prior to data analysis.

Reinforced learning is an approach to machine learning that is inspired by behaviorist psychology. The underlying premise of reinforced learning (also called reinforcement learning) is that software agents can take actions in an environment. The actions that are taken by the agents should maximize a goal such as a "cumulative reward". A software agent is a computer program that acts on behalf of a user or other program. The software agent is implied to have the authority to act on behalf of the user or program. The actions taken are decided by action selection to determine what to do next. In machine learning, the environment in which the agents act can be formulated as a Markov decision process (MDP). The MDPs provide a mathematical framework for modeling of decision making in environments where the outcomes can be partly random (stochastic) and partly under the control of the decision maker. Dynamic programming techniques can be used for reinforced learning algorithms. Reinforced learning is different from supervised learning in that correct input/output pairs are not presented, and suboptimal actions are not explicitly corrected. Rather, on-line or computational performance is the focus. On-line performance includes finding a balance between exploration of new (uncharted) territory or spaces and exploitation of current knowledge. That is, there is a tradeoff between exploration and exploitation.

Machine learning based on reinforced learning adjusts or learns based on learning an action, a combination of actions, and so on. An outcome results from taking an action. Thus, the learning model, algorithm, etc., learns from the outcomes that result from taking the action or combination of actions. The reinforced learning can include identifying positive outcomes, where the positive outcomes are used to adjust the learning models, algorithms, and so on. A positive outcome can be dependent on a context. When the outcome is based on a mood, emotional state, mental state, cognitive state, etc., of an individual, then a positive mood, emotion, mental state, or cognitive state can be used to adjust the model and algorithm. Positive outcomes can include the person being more engaged, where engagement is based on affect; the person spending more time playing an online game or navigating a webpage; the person converting by buying a product or service; and so on. The reinforced learning can be based on exploring a solution space and adapting the model, algorithm, etc., which stem from outcomes of the exploration. When positive outcomes are encountered, the positive outcomes can be reinforced by changing weighting values within the model, algorithm, etc. Positive outcomes may result in increasing weighting values. Negative outcomes can also be considered, where weighting values may be reduced or otherwise adjusted.

Figure 17:
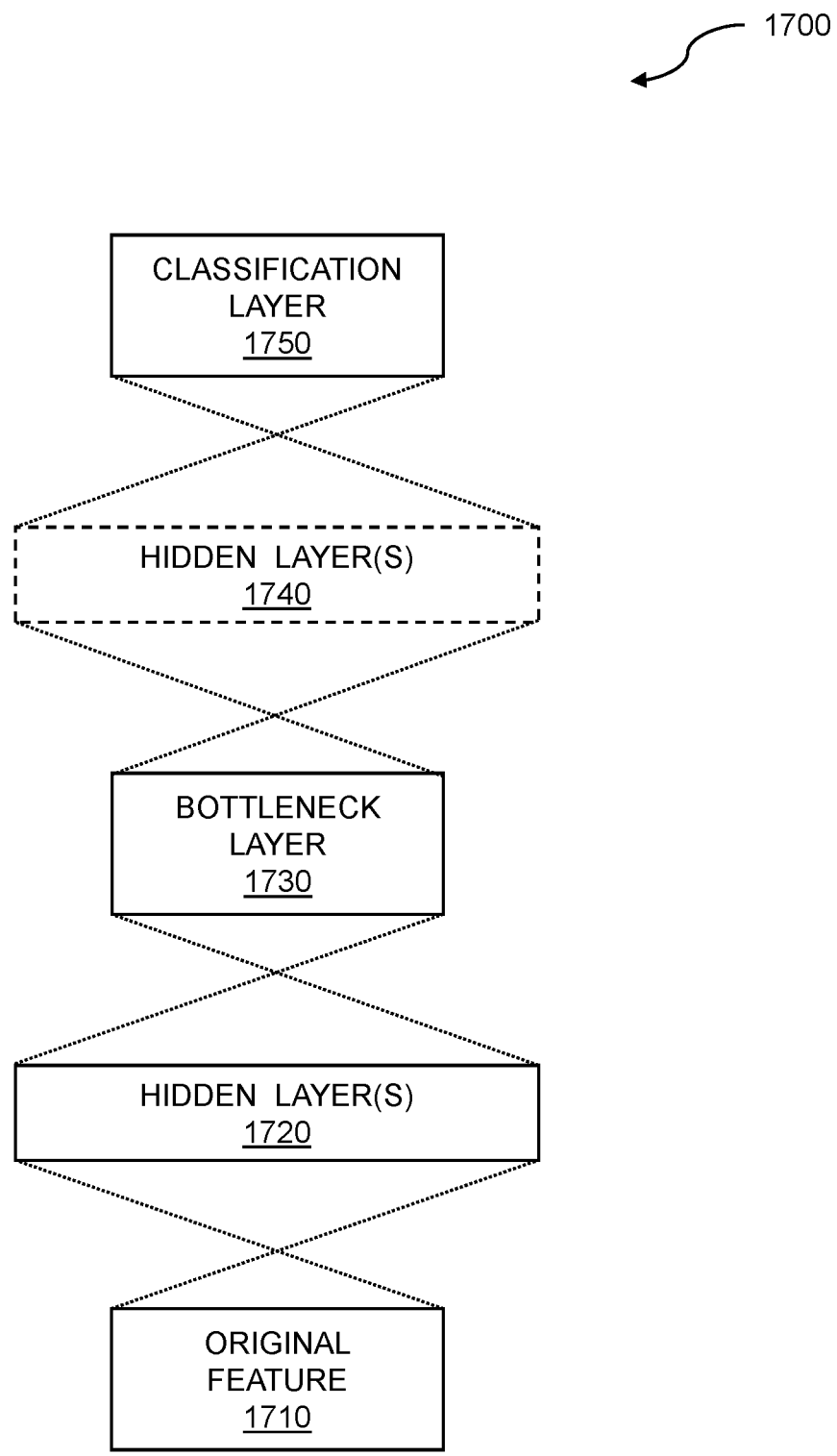
FIG. 17 illustrates a bottleneck layer within a deep learning environment.

FIG. 17 illustrates a bottleneck layer within a deep learning environment. A plurality of layers in a deep neural network (DNN) can include a bottleneck layer. The bottleneck layer can be used for vehicle video recommendation via affect. A deep neural network or other neural network can apply classifiers such as image classifiers, facial classifiers, audio classifiers, speech classifiers, physiological classifiers, and so on, to data captured or collected from an individual. The individual can include a vehicle occupant. The classifiers can be learned by analyzing cognitive state data. A video client can play a media presentation to a vehicle occupant. Cognitive state data, including facial data, is captured for the vehicle occupant during the first media presentation playing. An analysis server is used to rank the first media presentation relative to another media presentation, where the ranking is for the vehicle occupant. The analysis server is used to correlate the cognitive state data to cognitive state data collected from other people who experienced the first media presentation. One or more further media presentation selections are recommended to the vehicle occupant based on the ranking and the correlating.

Layers of a deep neural network can include a bottleneck layer 1700. A bottleneck layer can be used for a variety of applications such as facial recognition, voice recognition, emotional state recognition, and so on. The deep neural network in which the bottleneck layer is located can include a plurality of layers. The plurality of layers can include an original feature layer 1710. A feature such as an image feature can include points, edges, objects, boundaries between and among regions, properties, and so on. The deep neural network can include one or more hidden layers 1720. The one or more hidden layers can include nodes, where the nodes can include nonlinear activation functions and other techniques. The bottleneck layer can be a layer that learns translation vectors to transform a neutral face to an emotional or expressive face. In some embodiments, the translation vectors can transform a neutral sounding voice to an emotional or expressive voice. Specifically, activations of the bottleneck layer determine how the transformation occurs. A single bottleneck layer can be trained to transform a neutral face or voice to an emotional face or voice. In some cases, an individual bottleneck layer can be trained for a transformation pair. At runtime, once the user's emotion has been identified and an appropriate response to it can be determined (mirrored or complementary), the trained bottleneck layer can be used to perform the needed transformation.

The deep neural network can include a bottleneck layer 1730. The bottleneck layer can include a fewer number of nodes than the one or more preceding hidden layers. The bottleneck layer can create a constriction in the deep neural network or other network. The bottleneck layer can force information that is pertinent to a classification, for example, into a low dimensional representation. The bottleneck features can be extracted using an unsupervised technique. In other embodiments, the bottleneck features can be extracted using a supervised technique. The supervised technique can include training the deep neural network with a known dataset. The features can be extracted from an autoencoder such as a variational autoencoder, a generative autoencoder, and so on. The deep neural network can include hidden layers 1740. The number of the hidden layers can include zero hidden layers, one hidden layer, a plurality of hidden layers, and so on. The hidden layers following the bottleneck layer can include more nodes than the bottleneck layer. The deep neural network can include a classification layer 1750. The classification layer can be used to identify the points, edges, objects, boundaries, and so on, described above. The classification layer can be used to identify cognitive states, mental states, emotional states, moods, and the like. The output of the final classification layer can be indicative of the emotional states of faces within the images, where the images can be processed using the deep neural network.

Figure 18:
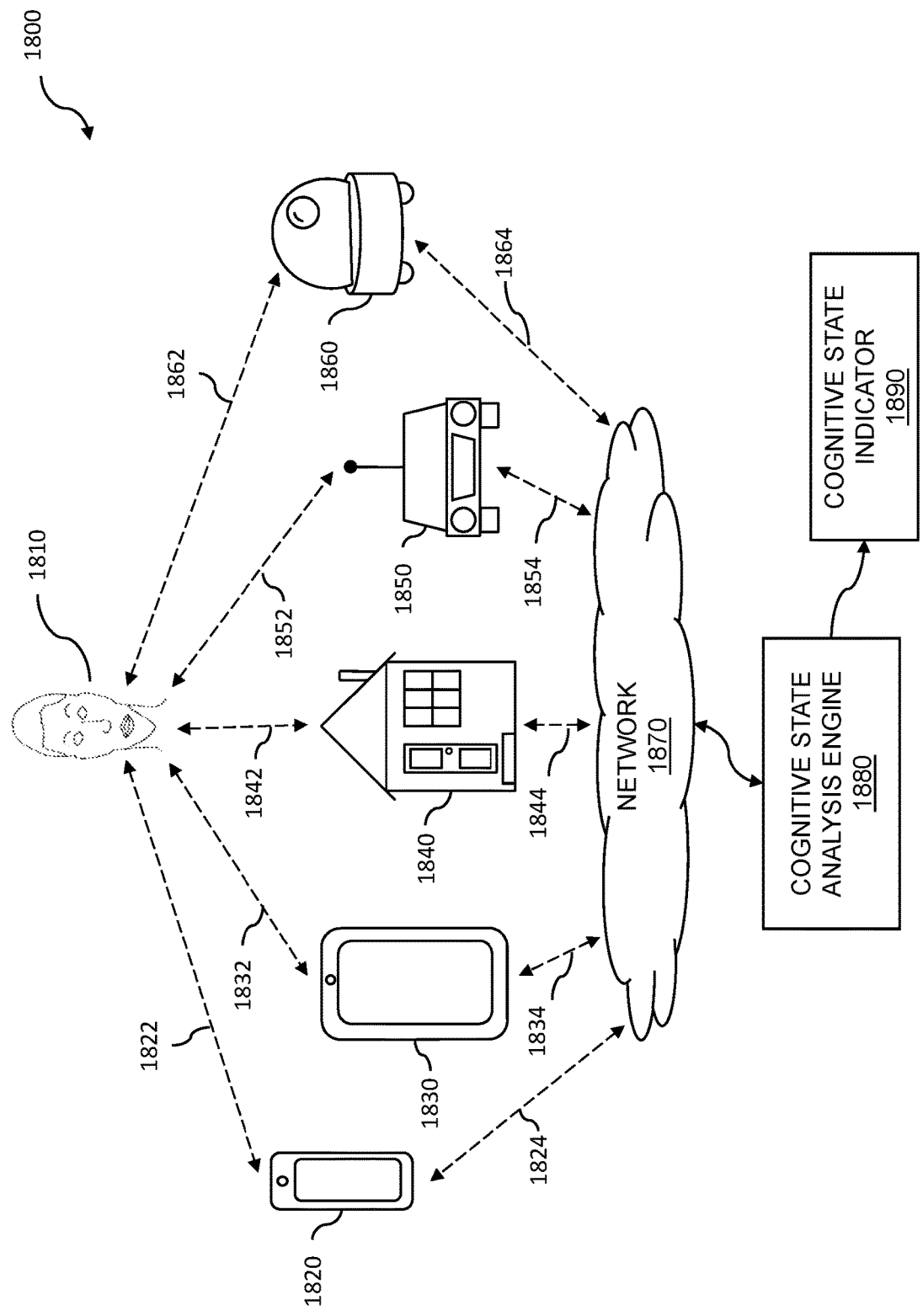
FIG. 18 shows data collection including devices and locations.

FIG. 18 shows data collection including devices and locations 1800. Data, including video data, audio data and physio data, can be obtained for vehicle video recommendation via affect. The data can be obtained from multiple devices, vehicles, and locations. A video client is used to play a first media presentation to a vehicle occupant. Cognitive state data is captured for the vehicle occupant, where the cognitive state data includes video facial data from the vehicle occupant during the first media presentation playing. The images can include visible light-based images and near-infrared based images. An analysis server is used to rank the first media presentation relative to another media presentation based on the cognitive state data which was captured for the vehicle occupant, where the ranking is for the vehicle occupant. The analysis server is used to correlate the cognitive state data, which was captured for the vehicle occupant, to cognitive state data collected from other people who experienced the first media presentation. One or more further media presentation selections are recommended to the vehicle occupant based on the ranking and the correlating.

The multiple mobile devices, vehicles, and locations 1800 can be used separately or in combination to collect video data on a user 1810. The video data can include facial data. Other data such as audio data, physiological data, and so on, can be collected on the user. While one person is shown, the video data, or other data, can be collected on multiple people. A user 1810 can be observed as she or he is performing a task, experiencing an event, viewing a media presentation, and so on. The user 1810 can be shown one or more media presentations, political presentations, social media, or another form of displayed media. The one or more media presentations can be shown to a plurality of people. The media presentations can be displayed on an electronic display coupled to a client device. The data collected on the user 1810 or on a plurality of users can be in the form of one or more videos, video frames, still images, etc. The plurality of videos can be of people who are experiencing different situations. Some example situations can include the user or plurality of users being exposed to TV programs, movies, video clips, social media, social sharing, and other such media. The situations could also include exposure to media such as advertisements, political messages, news programs, and so on. As previously noted, video data can be collected on one or more users in substantially identical or different situations and viewing either a single media presentation or a plurality of presentations. The data collected on the user 1810 can be analyzed and viewed for a variety of purposes including expression analysis, mental state analysis, cognitive state analysis, and so on. The electronic display can be on a smartphone 1820 as shown, a tablet computer 1830, a personal digital assistant, a television, a mobile monitor, or any other type of electronic device. In one embodiment, expression data is collected on a mobile device such as a cell phone 1820, a tablet computer 1830, a laptop computer, or a watch. Thus, the multiple sources can include at least one mobile device, such as a phone 1820 or a tablet 1830, or a wearable device such as a watch or glasses (not shown). A mobile device can include a front-side camera and/or a back-side camera that can be used to collect expression data. Sources of expression data can include a webcam, a phone camera, a tablet camera, a wearable camera, and a mobile camera. A wearable camera can comprise various camera devices, such as a watch camera. In addition to using client devices for data collection from the user 1810, data can be collected in a house 1840 using a web camera or the like; in a vehicle 1850 using a web camera, client device, etc.; by a social robot 1860, and so on.

As the user 1810 is monitored, the user 1810 might move due to the nature of the task, boredom, discomfort, distractions, or for another reason. As the user moves, the camera with a view of the user's face can be changed. Thus, as an example, if the user 1810 is looking in a first direction, the line of sight 1822 from the smartphone 1820 is able to observe the user's face, but if the user is looking in a second direction, the line of sight 1832 from the tablet 1830 is able to observe the user's face. Furthermore, in other embodiments, if the user is looking in a third direction, the line of sight 1842 from a camera in the house 1840 is able to observe the user's face, and if the user is looking in a fourth direction, the line of sight 1852 from the camera in the vehicle 1850 is able to observe the user's face. If the user is looking in a fifth direction, the line of sight 1862 from the social robot 1860 is able to observe the user's face. If the user is looking in a sixth direction, a line of sight from a wearable watch-type device, with a camera included on the device, is able to observe the user's face. In other embodiments, the wearable device is another device, such as an earpiece with a camera, a helmet or hat with a camera, a clip-on camera attached to clothing, or any other type of wearable device with a camera or other sensor for collecting expression data. The user 1810 can also use a wearable device including a camera for gathering contextual information and/or collecting expression data on other users. Because the user 1810 can move her or his head, the facial data can be collected intermittently when she or he is looking in a direction of a camera. In some cases, multiple people can be included in the view from one or more cameras, and some embodiments include filtering out faces of one or more other people to determine whether the user 1810 is looking toward a camera. All or some of the expression data can be continuously or sporadically available from the various devices and other devices.

The captured video data can include cognitive content, such as facial expressions, etc., and can be transferred over a network 1870. The network can include the Internet or other computer network. The smartphone 1820 can share video using a link 1824, the tablet 1830 using a link 1834, the house 1840 using a link 1844, the vehicle 1850 using a link 1854, and the social robot 1860 using a link 1864. The links 1824, 1834, 1844, 1854, and 1864 can be wired, wireless, and hybrid links. The captured video data, including facial expressions, can be analyzed on a cognitive state analysis engine 1880, on a computing device such as the video capture device, or on another separate device. The analysis could take place on one of the mobile devices discussed above, on a local server, on a remote server, and so on. In embodiments, some of the analysis takes place on the mobile device, while other analysis takes place on a server device. The analysis of the video data can include the use of a classifier. The video data can be captured using one of the mobile devices discussed above and sent to a server or another computing device for analysis. However, the captured video data including expressions can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device different from the capture device. The analysis data from the cognitive state analysis engine can be processed by a cognitive state indicator 1890. The cognitive state indicator 1890 can indicate cognitive states, mental states, moods, emotions, etc. In embodiments, the cognitive state can include drowsiness, fatigue, distraction, impairment, sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth.

Figure 19:
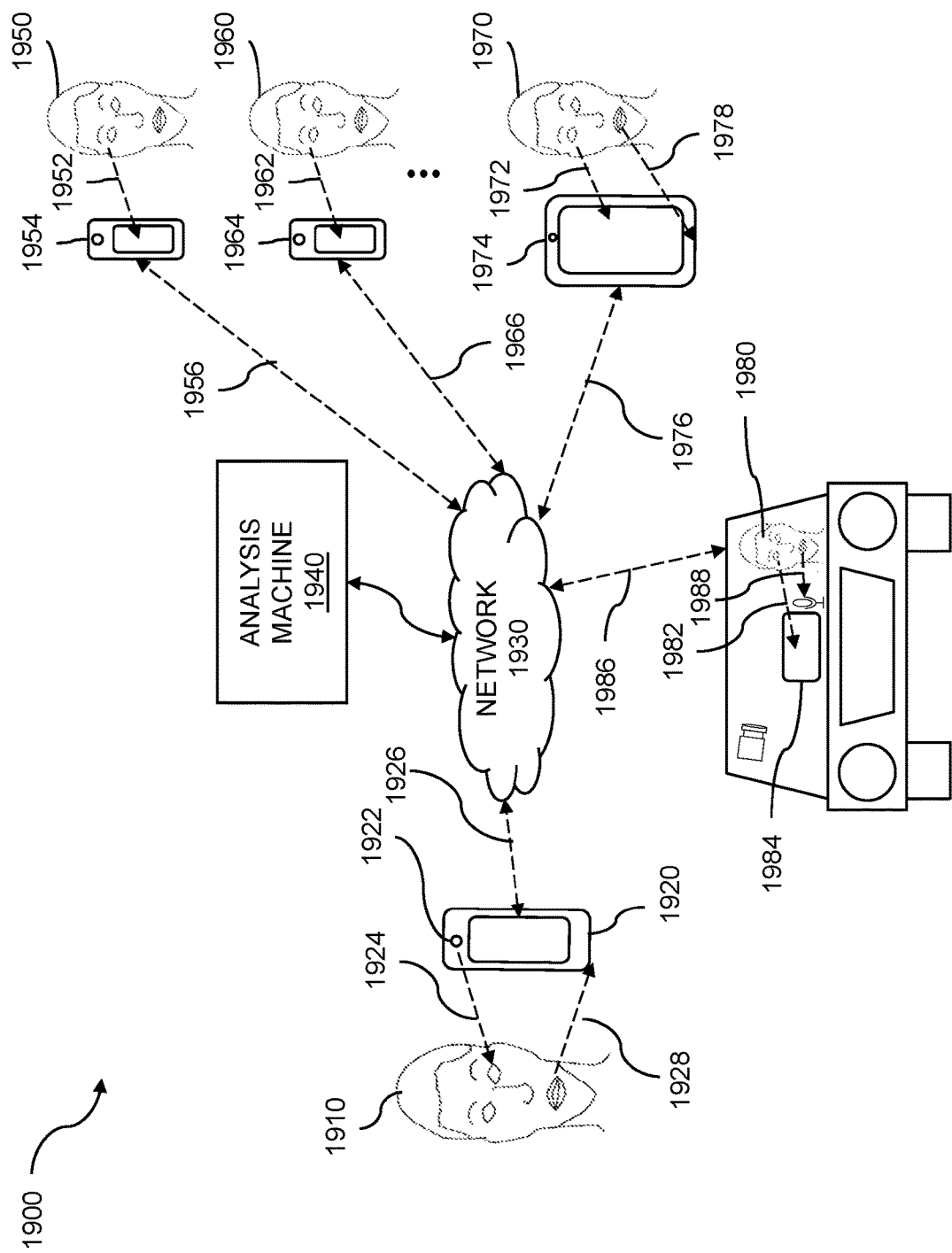
FIG. 19 illustrates an example of live streaming of social video and audio.

FIG. 19 illustrates an example of live streaming of social video and audio. The streaming of social video and social audio can be applied to vehicle video recommendation via affect. The live streaming can include cognitive state data, image data, facial data, speech data, audio data, physiological data, etc. A first media presentation is played on a video client to a vehicle occupant. Cognitive state data for the vehicle occupant is captured, where the cognitive state data includes video facial data from the vehicle occupant during the first media presentation playing. An analysis server is used to rank the first media presentation relative to another media presentation based on the cognitive state data which was captured for the vehicle occupant, where the ranking is for the vehicle occupant. The analysis server is used to correlate the cognitive state data which was captured for the vehicle occupant to cognitive state data collected from other people who experienced the first media presentation. One or more further media presentation selections are recommended to the vehicle occupant based on the ranking and the correlating.

The live streaming and image analysis 1900 can be facilitated by a video capture device, a local server, a remote server, semiconductor-based logic, and so on. The streaming can be live streaming and can include cognitive state analysis, cognitive state event signature analysis, etc. Live streaming video is an example of one-to-many social media, where video can be sent over the Internet from one person to a plurality of people using a social media app and/or platform. Live streaming is one of numerous popular techniques used by people who want to disseminate ideas, send information, provide entertainment, share experiences, and so on. Some of the live streams, such as webcasts, online classes, sporting events, news, computer gaming, or video conferences can be scheduled, while others can be impromptu streams that are broadcast as needed or when desired. Examples of impromptu live stream videos can range from individuals simply wanting to share experiences with their social media followers, to live coverage of breaking news, emergencies, or natural disasters. The latter coverage is known as mobile journalism, or "mo jo", and is becoming increasingly common. With this type of coverage, news reporters can use networked, portable electronic devices to provide mobile journalism content to a plurality of social media followers. Such reporters can be quickly and inexpensively deployed as the need or desire arises.

Several live streaming social media apps and platforms can be used for transmitting video. One such video social media app is Meerkat™ which can link with a user's Twitter™ account. Meerkat™ enables a user to stream video using a handheld, networked electronic device coupled to video capabilities. Viewers of the live stream can comment on the stream using tweets that can be seen and responded to by the broadcaster. Another popular app is Periscope™ which can transmit a live recording from one user to his or her Periscope™ account and to other followers. The Periscope™ app can be executed on a mobile device. The user's Periscope™ followers can receive an alert whenever that user begins a video transmission. Another live-stream video platform is Twitch™ which can be used for video streaming of video gaming and broadcasts of various competitions and events.

The example 1900 shows a user 1910 broadcasting a video live stream and an audio live stream to one or more people as shown by a first person 1950, a second person 1960, and a third person 1970. A portable, network-enabled, electronic device 1920 can be coupled to a front-side camera 1922. The portable electronic device 1920 can be a smartphone, a PDA, a tablet, a laptop computer, and so on. The camera 1922 coupled to the device 1920 can have a line-of-sight view 1924 to the user 1910 and can capture video of the user 1910. The portable electronic device 1920 can be coupled to a microphone (not shown). The microphone can capture voice data 1928 such as speech and non-speech vocalizations. In embodiments, non-speech vocalizations can include grunts, yelps, squeals, snoring, sighs, laughter, filled pauses, unfilled pauses, yawns, or the like. The captured video and audio can be sent to an analysis or recommendation engine 1940 using a network link 1926 to the network 1930. The network link can be a wireless link, a wired link, and so on. The recommendation engine 1940 can recommend to the user 1910 an app and/or platform that can be supported by the server and can be used to provide a video live stream, an audio live stream, or both a video live stream and an audio live stream to one or more followers of the user 1910.

In the example 1900, the user 1910 has four followers: a first person 1950, a second person 1960, a third person 1970, and a fourth person 1980. Each follower has a line-of-sight view to a video screen on a portable, networked electronic device. In other embodiments, one or more followers follow the user 1910 using any other networked electronic device, including a computer. In the example 1900, a first person 1950 has a line-of-sight view 1952 to the video screen of a device 1954; a second person 1960 has a line-of-sight view 1962 to the video screen of a device 1964, a third person 1970 has a line-of-sight view 1972 to the video screen of a device 1974, and a fourth person 1980 has a line-of-sight view 1982 to the video screen of a device 1984. The device 1974 can also capture audio data 1978 from the third person 1970, and the device 1984 can further capture audio data 1988 from the fourth person 1980. The portable electronic devices 1954, 1964, 1974, and 1984 can each be a smartphone, a PDA, a tablet, and so on. Each portable device can receive the video stream and the audio stream being broadcast by the user 1910 through the network 1930 using the app and/or platform that can be recommended by the recommendation engine 1940. The network can include the Internet, a computer network, a cellular network, and the like. The device 1954 can receive a video stream and an audio stream using the network link 1956, the device 1964 can receive a video stream and an audio stream using the network link 1966, the device 1974 can receive a video stream and an audio stream using the network link 1976, the device 1984 can receive a video stream and an audio stream using the network link 1986, and so on. The network link can be a wireless link, a wired link, a hybrid link, and the like. Depending on the app and/or platform that can be recommended by the analysis engine 1940, one or more followers, such as the followers shown 1950, 1960, 1970, and 1980, can reply to, comment on, or otherwise provide feedback to the user 1910 using their respective devices 1954, 1964, 1974, and 1984.

The human face provides a powerful communications medium through its ability to exhibit numerous expressions that can be captured and analyzed for a variety of purposes. In some cases, media producers are acutely interested in evaluating the effectiveness of message delivery by video media. Such video media includes advertisements, political messages, educational materials, television programs, movies, government service announcements, etc. Automated facial analysis can be performed on one or more video frames containing a face in order to detect facial action. Based on the facial action detected, a variety of parameters can be determined, including affect valence, spontaneous reactions, facial action units, and so on. The parameters that are determined can be used to infer or predict emotional, mental, and cognitive states. For example, determined valence can be used to describe the emotional reaction of a viewer to a video media presentation or another type of presentation. Positive valence provides evidence that a viewer is experiencing a favorable emotional response to the video media presentation, while negative valence provides evidence that a viewer is experiencing an unfavorable emotional response to the video media presentation. Other facial data analysis can include the determination of discrete emotional states of the viewer or viewers.

Facial data can be collected from a plurality of people using any of a variety of cameras. A camera can include a webcam, a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. In some embodiments, the person is permitted to "opt in" to the facial data collection. For example, the person can agree to the capture of facial data using a personal device such as a mobile device or another electronic device by selecting an opt-in choice. Opting-in can then turn on the person's webcam-enabled device and can begin the capture of the person's facial data via a video feed from the webcam or other camera. The video data that is collected can include one or more persons experiencing an event. The one or more persons can be sharing a personal electronic device, or can each be using one or more devices for video capture. The videos that are collected can be collected using a web-based framework. The web-based framework can be used to display the video media presentation or event as well as to collect videos from multiple viewers who are online. That is, the collection of videos can be crowdsourced from those viewers who elected to opt in to the video data collection.

The videos captured from the various viewers who chose to opt in can be substantially different in terms of video quality, frame rate, etc. As a result, the facial video data can be scaled, rotated, and otherwise adjusted to improve consistency. Human factors further contribute to the capture of the facial video data. The facial data that is captured might or might not be relevant to the video media presentation being displayed. For example, the viewer might not be paying attention, might be fidgeting, might be distracted by an object or event near the viewer, or might be otherwise inattentive to the video media presentation. The behavior exhibited by the viewer can prove challenging to analyze due to viewer actions including eating, speaking to another person or persons, speaking on the phone, etc. The videos collected from the viewers might also include other artifacts that pose challenges during the analysis of the video data. The artifacts can include items such as eyeglasses (because of reflections), eye patches, jewelry, and clothing that occlude or obscure the viewer's face. Similarly, a viewer's hair or hair covering can present artifacts by obscuring the viewer's eyes and/or face.

The captured facial data can be analyzed using the facial action coding system (FACS). The FACS seeks to define groups or taxonomies of facial movements of the human face. The FACS encodes movements of individual muscles of the face, where the muscle movements often include slight, instantaneous changes in facial appearance. The FACS encoding is commonly performed by trained observers, but can also be performed on automated, computer-based systems. Analysis of the FACS encoding can be used to determine emotions of the persons whose facial data is captured in the videos. The FACS is used to encode a wide range of facial expressions that are anatomically possible for the human face. The FACS encodings include action units (AUs) and related temporal segments that are based on the captured facial expression. The AUs are open to higher order interpretation and decision-making. These AUs can be used to recognize emotions experienced by the person who is being observed. Emotion-related facial actions can be identified using the emotional facial action coding system (EM-FACS) and the facial action coding system affect interpretation dictionary (FACSAID). For a given emotion, specific action units can be related to the emotion. For example, the emotion of anger can be related to AUs 4, 5, 7, and 23, while happiness can be related to AUs 6 and 12. Other mappings of emotions to AUs have also been previously associated. The coding of the AUs can include an intensity scoring that ranges from A (trace) to E (maximum). The AUs can be used for analyzing images to identify patterns indicative of a particular cognitive and/or emotional state. The AUs range in number from 0 (neutral face) to 98 (fast up-down look). The AUs include so-called main codes (inner brow raiser, lid tightener, etc.), head movement codes (head turn left, head up, etc.), eye movement codes (eyes turned left, eyes up, etc.), visibility codes (eyes not visible, entire face not visible, etc.), and gross behavior codes (sniff, swallow, etc.). Emotion scoring can be included where intensity is evaluated, and specific emotions, moods, mental states, or cognitive states can be identified.

The coding of faces identified in videos captured of people observing an event can be automated. The automated systems can detect facial AUs or discrete emotional states. The emotional states can include amusement, fear, anger, disgust, surprise, and sadness. The automated systems can be based on a probability estimate from one or more classifiers, where the probabilities can correlate with an intensity of an AU or an expression. The classifiers can be used to identify into which of a set of categories a given observation can be placed. In some cases, the classifiers can be used to determine a probability that a given AU or expression is present in a given frame of a video. The classifiers can be used as part of a supervised machine learning technique, where the machine learning technique can be trained using "known good" data. Once trained, the machine learning technique can proceed to classify new data that is captured.

The supervised machine learning models can be based on support vector machines (SVMs). An SVM can have an associated learning model that is used for data analysis and pattern analysis. For example, an SVM can be used to classify data that can be obtained from collected videos of people experiencing a media presentation. An SVM can be trained using "known good" data that is labeled as belonging to one of two categories (e.g. smile and no-smile). The SVM can build a model that assigns new data into one of the two categories. The SVM can construct one or more hyperplanes that can be used for classification. The hyperplane that has the largest distance from the nearest training point can be determined to have the best separation. The largest separation can improve the classification technique by increasing the probability that a given data point can be properly classified.

In another example, a histogram of oriented gradients (HoG) can be computed. The HoG can include feature descriptors and can be computed for one or more facial regions of interest. The regions of interest of the face can be located using facial landmark points, where the facial landmark points can include outer edges of nostrils, outer edges of the mouth, outer edges of eyes, etc. A HoG for a given region of interest can count occurrences of gradient orientation within a given section of a frame from a video, for example. The gradients can be intensity gradients and can be used to describe an appearance and a shape of a local object. The HoG descriptors can be determined by dividing an image into small, connected regions, also called cells. A histogram of gradient directions or edge orientations can be computed for pixels in the cell. Histograms can be contrast-normalized based on intensity across a portion of the image or the entire image, thus reducing any influence from differences in illumination or shadowing changes between and among video frames. The HoG can be computed on the image or on an adjusted version of the image, where the adjustment of the image can include scaling, rotation, etc. The image can be adjusted by flipping the image around a vertical line through the middle of a face in the image. The symmetry plane of the image can be determined from the tracker points and landmarks of the image.

In embodiments, an automated facial analysis system identifies five facial actions or action combinations in order to detect spontaneous facial expressions for media research purposes. Based on the facial expressions that are detected, a determination can be made with regard to the effectiveness of a given video media presentation, for example. The system can detect the presence of the AUs or the combination of AUs in videos collected from a plurality of people. The facial analysis technique can be trained using a web-based framework to crowdsource videos of people as they watch online video content. The video can be streamed at a fixed frame rate to a server. Human labelers can code for the presence or absence of facial actions including a symmetric smile, unilateral smile, asymmetric smile, and so on. The trained system can then be used to automatically code the facial data collected from a plurality of viewers experiencing video presentations (e.g. television programs).

Spontaneous asymmetric smiles can be detected in order to understand viewer experiences. Related literature indicates that as many asymmetric smiles occur on the right hemi face as do on the left hemi face, for spontaneous expressions. Detection can be treated as a binary classification problem, where images that contain a right asymmetric expression are used as positive (target class) samples and all other images as negative (non-target class) samples. Classifiers perform the classification, including classifiers such as support vector machines (SVMs) and random forests. Random forests can include ensemble-learning methods that use multiple learning algorithms to obtain better predictive performance. Frame-by-frame detection can be performed to recognize the presence of an asymmetric expression in each frame of a video. Facial points can be detected, including the top of the mouth and the two outer eye corners. The face can be extracted, cropped, and warped into a pixel image of specific dimension (e.g. 96×96 pixels). In embodiments, the inter-ocular distance and vertical scale in the pixel image are fixed. Feature extraction can be performed using computer vision software such as OpenCV™. Feature extraction can be based on the use of HoGs. HoGs can include feature descriptors and can be used to count occurrences of gradient orientation in localized portions or regions of the image. Other techniques can be used for counting occurrences of gradient orientation, including edge orientation histograms, scale-invariant feature transformation descriptors, etc. The AU recognition tasks can also be performed using Local Binary Patterns (LBPs) and Local Gabor Binary Patterns (LGBPs). The HoG descriptor represents the face as a distribution of intensity gradients and edge directions and is robust in its ability to translate and scale. Differing patterns, including groupings of cells of various sizes and arranged in variously sized cell blocks, can be used. For example, 4×4 cell blocks of 8×8-pixel cells with an overlap of half of the block can be used. Histograms of channels can be used, including nine channels or bins evenly spread over 0-180 degrees. In this example, the HoG descriptor on a 96×96 image is 25 blocks×16 cells×9 bins=3600, the latter quantity representing the dimension. AU occurrences can be rendered. The videos can be grouped into demographic datasets based on nationality and/or other demographic parameters for further detailed analysis. This grouping and other analyses can be facilitated via semiconductor-based logic.

Figure 20:
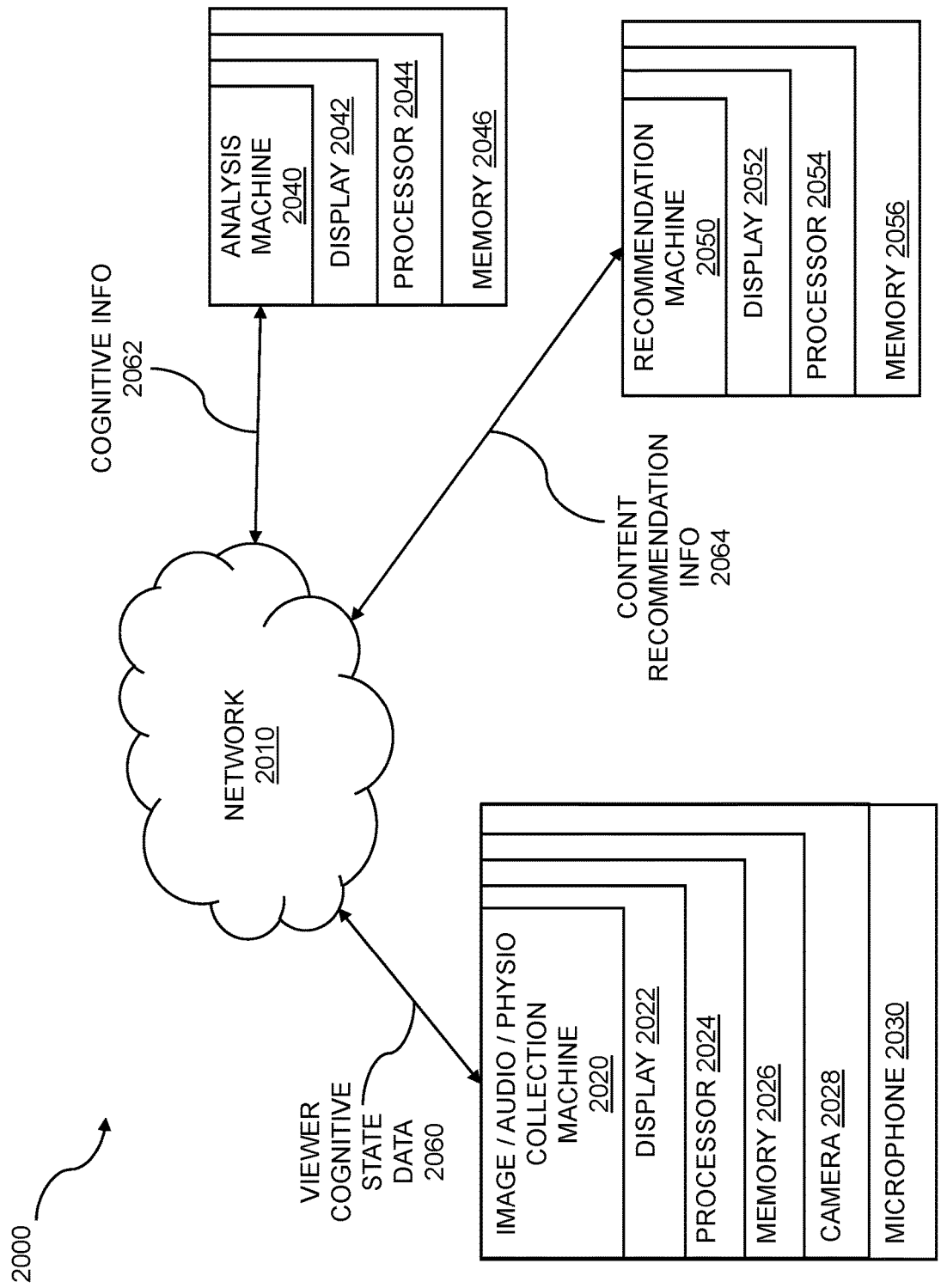
FIG. 20 is a system diagram for affect-based recommendations.

FIG. 20 is a system diagram for affect-based recommendations. Affect can be used for vehicle content recommendation, where the recommendation uses ranking and correlating of images, audio data, or physiological data. A first media presentation is played on a video client to a vehicle occupant. Cognitive state data is captured for the vehicle occupant, where the cognitive state data includes video facial data from the vehicle occupant during the first media presentation playing. The cognitive state data can be captured using cameras, biosensors, inertial measurement units, etc., within the vehicle. An analysis server is used to rank the first media presentation relative to another media presentation based on the cognitive state data which was captured for the vehicle occupant. The ranking is for the vehicle occupant. The analysis server is used to correlate the cognitive state data which was captured for the vehicle occupant to cognitive state data collected from other people who experienced the first media presentation. One or more further media presentation selections are recommended to the vehicle occupant, based on the ranking and the correlating. Audio information can be obtained from the occupant of the vehicle and can augment the correlating based on the audio information. Physiological information can be obtained from the occupant of the vehicle and can augment the correlating based on the physiological information.

The system 2000 can include a network 2010 (Internet, intranet, or another computer network), which can be used for communication among various machines. An image, audio, or physio collection machine 2020 has a memory 2026 which stores instructions and one or more processors 2024 attached to the memory 2026, wherein the one or more processors 2024 can execute instructions. The image, audio, or physio collection machine 2020 can also have a network connection to carry viewer cognitive state data 2060, and a display 2022 that can present cognitive state data, cognitive state profiles, mental state data, mental state profiles, emotional states, emotional state profiles, and so on. The image, audio, or physio collection machine 2020 can collect cognitive state data including image data, facial data, voice data, audio data, physiological data, etc., from an occupant of a vehicle. In some embodiments, there are multiple image, audio, or physio collection machines 2020 that each collect cognitive state data including facial data. This type of collection machine can have a camera 2028, a microphone 2030, or other sensors. In many embodiments, a camera, a microphone, or physiological sensors will be present. Other embodiments include obtaining audio information and augmenting the correlating of the cognitive state data with the audio information. The audio data can include speech, non-speech vocalizations, etc. Further embodiments may include obtaining physiological information from the occupant of the vehicle and augmenting the analyzing based on the physiological information. The physiological data can include heart rate, heart rate variability, respiration rate, skin conductivity, and so on. Once the viewer cognitive state data 2060 has been collected, the image, audio, or physio collection machine 2020 can upload information to an analysis machine 2040, based on the cognitive state data from the occupant of the vehicle. The image, audio, or physio collection machine 2020 can communicate with the analysis machine 2040 over the network 2010, the Internet, some other computer network, or by another method suitable for communication between two machines. In some embodiments, the analysis machine 2040 functionality is embodied in the image and audio collection machine 2020.

The analysis machine 2040 can have a network connection for cognitive states or cognitive state information 2062, a memory 2046 which stores instructions, and one or more processors 2044 attached to the memory 2046, wherein the one or more processors 2044 can execute instructions. The analysis machine 2040 can receive cognitive state information, collected from an occupant of the vehicle, from the image, audio, or physio collection machine 2020, and can determine a cognitive state of the occupant. The analysis machine 2040 can also compare further cognitive state data with the cognitive state profile while the occupant is in a second vehicle. In some embodiments, the analysis machine 2040 also allows a user to view and evaluate the cognitive state data or other data for the occupant of the vehicle on a display 2042. The analysis machine 2040 can then provide the cognitive state information 2062 to the recommendation machine 2050. In some embodiments, the image, audio, or physio collection machine 2020 can also function as the recommendation machine 2050. In further embodiments, the cognitive state data that was analyzed can be based on intermittent obtaining of images that include facial data.

The recommendation machine 2050 can have a memory 2056 which stores instructions, and one or more processors 2054 attached to the memory 2056, wherein the one or more processors 2054 can execute instructions. The recommendation machine can use a computer network 2010, the Internet, or another computer communication method, to request the cognitive state information 2062 from the analysis machine. The recommendation machine 2050 can receive content recommendation information 2064, based on the cognitive state data 2060, from the occupant of the vehicle. The cognitive state information and vehicle content recommendation information for the occupant can be presented on a display 2052. In some embodiments, the recommendation machine is configured to receive viewer cognitive state data collected from an occupant of the vehicle, in a real-time or near real-time embodiment. In other embodiments, the recommendation machine is configured to receive the cognitive state data on an intermittent basis. In at least one embodiment, a single computer incorporates the image, audio, or physio collection machine, the analysis machine, and the recommendation machine functionalities.

The system 2000 can comprise a computer system for affect-based recommendations comprising: a memory for storing instructions; one or more processors attached to the memory wherein the one or more processors are configured to: play a first media presentation to a vehicle occupant; capture cognitive state data for the vehicle occupant, wherein the cognitive state data includes video facial data from the vehicle occupant during the first media presentation playing; rank the first media presentation relative to another media presentation based on the cognitive state data which was captured for the vehicle occupant, wherein the ranking is for the vehicle occupant; correlate the cognitive state data which was captured for the vehicle occupant to cognitive state data collected from other people who experienced the first media presentation; and recommend to the vehicle occupant one or more further media presentation selections, based on the ranking and the correlating.

In embodiments, a computer program product embodied in a non-transitory computer readable medium for affect based recommendations, the computer program product comprising code which causes one or more processors to perform operations of: playing, on a video client, a first media presentation to a vehicle occupant; capturing cognitive state data for the vehicle occupant, wherein the cognitive state data includes video facial data from the vehicle occupant during the first media presentation playing; ranking, on an analysis server, the first media presentation relative to another media presentation based on the cognitive state data which was captured for the vehicle occupant, wherein the ranking is for the vehicle occupant; correlating, on the analysis server, the cognitive state data which was captured for the vehicle occupant to cognitive state data collected from other people who experienced the first media presentation; and recommending to the vehicle occupant one or more further media presentation selections, based on the ranking and the correlating.

Each of the above methods may be executed on one or more processors on one or more computer systems. Embodiments may include various forms of distributed computing, client/server computing, and cloud-based computing. Further, it will be understood that for each flow chart in this disclosure, the depicted steps or boxes are provided for purposes of illustration and explanation only. The steps may be modified, omitted, or re-ordered and other steps may be added without departing from the scope of this disclosure. Further, each step may contain one or more sub-steps. While the foregoing drawings and description set forth functional aspects of the disclosed systems, no particular arrangement of software and/or hardware for implementing these functional aspects should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. Each element of the block diagrams and flowchart illustrations, as well as each respective combination of elements in the block diagrams and flowchart illustrations, illustrates a function, step or group of steps of the methods, apparatus, systems, computer program products and/or computer-implemented methods. Any and all such functions may be implemented by computer program instructions, by special-purpose hardware-based computer systems, by combinations of special purpose hardware and computer instructions, by combinations of general purpose hardware and computer instructions, and so on. Any and all of which may be generally referred to herein as a "circuit," "module," or "system."

A programmable apparatus which executes any of the above-mentioned computer program products or computer implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are not limited to applications involving conventional computer programs or programmable apparatus that run them. It is contemplated, for example, that embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized. The computer readable medium may be a non-transitory computer readable medium for storage. A computer readable storage medium may be electronic, magnetic, optical, electromagnetic, infrared, semiconductor, or any suitable combination of the foregoing. Further computer readable storage medium examples may include an electrical connection having one or more wires, a portable computer diskette, a hard disk, a random-access memory (RAM), a read-only memory (ROM), an erasable programmable read-only memory (EPROM, Flash, MRAM, FeRAM, or phase change memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed more or less simultaneously to enhance utilization of the processor and to facilitate substantially simultaneous functions. By way of implementation, any and all methods, program codes, program instructions, and the like described herein may be implemented in one or more thread. Each thread may spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the entity causing the step to be performed.

While the invention has been disclosed in connection with preferred embodiments shown and described in detail, various modifications and improvements thereon will become apparent to those skilled in the art. Accordingly, the spirit and scope of the present invention is not to be limited by the foregoing examples but is to be understood in the broadest sense allowable by law.

What is claimed is:

1. A computer-implemented method for affect-based recommendations comprising:
    playing, on a video client, a first media presentation to a vehicle occupant;
    capturing cognitive state data for the vehicle occupant, wherein the cognitive state data includes video facial data from the vehicle occupant during the first media presentation playing;
    ranking, on an analysis server, the first media presentation relative to another media presentation based on the cognitive state data which was captured for the vehicle occupant, wherein the ranking is for the vehicle occupant;
    correlating, on the analysis server, the cognitive state data which was captured for the vehicle occupant to cognitive state data collected from other people who experienced the first media presentation, wherein the correlating is based on identifying similar likes, within a percentage threshold, from a demographic group similar to a demographic group of the vehicle occupant; and
    recommending to the vehicle occupant one or more media presentation selections, based on the ranking and the correlating.

2. The method of claim 1 further comprising correlating the cognitive state data which was captured for the vehicle occupant to cognitive state data collected from other people who experienced the first media presentation.

3. The method of claim 2 wherein the correlating is based on identifying similar likes.

4. The method of claim 2 wherein the correlating is based on identifying and using maximally dissimilar responses during part of the correlating.

5. The method of claim 1 further comprising identifying a cognitive state event type based on the correlating.

6. The method of claim 1 wherein the first media presentation includes a first socially shared live-stream video.

7. The method of claim 6 further comprising generating highlights for the first socially shared live-stream video, based on the cognitive state data that was captured.

8. The method of claim 6 wherein the first socially shared live-stream video includes an overlay with information on the cognitive state data that was captured.

9. The method of claim 1 further comprising analyzing the cognitive state data to produce cognitive state information.

10. The method of claim 1 wherein the ranking is based on anticipated preferences for the vehicle occupant.

11. The method of claim 1 wherein the cognitive state data is captured from multiple people and further comprises aggregating the cognitive state data from the multiple people.

12. The method of claim 1 further comprising inferring cognitive states, based on both the cognitive state data which was captured and analysis of the video facial data.

13. The method of claim 1 wherein the first media presentation is played on a mobile device and further comprising recording of facial images with the mobile device as part of the capturing of the cognitive state data.

14. The method of claim 1 wherein the recommending occurs while the vehicle occupant occupies the vehicle.

15. The method of claim 1 wherein the recommending occurs after the vehicle occupant leaves the vehicle.

16. The method of claim 1 further comprising obtaining audio information from the occupant of the vehicle and augmenting the correlating based on the audio information.

17. The method of claim 16 wherein the audio information includes speech.

18. The method of claim 16 wherein the audio information includes non-speech vocalizations.

19. The method of claim 1 further comprising tagging the cognitive state with sensor data.

20. The method of claim 1 wherein the video facial data includes near-infrared content.

21. The method of claim 20 wherein the correlating is modified, based on the near-infrared content of the video facial data.

22. The method of claim 1 further comprising comparing, on the analysis server, the cognitive state data that was captured for the vehicle occupant against a plurality of cognitive state event temporal signatures.

23. The method of claim 22 wherein the cognitive state event temporal signatures include a shape of an intensity transition.

24. The method of claim 22 further comprising matching a first cognitive state event signature, from the plurality of cognitive state event temporal signatures, against the cognitive state data that was captured.

25. The method of claim 24 wherein the recommending the one or more media presentation selections is further based on the matching of the first cognitive state event signature.

26. A computer program product stored on a non-transitory computer-readable medium for affect based recommendations, the computer program product comprising code which causes one or more processors to perform operations of:

playing, on a video client, a first media presentation to a vehicle occupant;

capturing cognitive state data for the vehicle occupant, wherein the cognitive state data includes video facial data from the vehicle occupant during the first media presentation playing;

ranking, on an analysis server, the first media presentation relative to another media presentation based on the cognitive state data which was captured for the vehicle occupant, wherein the ranking is for the vehicle occupant;

correlating, on the analysis server, the cognitive state data which was captured for the vehicle occupant to cognitive state data collected from other people who experienced the first media presentation, wherein the correlating is based on identifying similar likes, within a percentage threshold, from a demographic group similar to a demographic group of the vehicle occupant; and recommending to the vehicle occupant one or more media presentation selections, based on the ranking and the correlating.

27. A computer system for affect based recommendations comprising:

a memory for storing instructions;

one or more processors attached to the memory wherein the one or more processors are configured to:

play a first media presentation to a vehicle occupant;

capture cognitive state data for the vehicle occupant, wherein the cognitive state data includes video facial data from the vehicle occupant during the first media presentation playing;

rank the first media presentation relative to another media presentation based on the cognitive state data which was captured for the vehicle occupant, wherein the ranking is for the vehicle occupant;

correlate the cognitive state data which was captured for the vehicle occupant to cognitive state data collected from other people who experienced the first media presentation, wherein the correlation is based on an identification of similar likes, within a percentage threshold, from a demographic group similar to a demographic group of the vehicle occupant; and recommend to the vehicle occupant one or more media presentation selections, based on the ranking and the correlating.

* * * * *